(12) United States Patent
Kobayashi

(10) Patent No.: US 11,985,932 B2
(45) Date of Patent: May 21, 2024

(54) UNNATURAL PLANT SHOWING INDUCED GENE EXPRESSION AND METHOD FOR PRODUCING SAME

(71) Applicant: National University Corporation Mie University, Mie (JP)

(72) Inventor: Issei Kobayashi, Mie (JP)

(73) Assignee: National University Corporation Mie University, Tsu (JP)

( * ) Notice: Subject to any disclaimer, the term of this patent is extended or adjusted under 35 U.S.C. 154(b) by 184 days.

(21) Appl. No.: 17/605,861

(22) PCT Filed: Apr. 21, 2020

(86) PCT No.: PCT/JP2020/017159
§ 371 (c)(1),
(2) Date: Oct. 26, 2021

(87) PCT Pub. No.: WO2020/218279
PCT Pub. Date: Oct. 29, 2020

(65) Prior Publication Data
US 2022/0210990 A1 Jul. 7, 2022

(30) Foreign Application Priority Data

Apr. 25, 2019 (JP) ................................ 2019-083683

(51) Int. Cl.
*A01H 3/04* (2006.01)
*A01H 6/46* (2018.01)
*A01H 6/82* (2018.01)

(52) U.S. Cl.
CPC ............. *A01H 3/04* (2013.01); *A01H 6/4636* (2018.05); *A01H 6/823* (2018.05)

(58) Field of Classification Search
None
See application file for complete search history.

(56) References Cited

U.S. PATENT DOCUMENTS

2008/0293059 A1* 11/2008 Bednarek ............... A01H 4/008
435/6.12

FOREIGN PATENT DOCUMENTS

| EP | 3685668 A2 * | 7/2020 | ............. A01G 17/00 |
|---|---|---|---|
| JP | 1991280818 | 12/1991 | |
| JP | 1994141718 | 5/1994 | |
| JP | 2002315572 | 10/2002 | |
| WO | 2016/146552 A1 | 9/2016 | |

OTHER PUBLICATIONS

Hatano, T. et al., Genome-wide methylation pattern changes in rice and their potential for artificial orientation, Programs and Abstracts of the 37th Annual Meeting of the Molecular Biology Society of Japan, Nov. 2014.

Hatano, T. et al., Genome-wide methylation pattern changes in rice and the possibility of artificial orientation, Abstracts of the 56th Annual Meeting of the Japanese Society of Plant Physiologists: pp. 272, Mar. 9, 2015.

Kobayashi, Y. et al., Possibility of the disease resistance breeding by artificially directing epigenetic mutations, Japanese Journal of Phytopathology, 82(1): 52-53, Mar. 17, 2016.

Kageyama, C. et al., The properties of elicitor-responsive photon emissions enhanced by pretreatment with plant defense activators, Japanese Journal of Phytopathology, 73(1): 15-20, Sep. 14, 2007.

Jiang, C. et al., Regenerant *Arabidopsis* Lineages Display a Distinct Genome-Wide Spectrum of Mutations Conferring Variant Phenotypes, Current Biology, 21: 1385-1390, Jul. 28, 2011.

Blackhall, N. et al., Callus Initiation, Maintenance, and Shoot Induction in Rice, in Plant Cell Culture Protocols, Robert D. Hall (Editor), pp. 19-29, Humana Press, Totowa, NJ, 1999 (Abstract).

Takatsuji, H. et al., Development of disease-resistant rice using regulatory components of induced disease resistance, Frontiers in Plant Science, vol. 5, Article 630, pp. 1-12, Nov. 13, 2014.

Robledo-Paz, A. et al., Callus and Suspension Culture Induction, Maintenance, and Characterization, in Plant Cell Culture Protocols, Second Edition, V. M. Loyola-Vargas et al. (Editors), pp. 59-70, Humana Press, Totowa, NJ, 2006 (Abstract).

Yang, Y. et al., Comparative Transcriptome Analysis of Shoots and Roots of TNG67 and TCN1 Rice Seedlings under Cold Stress and Following Subsequent Recovery: Insights into Metabolic Pathways, Phytohormones, and Transcription Factors, PLOS One, 10(7):e0131391, pp. 1-37, Jul. 2, 2015.

Magome, H. et al., The DDF1 transcriptional activator upregulates expression of a gibberellin-deactivating gene, GA2ox7, under high-salinity stress in *Arabidopsis*, The Plant Journal, 56: 613-626, Aug. 15, 2008.

Krishnamurthy, P. et al., Transcriptomics analysis of salt stress tolerance in the roots of the mangrove Avicennia officinalis, Scientific Reports, 7:10031, Aug. 30, 2017.

Zhou, Y. et al., Transcriptome Analysis of Salt Stress Responsiveness in the Seedlings of Dongxiang Wild Rice (*Oryza rufipogon* Griff.), PLOS One, 11(1):e0146242, pp. 1-25, Jan. 11, 2016.

(Continued)

*Primary Examiner* — Weihua Fan
(74) *Attorney, Agent, or Firm* — Julie K. Staple; Dinsmore & Shohl LLP

(57) ABSTRACT

A problem to be solved by the present invention is to provide a non-natural plant in which expression of a gene of interest is induced and a method for producing the same. Particularly, the present invention relates to a non-natural plant in which the expression of the gene is stably induced even in the absence of a physical or chemical stimulus inducing the expression of the gene, and a method for producing the same. When the induction of the expression of the gene enhances a trait of a plant of interest, the present invention provides a non-natural plant in which the trait is enhanced and a method for producing the same. To solve the problem, a non-natural regenerated plant in which the expression of the gene is induced can be produced by forming a callus from a portion of the plant of interest and then subjecting the callus to a treatment by which the expression of the gene is induced.

25 Claims, 17 Drawing Sheets
Specification includes a Sequence Listing.

(56) References Cited

OTHER PUBLICATIONS

Baldoni, E. et al., Comparative Leaf and Root Transcriptomic Analysis of two Rice Japonica Cultivars Reveals Major Differences in the Root Early Response to Osmotic Stress, Rice, 9(25): pp. 1-20, May 23, 2016.

Iwai, T. et al., Probenazole-Induced Accumulation of Salicylic Acid Confers Resistance to Magnaporthe grisea in Adult Rice Plants, Plant Cell Physiol., 48(7): 915-924, 2007.

Bektas, Y. et al., Synthetic plant defense elicitors, Frontiers in Plant Science, vol. 5, Article 804, pp. 1-17, Jan. 26, 2015.

Shimono, M. et al., Rice WRKY45 Plays a Crucial Role in Benzothiadiazole-Inducible Blast Resistance, The Plant Cell, 19: 2064-2076, Jun. 29, 2007.

Yasuda, M., Regulation mechanisms of systemic acquired resistance induced by plant activators, J. Pestic. Sci., 32(3): 281-282, 2007.

[IPEA/409] English Translation of International Preliminary Report on Patentability Chapter II for PCT/JP2020/017159, dated Apr. 27, 2021.

Translation of the International Search Report for PCT/JP2020/017159, dated Jul. 28, 2020.

English Translation of Office Action for Japanese Patent Application No. 2021-516124, dated Jan. 24, 2024.

Office Action for apanese Patent Application No. 2021-516124, dated Jan. 24, 2024.

* cited by examiner

[Fig. 2]
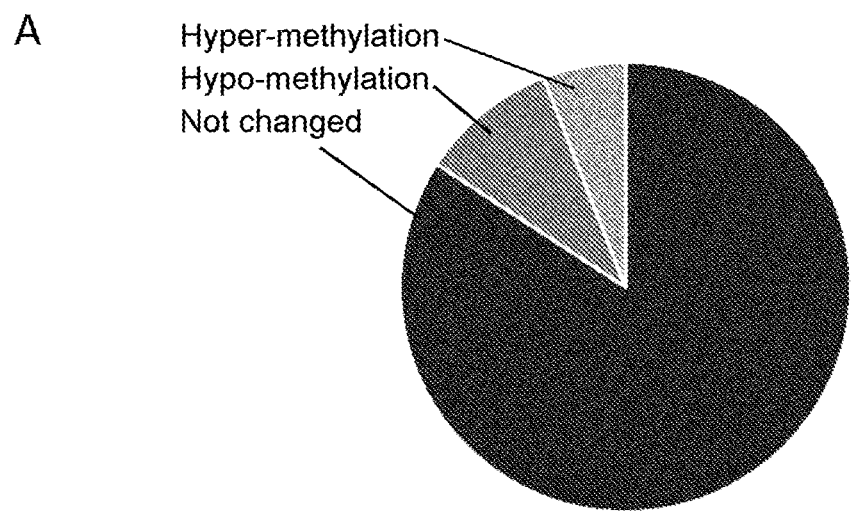
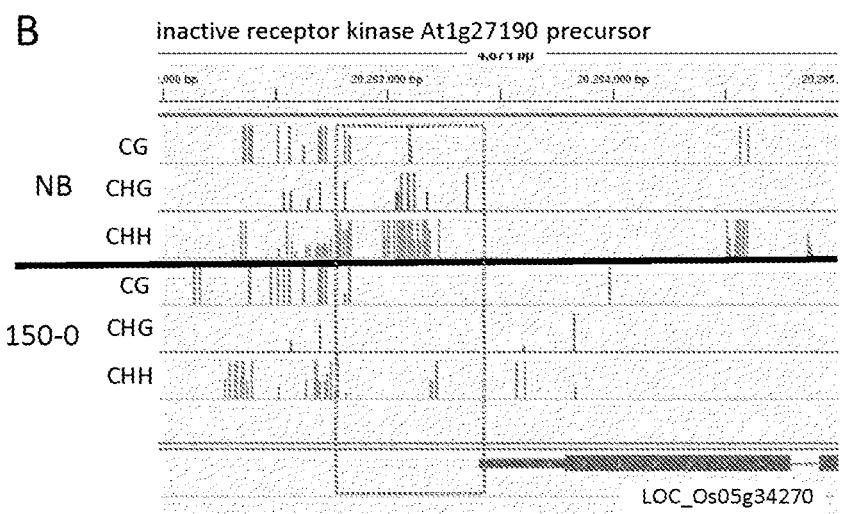
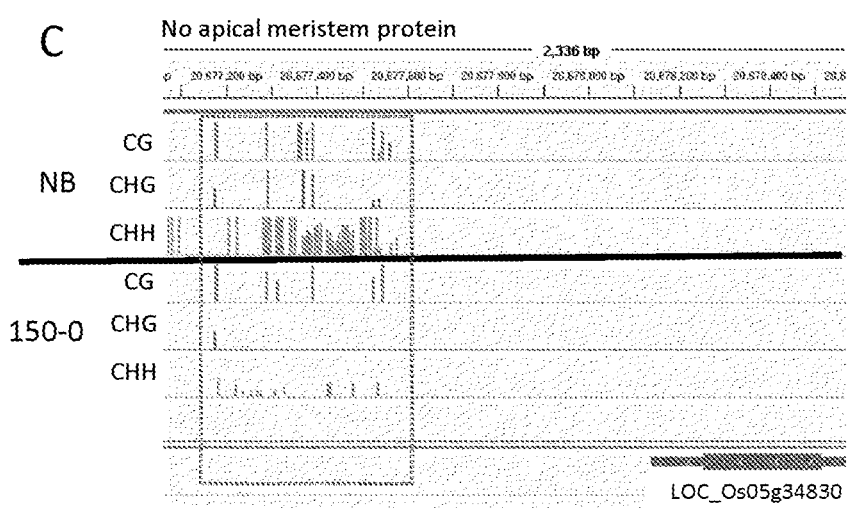

[Fig. 3-1]

<DISEASE RESISTANCE>

LOC_Os05g47770 serine/threonine-protein kinase At1g18390 precursor, putative, expressed

[Fig. 3-2]

<LOW-TEMPERATURE RESISTANCE>

LOC_Os02g52210 zinc finger, C3HC4 type domain containing protein, expressed

[Fig. 3-3]

<SALT RESISTANCE>

LOC_Os05g38530

DnaK family protein, putative, expressed

[Fig. 4]
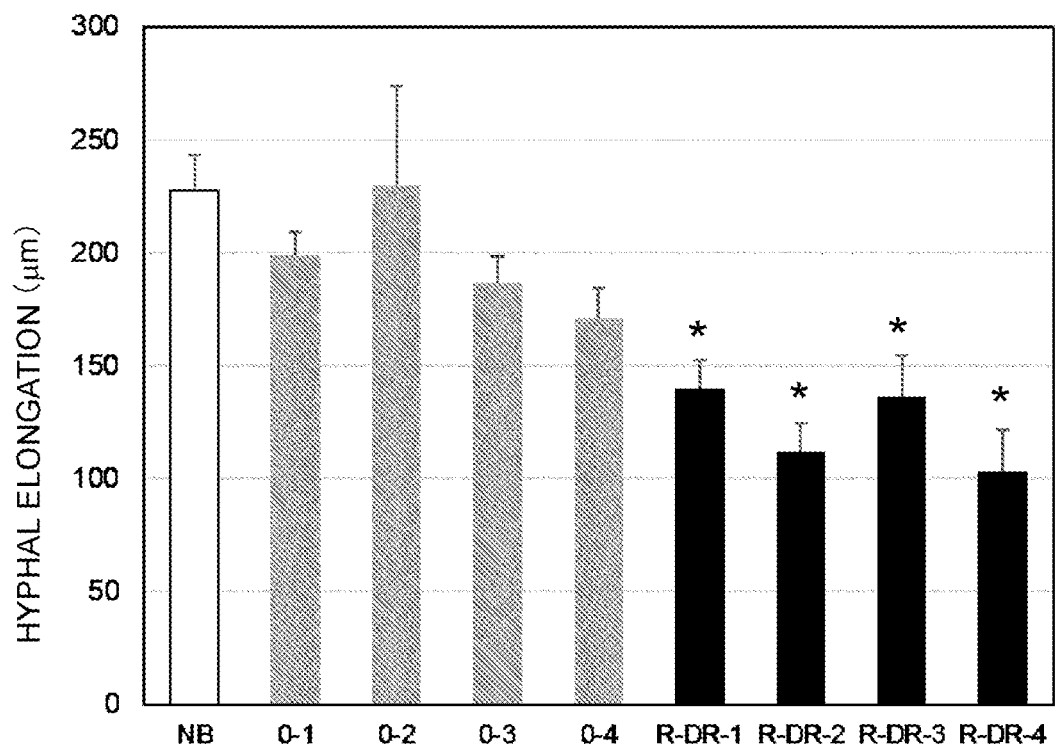
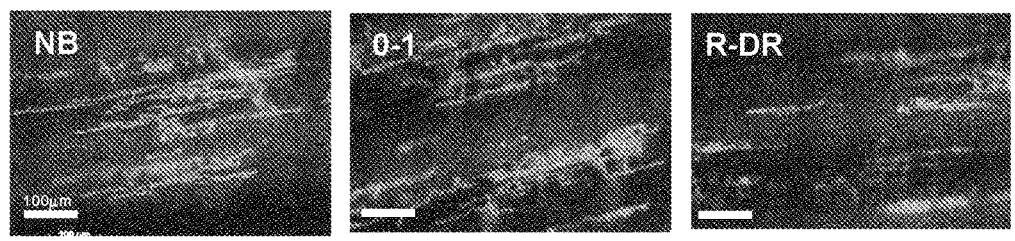

FIG 7-1

[Fig. 8-1]
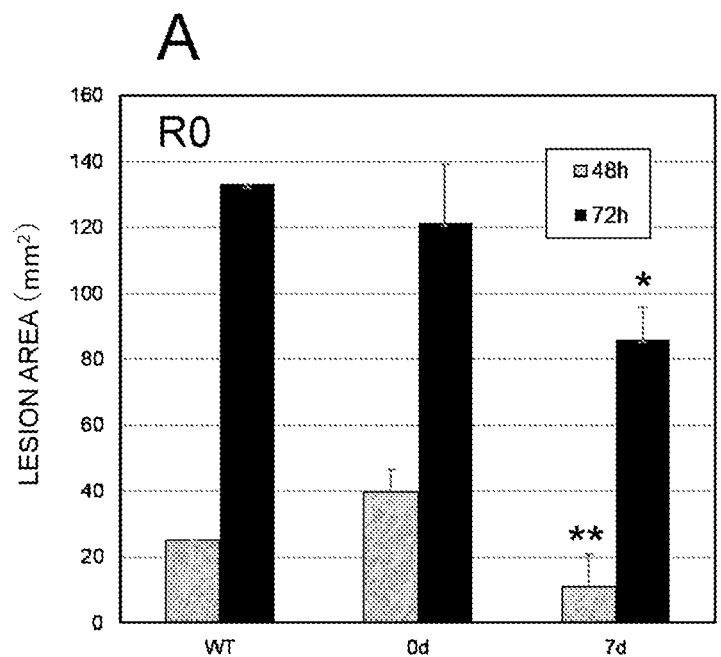
[Fig. 8-2]
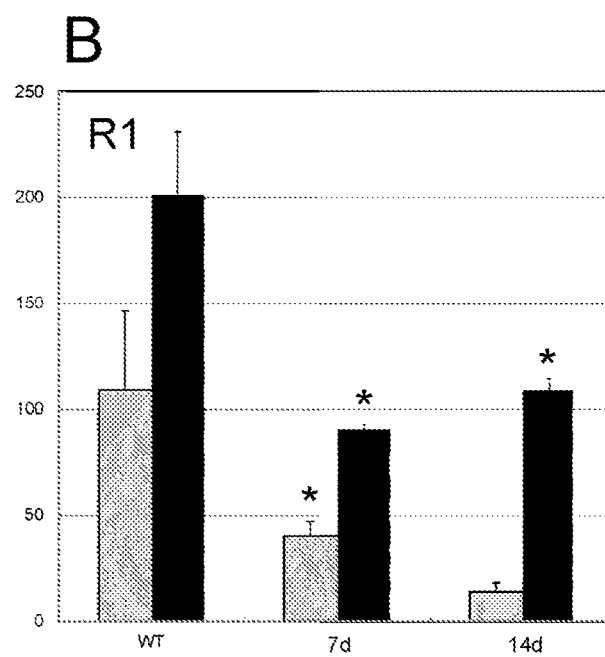

[Fig. 8-3]
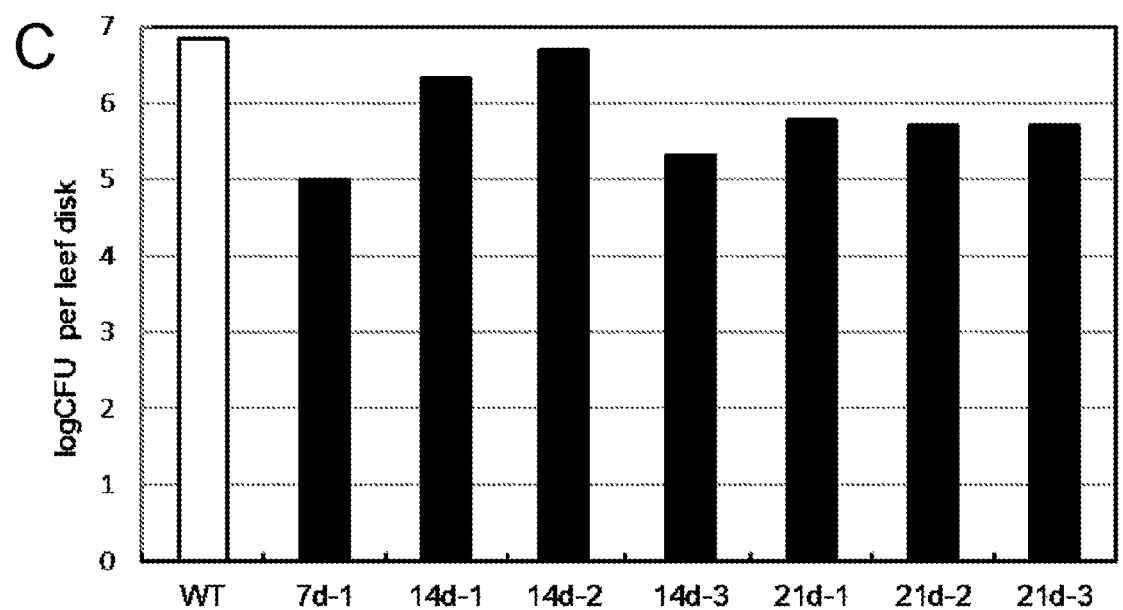

[Fig. 9]
A
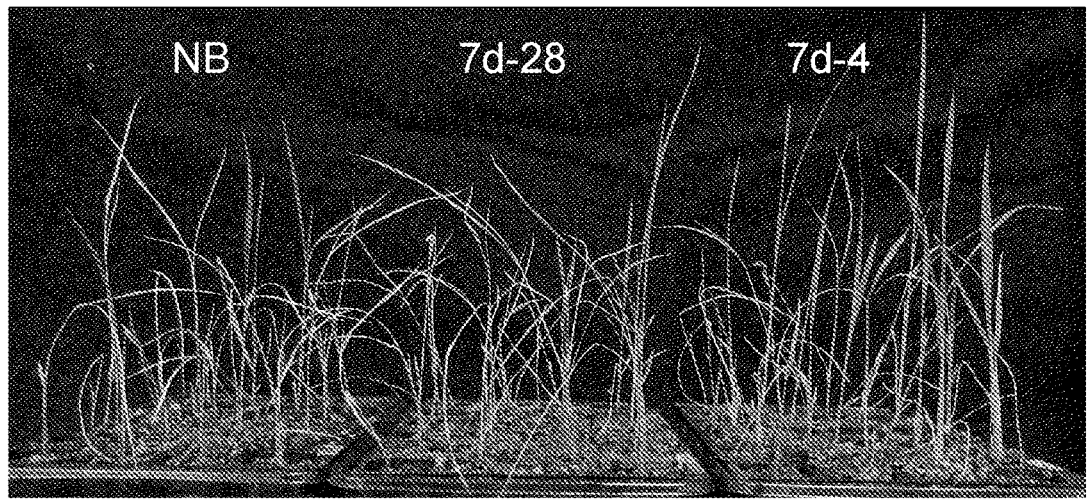
B
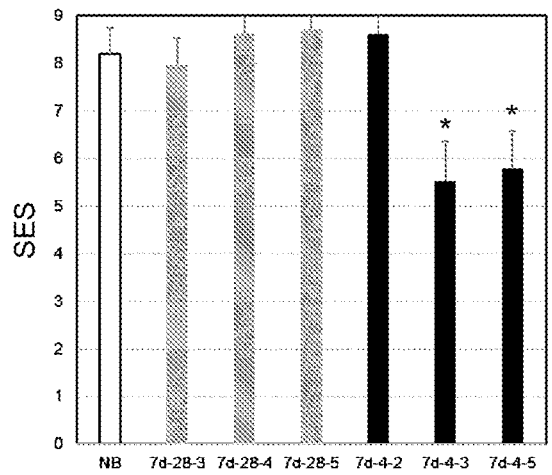
C
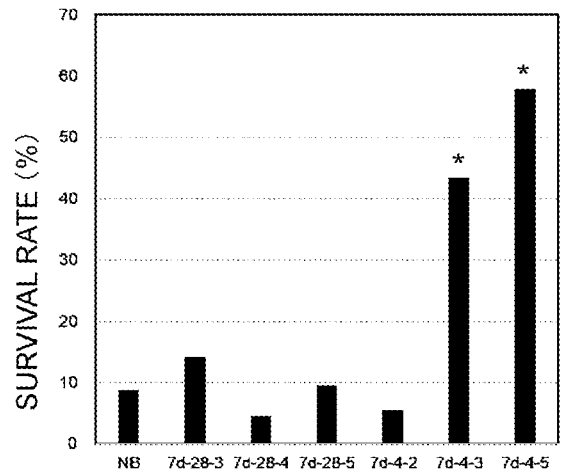

[Fig. 10]
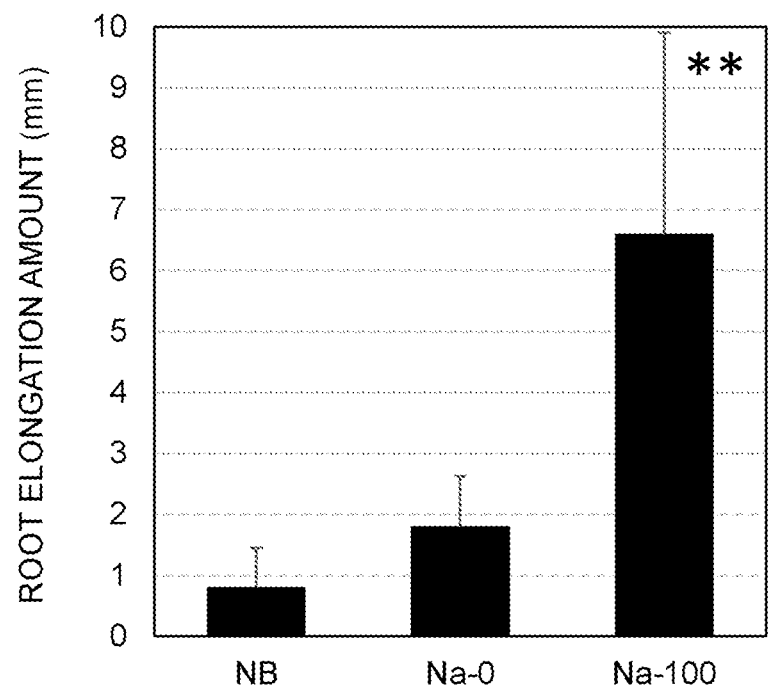

[Fig. 12A]
A
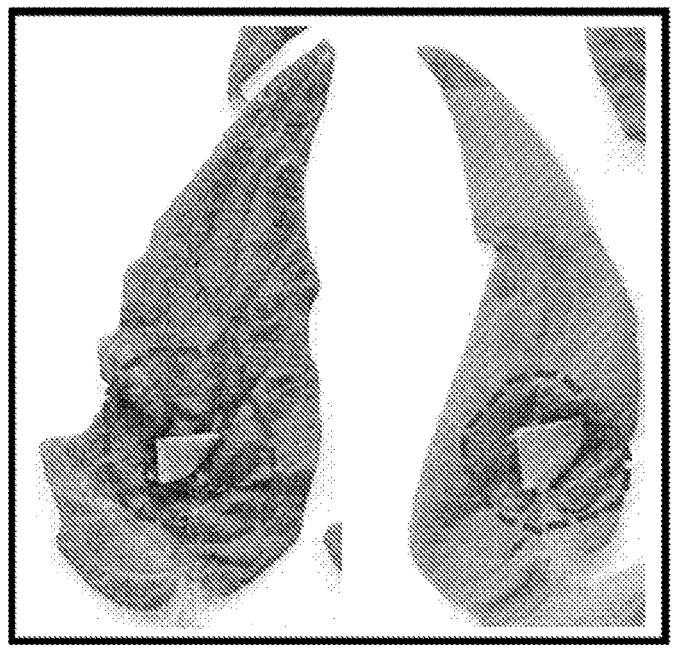
[Fig. 12B]
B
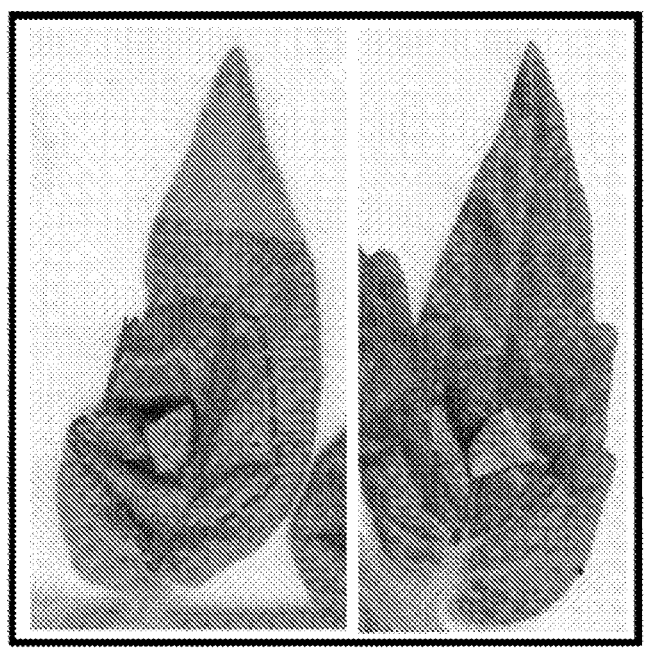

[Fig. 12C]
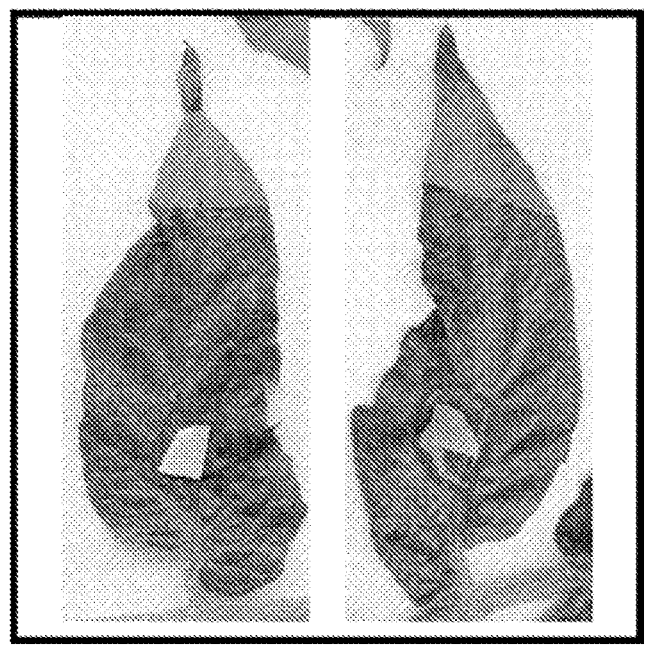
[Fig. 12D]
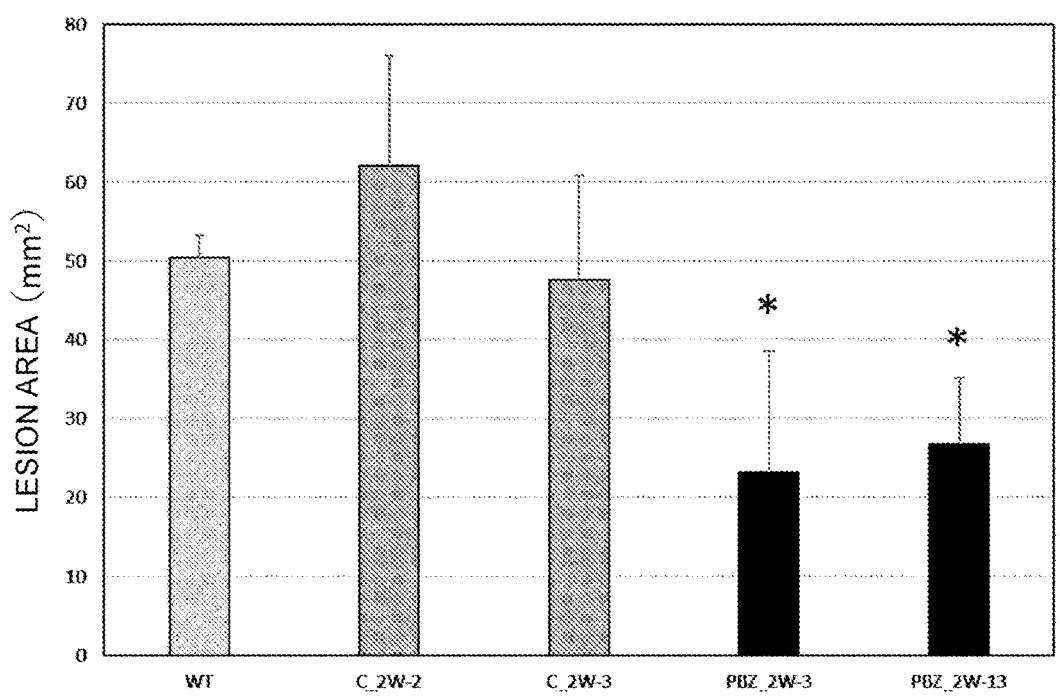

SEQUENCE LISTING

<160> NUMBER OF SEQ ID NOS: 12

<210> SEQ ID NO 1
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: NB_LOC_Os05g47770

<400> SEQUENCE: 1

```
atttaagcag ccggtgtaag ctcgcaccgt gcgcagtcgt cgccatgccg ccactactct      60
tccacctcct cgtactctcc gtcgtcgtcg tcgtcgttag cggtggcgcg gccactgccg     120
gcggcggaac gtacgacgac gccatatgcg cgaggccgat cttttgcggc gagcaggtgg     180
agatcaagta ccctttctac ctctccaaca ccacggatca ggtcgtcgtc gtcgacggga     240
acacccgcta ctgcggctac ccgtggctgg gcatcatctg cgaccacgac cgcgccatcc     300
tgcgactcgg gaattacaac tacaccgtcc tggagatcaa ccacggcaac cacaccgtca     360
cggtggccga ctccgacgcg ctcgacggcg gcgactgccc gagggtgaag cacaacgtca     420
ccctcccgga ggtgctcacg ttcccgagcc ccggcaacga cagcatcacc ttcttcttcg     480
actgcaactc cacggccaac gtcgtgctgc ggccgccgcc gtacatccgc ccgatcaact     540
gcagcacctt cgacttcccg gggcggcgag acacggcgcc gtctttcgtc gccacgcagc     600
cggacgtggc aggcgagacg gagtggttgg ggctgtgcaa ggaggtggtg atggtgcccg     660
tgctcaagga ttggctcatg aacgagaagt actacggcaa attgggcgac gatggatacg     720
gcgccgtgct gaagcgcggg ttccagctga gctgggaccc gacggcgggg atgtgccacg     780
agtgcgaggt atccggggga cgctgcagct acggcacgaa gaacgagttc ctgggatgcc     840
tgtgctccga tggccacgtc agcaaaacag actgcggtga gttagtaccc tcttgcatac     900
atcaacatat ttaattacta gtattaccta gtattacttt cattccgaaa taaactaacg     960
taatacataa catcacatat cgtaattcta agaatttaga t                       1001
```

<210> SEQ ID NO 2
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: Koshi_LOC_Os05g47770

<400> SEQUENCE: 2

```
atttaagcag ccggtgtaag ctcgcaccgt gcgcagtcgt cgccatgccg ccactactct      60
tccacctcct cgtactctcc gtcgtcgtcg tcgtcgttag cggtggcgcg gccactgccg     120
gcggcggcac gtacgacgac gccatatgcg cgaggccgat cttttgcggc gagcaggtgg     180
agatcaagta ccctttctac ctctccaaca cgacggatca ggtcgtcgtc gtcgacggga     240
acacccgcta ctgcggctac ccgtggctgg catcatctg cgaccacgac cgcgccatcc      300
tgcgactcgg gaattacaac tacaccgtcc tggagatcaa ccacggcaac cacaccgtca     360
cggtggccga ctccgacgcg ctcgacgcg gcgactgccc gagggtgaag cacaacgtca      420
ccctccccgga ggtgctcacg ttcccgagcc ccggcaacga cagcatcacc ttcttcttcg    480
actgcaactc cacggccaac gtcgtgctgc ggccgccgcc gtacatccgc ccgatcaact     540
gcagcacctt cgacttcccg gggcggcgag acacggcgcc gtctttcgtc gccacgcagc    600
cggacgtggc aggcgagacg gagtggttgg ggctgtgcaa ggaggtggtg atggtgcccg     660
tgctcaagga ttggctcatg aacgagaagt actacggcaa attgggcgac gatggatacg     720
gcgccgtgct gaagcgcggg ttccagctga gctgggaccc gacggcgggg atgtgccacg     780
agtgcgaggt atccggggga cgctgcagct acggcacgaa gaacgagttc ctgggatgcc     840
tgtgctccga tggccacgtc agcaaaaacag actgcggtga gttagtaccc tcttgcatac    900
atcaacatat ttaattacta gtattaccta gtattacttt cattccgaaa taaactaacg     960
taatacataa catcacatat cgtaattcta agaatttaga t                        1001
```

<210> SEQ ID NO 3
<211> LENGTH: 1027
<212> TYPE: DNA
<213> ORGANISM: Oryza sativa
<220> FEATURE:
<221> NAME/KEY: promoter
<222> LOCATION: (1)..(1027)
<223> OTHER INFORMATION: RP_Bio-226_LOC_Os05g47770

<400> SEQUENCE: 3

```
atttaagcag ccggtgtaag ctcgcaccgt gcgcagtcgt cgccatgccg ccactactct      60
tccacctcct cgtactctcc gtcgtcgtcg tcgtcgttag cggtggcgcg gccactgccg     120
gcggcggaac gtacgacgac gccatatgcg cgaggccgat cttctgcggc gagcacgtgg     180
agatcaagta ccctttcttc ctctccaaca cgacggatca ggtcgtcgtc gacgggatca     240
acaccaccgg ccgctactgc ggctacccgt ggctgggcat catctgcgac gaccacgacg     300
gcggcggcag cagcaaccgc gccatcctgc gactcgggaa ttacaactac accgtgcttg     360
aaatcaacca tggcaaccac accgtcacgg tggccgactc cgacgcgctc gacggcggcg     420
gctgcccgag ggtgaagcac aacgtcaccc tccctccggt gctcacgttc ccgagccccg     480
gcaacgacag catcaccttc ttcttcgact gcaaccccac ggcggacgtc gtgctgcggc     540
cgccgccgta catccgcccg atcaactgca gcaccttcga cttccaggtg cggcgagaca    600
cggcgccgtc tttcgtcgcc acgcagccgg acgtggcagg cgagacggag tggttgggc     660
tgtgcaagga ggtggtgatg gtgcccgtgc tcaaggattg gctcatgaac gagaagtact    720
acggcaaatt gggcgacgat ggatacggcg ccgtgctgaa gcgcgggttc cagctgagct     780
gggacccgac ggcggggatg tgccacgagt gcgaggtatc cggggacgc tgcagctacg     840
gcacgaagaa cgagttcctg ggatgcctgt gctccgatgg ccacgtcagc aaaacagact    900
```

| gcggtgagtt agtaccctct tgcatacatc aaatatttaa ttactagtat tacctagtat | 960 |
| tactttcatt ccgaaataaa ctaacgtaat acataacatc acatatcgta attctaagaa | 1020 |
| tttagat | 1027 |

<210> SEQ ID NO 4
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: Shuhui498_LOC_Os05g47770

<400> SEQUENCE: 4

| atttaagcag ccggtgtaag ctcgcaccgt gcgcagtcgt cgccatgccg ccactactct | 60 |
| tccaccccct cgtactctcc gtcgtcgtcg tcgtcgttag cggtggcgcg gccactgccg | 120 |
| gcggcggaac gtacgacgac gccatatgcg cgaggccgat cttctgcggc gagcacgtgg | 180 |
| agatcaagta ccctttctac ctctccaaca cgacggatca ggtcgtcgtc gtcgacggga | 240 |
| acacccgcta ctgcggctac ccgtggctgg gcatcatctg cgaccacgac cgcgccatcc | 300 |
| tgcgactcgg gaattacaac tacaccgtgc ttgacatcaa ccacgcaac cacaccgtca | 360 |
| cggtggccga ccccgacgcg ctcgacggcg gcggctgccc gagggtgaag cacaacgtca | 420 |
| ccctcccgga ggttctcacg ttctcgagcc ccggcaacga cagcatcacc ttcttcttcg | 480 |
| actgcaactc cacggcggac gtcgtgctgc ggccgccgcc gtacatccgc ccgatcaact | 540 |
| gcagcagctt cgtcgacttc cagctgtggc cgtctttcgt cgcggcgcag cctgacgtgg | 600 |
| acgtgcgaga cgagagggca tggttgggg tgtgcaagga ggtggtggtg gcgccgctgc | 660 |
| tcaaggattt gctcgtgaac gaggagtact acggcaaatt gggcggcgat ggtggatacg | 720 |
| gcgcggtgct gaagcacggg ttccagctga gctgggaccc gacggcgggg atgtgccacg | 780 |
| agtgcgaggt atcccgggga cgctgcagct acgacgggaa caccacattc ctgggatgcc | 840 |
| tgtgctccga tggccacgtc agcaaaacag actgcggtga gttagtaccc tcttgcatac | 900 |
| atcaacatat ttaattacta gtattaccta gtattacttt cattccgaaa taaactaagg | 960 |
| taatacataa catcacatat cgtaattcta agaatttaga t | 1001 |

<210> SEQ ID NO 5
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: NB_LOC_Os02g52210

<400> SEQUENCE: 5

| attgattaat ccttccgtta tacactagaa tgaatcattt gcaacatctc ttagggcagt | 60 |
| cccagccctc catctaggat ggtgtctatg gcattaacta cattgccatg taggactttt | 120 |
| agtttatgtg gcactatatt aattgagaga gagtgaagag aggaagaaac tgggtctcat | 180 |
| gcaagacaca acttcaacac gagaacctat gcactagaca ctatcaagtt ttgcattggg | 240 |
| agagaattat caagttttgc attgggagag aatattgtct tcataataga taagaataa | 300 |
| atatgattgg tagagaagaa agatgatgta tttattaatg gtctaattta agaaagtatg | 360 |
| ggttgtagag tatagttttct attgtgatgt cttattgaca tggcaccata gacactactt | 420 |
| atggacacca taggttggga ctgcccttag tacctgttcc tttcaaagcg gctattgctt | 480 |

```
tgggcaactc ttttttgttt gttaataggt ttactggacg gctaaacgga gtatgtttta      540
tataaaaaat aaatttattt ttaagcttat attaattaat acctaattaa ttacgagcta      600
gattcacctt tgtttccgag cctgtaaccg ttgattcaag ctacatgtgg acttgctttt      660
tttagtggtt taactgttaa ccgtttctgg gtccgttaca gacctgacag gtagacacgt      720
agctgaaatc agaggagtcc aaggtccaaa tccaactggc atgcccagtc accacactgc      780
ttctgaacac ctggacggtt cgatcgtaca gtcaaacctg ccaaacagcg tatccacctg      840
gccggacagc ggaatccaca tcctcccgcg agacccggcg cgcgccacgc tatcgcgacg      900
ttctcgtcga tcgtcctcct cacaggtcac agctcacctc gacttgacca ctcctacacg      960 gcccttact atttagtacg actccgcacg ctgcatgcgc a                          1001
```

<210> SEQ ID NO 6
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: Koshi_LOC_Os02g52210

<400> SEQUENCE: 6

```
attgattaat ccttccgtta tacactagaa tgaatcattt gcaacatctc ttagggcagt       60
cccagccctc catctaggat ggtgtctatg gcattaacta cattgccatg taggacttttt     120 agtttatgtg gcactatatt aattgagaga gagtgaagag aggaagaaac tgggtctcat      180
gcaagacaca acttcaacac gagaacctat gcactagaca ctatcaagtt ttgcattggg      240
agagaattat caagttttgc attgggagag aatattgtct tcataataga taaagaataa      300
atatgattgg tagagaagaa agatgatgta tttattaatg gtctaattta agaaagtatg      360
ggttgtagag tatagtttct attgtgatgt cttattgaca tggcaccata gacactactt      420
atggacacca taggttggga ctgcccttag tacctgttcc tttcaaagcg gctattgctt      480
tgggcaactc ttttttgttt gttaataggt ttactggacg gctaaacgga gtatgtttta     540
tataaaaaat aaatttattt ttaagcttat attaattaat acctaattaa ttacgagcta      600
gattcacctt tgtttccgag cctgtaaccg ttgattcaag ctacatgtgg acttgctttt      660
tttagtggtt taactgttaa ccgtttctgg gtccgttaca gacctgacag gtagacacgt      720
agctgaaatc agaggagtcc aaggtccaaa tccaactggc atgcccagtc accacactgc      780
ttctgaacac ctggacggtt cgatcgtaca gtcaaacctg ccaaacagcg tatccacctg      840
gccggacagc ggaatccaca tcctcccgcg agacccggcg cgcgccacgc tatcgcgacg      900
ttctcgtcga tcgtcctcct cacaggtcac agctcacctc gacttgacca ctcctacacg      960 gcccttact atttagtacg actccgcacg ctgcatgcgc a                          1001
```

<210> SEQ ID NO 7
<211> LENGTH: 980
<212> TYPE: DNA
<213> ORGANISM: Oryza sativa
<220> FEATURE:
<221> NAME/KEY: promoter
<222> LOCATION: (1)..(980)
<223> OTHER INFORMATION: RP_Bio-226_LOC_Os02g52210

<400> SEQUENCE: 7

```
attgattaat ccttccgtta tacactagaa tgaatcattt gcaacatctc ttagggcagt       60
```

| | |
|---|---:|
| cccagccctc cacttaggat ggtgtctatg gcattaacta cattgccatg taggactttt | 120 |
| agtttatgtg gcactatatt aattaagaga gagagtgaag aaaggaagaa actgggtctc | 180 |
| atgcaagaca caacttcaac acgagaaact atgcactaga cactatcaag ttttgtattg | 240 |
| ggagagaata ttgtcttcat aatagataaa gaataaatat gattggtaga gaagaaagat | 300 |
| gatgtattta ttaatggtcc aatttaagaa agcatggggt gtagagtgta gtttctattg | 360 |
| tgatgtctta ttgacatggc accatagaca ctactatgg acaccatagg ttgggactgc | 420 |
| ccttaggacc tgttcctttc aaagcggcta ttgctttggg caactccttt gttgtttgtt | 480 |
| aataggttta ctggacggct aaacggagta tgttttatat aaaaaataaa tttatttta | 540 |
| agcttatatt aattaatacc taattaatta cgagctaatg attcacccttt gtttccgagc | 600 |
| ctgtaaccgt tgattcaagc tacatgtgga cttgcttttt ttagtggttt aactgttaac | 660 |
| cgtttctggg tccgttacag acctgacagg tagacacgta gctgaaatca gaggagtcca | 720 |
| aggtccaaat ccaactggca tacccagtca ccacactgct tctgaacacc tggacggttc | 780 |
| gatcgtacag tcaaacctgc caaacagcgt atccacctgg ccggacagcg aatccacat | 840 |
| cctcccgcga gacccggcgc gcgccacgct atcgcgacgt tctcgtcgat cgtcctcctc | 900 |
| acaggtcaca gctcacctcg acttgaccac tcctacacgg cccctttacta tttagtacga | 960 |
| ctccgcacgc tgcatgcgca | 980 |

<210> SEQ ID NO 8
<211> LENGTH: 980
<212> TYPE: DNA
<213> ORGANISM: Oryza sativa
<220> FEATURE:
<221> NAME/KEY: promoter
<222> LOCATION: (1)..(980)
<223> OTHER INFORMATION: Shuhui498_LOC_Os02g52210

<400> SEQUENCE: 8

| | |
|---|---:|
| attgattaat ccttccgtta tacactagaa tgaatcattt gcaacatctc ttagggcagt | 60 |
| cccagccctc cacttaggat ggtgtctatg gcattaacta cattgccatg taggactttt | 120 |
| agtttatgtg gcactatatt aattaagaga gagagtgaag aaaggaagaa actgggtctc | 180 |
| atgcaagaca caacttcaac acgagaaact atgcactaga cactatcaag ttttgtattg | 240 |
| ggagagaata ttgtcttcat aatagataaa gaataaatat gattggtaga gaagaaagat | 300 |
| gatgtattta ttaatggtcc aatttaagaa agcatggggt gtagagtgta gtttctattg | 360 |
| tgatgtctta ttgacatggc accatagaca ctactatgg acaccatagg ttgggactgc | 420 |
| ccttaggacc tgttcctttc aaagcggcta ttgctttggg caactccttt gttgtttgtt | 480 |
| aataggttta ctggacggct aaacggagta tgttttatat aaaaaataaa tttatttta | 540 |
| agcttatatt aattaatacc taattaatta cgagctaatg attcacccttt gtttccgagc | 600 |
| ctgtaaccgt tgattcaagc tacatgtgga cttgcttttt ttagtggttt aactgttaac | 660 |
| cgtttctggg tccgttacag acctgacagg tagacacgta gctgaaatca gaggagtcca | 720 |
| aggtccaaat ccaactggca tacccagtca ccacactgct tctgaacacc tggacggttc | 780 |
| gatcgtacag tcaaacctgc caaacagcgt atccacctgg ccggacagcg aatccacat | 840 |
| cctcccgcga gacccggcgc gcgccacgct atcgcgacgt tctcgtcgat cgtcctcctc | 900 |
| acaggtcaca gctcacctcg acttgaccac tcctacacgg cccctttacta tttagtacga | 960 |
| ctccgcacgc tgcatgcgca | 980 |

```
<210> SEQ ID NO 9
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: NB_LOC_Os05g38530

<400> SEQUENCE: 9
gcagaggttt tgtggcggag gtggcggggg tctagaacgt tcgcgcgcgg gcgatcctgg      60
ccgtcggatt gggggttctg aagggtcgg gagggtgccg gttcgcgtga aggaagagg      120 ggacaaccaa tcaggaggcg acacggtggg gacgcgttgg tgggccccgc ttgggcgcgc     180 gcttttgaa cggtctcttg aggtctggga ggttctacac tgtgctcgtg acgatggata     240
ggcggagtcg gtcctttgtt tccgaaaatc ctaattcgct aacgtgcgac cgcttgattt     300
ctcgcgaaca ctttccaaat tccaacctaa gggccccttt gaattggaga aaaaacatag    360
gaattttaga ggattttaat tctatagaaa aattttctat gaagtttttt gaaacaaagg    420
attgaatcct attaaatctt ttgaaatttc tatggaatgg ccaatcctat agagattttg    480
gaggaaattt agcaaaagct tcaatctctt agtaactttg agtctatctc tctcatctaa    540
ttcctgtgtt ttttctgcgg ttcaatcaaa cggccattcc tatgttttc ctctatttta     600 caatcatgtg ttttacactt acattccctat caaaatccta cgtttatca atcctgcgat    660 tcaaagaggc cataaataaa gacaagactc actagagatt atgggtaggg ttaggattttc   720 ggaggtaaag ggagatagag ccaggaggt gcatcgaatt tagagggatg gcaccgaagg     780 tcatgaaaa aggacagcgg cgagatacgcg atggcggcgc caagccgcg gggtcggcca     840 tgggccgtgg gccggtgttg gtggcgggg caaagctaaa cgaaataggg gaggaggaga     900
ccgaccgagc aggccccgcgc tgacaagttg acgccttcc ag tgccgacaa ggccgggtgg   960 tggcacggtc aggaggtggt ggtgggagaa ggttggagtc g                       1001

<210> SEQ ID NO 10
<211> LENGTH: 1001
<212> TYPE: DNA
<213> ORGANISM: Oryza sativa
<220> FEATURE:
<221> NAME/KEY: promoter
<222> LOCATION: (1)..(1001)
<223> OTHER INFORMATION: Koshi_LOC_Os05g38530

<400> SEQUENCE: 10
gcagaggttt tgtggcggag gtggcggggg tctagaacgt tcgcgcgcgg gcgatcctgg      60
ccgtcggatt gggggttctg aagggtcgg gagggtgccg gttcgcgtga aggaagagg      120 ggacaaccaa tcaggaggcg acacggtggg gacgcgttgg tgggccccgc ttgggcgcgc     180 gcttttgaa cggtctcttg aggtctggga ggttctacac tgtgctcgtg acgatggata     240
ggcggagtcg gtcctttgtt tccgaaaatc ctaattcgct aacgtgcgac cgcttgattt     300
ctcgcgaaca ctttccaaat tccaacctaa gggccccttt gaattggaga aaaaacatag    360
gaattttaga ggattttaat tctatagaaa aattttctat gaagtttttt gaaacaaagg    420
attgaatcct attaaatctt ttgaaatttc tatggaatgg ccaatcctat agagattttg    480
gaggaaattt agcaaaagct tcaatctctt agtaactttg agtctatctc tctcatctaa    540
ttcctgtgtt ttttctgcgg ttcaatcaaa cggccattcc tatgttttc ctctatttta     600 caatcatgtg ttttacactt acattccctat caaaatccta cgtttatca atcctgcgat    660
```

| | |
|---|---|
| tcaaagaggc cataaataaa gacaagactc actagagatt atgggtaggg ttaggatttc | 720 |
| ggaggtaaag ggagatagag ccagggaggt gcatcgaatt tagagggatg gcaccgaagg | 780 |
| tcatgaaaaa aggacagcgg cgagatagcg atggcggcgc caaagccgcg gggtcggcca | 840 |
| tgggccgtgg gccggtgttg gtggcggggg caaagctaaa cgaaataggg gaggaggaga | 900 |
| ccgaccgagc aggcccgcgc tgacaagttg acgcctttca gtgccgacaa ggccgggtgg | 960 |
| tggcacggtc aggaggtggt ggtgggagaa ggttggagtc g | 1001 |

```
<210> SEQ ID NO 11
<211> LENGTH: 985
<212> TYPE: DNA
<213> ORGANISM: Oryza sativa
<220> FEATURE:
<221> NAME/KEY: promoter
<222> LOCATION: (1)..(985)
<223> OTHER INFORMATION: RP_Bio-226_LOC_Os05g38530

<400> SEQUENCE: 11
```

| | |
|---|---|
| gcagaggttt tgtggcggag gtggcggggg tctagaacgt tcgcgcgctg gcgatcctgg | 60 |
| ccgtcggatt gggggttctg gaagggtcgg gagggtgccg gttcgcgtga aggaagagg | 120 |
| ggacaaccaa tcaggaggcg acacggtggg gacgcgttgg tgggccccgc ttgggcgcgc | 180 |
| gcttttgaa cggtctcttg aggtctggga ggttctacac tgtgctcgtg acgatggata | 240 |
| ggcggagtcg gtcctttgtt tccggaaatc ctaattcgct aacgtgcgac cgcttgattt | 300 |
| ctcgcgaaca ctttccaaat tccaacctaa gggccccttt gaattgaaga aaaaaatttt | 360 |
| atgaagtttt ttaaaacaaa ggattaaatc ctattaaatc ctttgaaatt cctatggaat | 420 |
| ggtcaatcct atagagattt tggaggaaat ttagcaaaag cttcaatctc ttagtaactt | 480 |
| tgagtctatc tctcttatct aattcctgtg ttttttctgc ggttcaatca aacgccatt | 540 |
| cctatgtttt tcctctattt tacaatcatg tgttttacac ttacattcct atcaaaatca | 600 |
| tacgttttat caatcctgcg attcaaagag accataaata aagacaagac taggccataa | 660 |
| aaaaagacaa gactcactag agattatgga tagggttagg atttcggagg taaagggaga | 720 |
| tagagccagg gaggtgcatc gagttttagg ggatggcacc gaaggtcatg aaaaaggac | 780 |
| atcggcgaga tagcgatggc ggcgccaaag ccgcggggtc ggccatgggc cgtgggccgg | 840 |
| tgttggtggc gggggcaaag ctaaacgaaa agagaggag gagaccgacc gagcgggccc | 900 |
| gcgctgacac gttgacgcct ttcagtgctg acaaggccgg gtggtggcac ggtcaggagg | 960 |
| tggtggtggg agaaggttgg agtcg | 985 |

```
<210> SEQ ID NO 12
<211> LENGTH: 985
<212> TYPE: DNA
<213> ORGANISM: Oryza sativa
<220> FEATURE:
<221> NAME/KEY: promoter
<222> LOCATION: (1)..(985)
<223> OTHER INFORMATION: Shuhui498_LOC_Os05g38530

<400> SEQUENCE: 12
```

| | |
|---|---|
| gcagaggttt tgtggcggag gtggcggggg tctagaacgt tcgcgcgctg gcgatcctgg | 60 |
| ccgtcggatt gggggttctg gaagggtcgg gagggtgccg gttcgcgtga aggaagagg | 120 |
| ggacaaccaa tcaggaggcg acacggtggg gacgcgttgg tgggccccgc ttgggcgcgc | 180 |
| gcttttgaa cggtctcttg aggtctggga ggttctacac tgtgctcgtg acgatggata | 240 |
| ggcggagtcg gtcctttgtt tccggaaatc ctaattcgct aacgtgcgac cgcttgattt | 300 |

```
ctcgcgaaca ctttccaaat tccaacctaa gggccccttt gaattgaaga aaaaaatttt    360
atgaagtttt ttaaaacaaa ggattaaatc ctattaaatc ctttgaaatt cctatggaat    420
ggtcaatcct atagagattt tggaggaaat ttagcaaaag cttcaatctc ttagtaactt    480
tgagtctatc tctcttatct aattcctgtg tttttctgc ggttcaatca aacggccatt     540
cctatgtttt tcctctattt tacaatcatg tgttttacac ttacattcct atcaaaatca    600
tacgttttat caatcctgcg attcaaagag accataaata aagacaagac taggccataa    660
aaaaagacaa gactcactag agattatgga tagggttagg atttcggagg taaagggaga    720
tagagccagg gaggtgcatc gagtttagag ggatggcacc gaaggtcatg aaaaaaggac    780
atcggcgaga tagcgatggc ggcgccaaag ccgcggggtc ggccatgggc cgtgggccgg    840
tgttggtggc gggggcaaag ctaaacgaaa agaggaggag gagaccgacc gagcgggccc    900
gcgctgacac gttgacgcct ttcagtgctg acaaggccgg gtggtggcac ggtcaggagg    960
tggtggtggg agaaggttgg agtcg                                         985
```

UNNATURAL PLANT SHOWING INDUCED GENE EXPRESSION AND METHOD FOR PRODUCING SAME

TECHNICAL FIELD

The present invention is broadly related to a field of plant improvement and breeding, and more particularly to a method of imparting disease resistance and stress resistance to agriculturally and horticulturally useful plants.

BACKGROUND ART

In recent years, an actual state of genetic trait control through chemical modification of DNA and chromatin without changing a base sequence of DNA is gradually becoming clear, and such research areas are rapidly developing as "epigenetics". Since it is known that epigenetic mutations such as changes in the methylation state of genomic DNA are inherited beyond sexual reproduction in plants, if epigenetic memory related to agriculturally useful stress tolerance is stably inherited, a powerful option for growing crops is probably provided (Non-Patent Document 1, Non-Patent Document 2).

However, for example, priming acquired by disease stress is not inherited by progeny plants and is lost by passage or subculture, no example of stable inheritance for two or more generations is known (Non-Patent Document 2). Recently, a method has been reported for producing a genetically stable epigenetic variant by utilizing the fact that an epigenetic state of a parent plant is maintained in plants reproduced asexually from somatic embryos (Non-Patent Document 3, Patent Document 1). This method is based on the premise of using a genetically modified plant in which a specific transcription factor (RWP-RK DOMAIN CONTAINING 4) is artificially and conditionally expressed in cells, and its use for breeding edible crops is significantly limited by legal regulation and public acceptance. Therefore, a method for producing a stress-tolerant plant using an epigenetic mutation and a method for enhancing a desirable trait of a plant have not yet been established in a manner applicable to breeding of a wide range of plants including food crops.

From a recent study, it has been clarified that when tissues of Arabidopsis and rice are differentiated on a medium containing an appropriate concentration of a phytohormone to form a callus and a plant is obtained by re-differentiating from the callus, the plant exhibits a methylation pattern of a genome different from the parent plant (Non-Patent Document 4). Additionally, it was pointed out that since the regenerated rice includes an individual exhibiting a phenotype different from the parent, epigenetic mutation is one of the causes of "somaclonal variation" recognized in regenerated plants.

In the process of clarifying the disease defense mechanism of plants, the present inventors accidentally found that demethylation occurs in a specific genomic region due to a process of dedifferentiation and redifferentiation of plants, and that a promoter region of a gene highly expressed in dedifferentiated cells is specifically demethylated in regenerated plants. As a result of intensive studies based on the finding, the present inventors found that by regenerating the dedifferentiated cell into a plant while highly expressing a specific gene, a change in the methylation state can be induced in the promoter of the specific gene, thereby completing the present invention.

CITATION LIST

Patent Literature

Patent Document 1: WO 2016/146552 A1
Patent Document 2: Japanese Laid-Open Patent Publication No. 03-280818
Patent Document 3: Japanese Laid-Open Patent Publication No. 06-141718
Patent Document 4: Japanese Laid-Open Patent Publication No. 2002-315572

Non Patent Literature

Non-Patent Document 1: Pieterse C M. (2012) Prime time for transgenerational defense. Plant Physiol. 158:545.

Non-Patent Document 2: Ramirez-Prado J S, Abulfaraj A A, Rayapuram N, Benhamed M, Hirt H. (2018) Plant Immunity: From Signaling to Epigenetic Control of Defense. Trends Plant Sci. 23:833-844.

Non-Patent Document 3: Wibowo A, Becker C, Durr J, Price J, Spaepen S, Hilton S, Putra H, Papareddy R, Saintain Q, Harvey S, Bending G D, Schulze-Lefert P, Weigel D, Gutierrez-Marcos J. (2018) Partial maintenance of organ-specific epigenetic marks during plant asexual reproduction leads to heritable phenotypic variation. Proc Natl Acad Sci USA. 115:E9145-E9152.

Non-Patent Document 4: Jiang C, Mithani A, Gan X, Belfield E J, Klingler J P, Zhu J K, Ragoussis J, Mott R, Harberd N P. (2011) Regenerant Arabidopsis lineages display a distinct genome-wide spectrum of mutations conferring variant phenotypes. Curr Biol. 21:1385-1390.

Non-Patent Document 5: Tsuji, G., N. Fujihara, C. Hirose, S. Tsuge, T. Shiraishi, and Y. Kubo. 2003. Agrobacterium tumefaciens-mediated transformation for random insertional mutagenesis in Colletotrichum lagenarium. J. Gen. Plant Pathol. 69: 230-239.

Non-Patent Document 6: Nagashima, K., Kasai, M., Nagata, S. and Kaziro, Y.: Structure of the two genes for the polypeptide chain elongation factor 1a (EF-I~) from Saccharomyces cerevisiae. Gene 45 (1986) 265-273.

Non-Patent Document 7: Tosa Y, Hirata K, Tamba H, Nakagawa S, Chuma I, Isobe C, Osue J, Urashima A S, Don L D, Kusaba M, Nakayashiki H, Tanaka A, Tani T, Mori N, Mayama S. Genetic Constitution and Pathogenicity of Lolium Isolates of Magnaporthe oryzae in Comparison with Host Species-Specific Pathotypes of the Blast Fungus. Phytopathology (2004) 94:454-462.

Non-Patent Document 8: Kaoru Mori, Mitsuo Nakajima, Effect of Light on Sporulation of rice blast fungus, Japanese Journal of Phytopathology (1970) 36: 319-324

Non-Patent Document 9: Blackhall N W, Jotham J P, Azhakanandam K, Power J B, Lowe K C, Cocking E C, Davey M R. Callus initiation, maintenance, and shoot induction in rice. Methods MolBiol. 1999; 111:19-29. Review.

Non-Patent Document 10: Takatsuji H. Development of disease-resistant rice using regulatory components of induced disease resistance. Front Plant Sci. 2014 Nov. 13; 5:630. doi: 10.3389/fpls.2014.00630. eCollection 2014. Review.

Non-Patent Document 11: Conesa A, Madrigal P, Tarazona S, Gomez-Cabrero D, Cervera A, McPherson A, Szcesniak M W, Gaffney D J, Elo L L, Zhang X, Mortazavi A. A survey of best practices for RNA-seq data analysis. Genome Biol. 2016 Jan. 26; 17:13. doi:10.1186/s13059-016-0881-8. Review. Erratum in: Genome Biol. 2016; 17(1): 181.3

Non-Patent Document 12: Krueger F, Andrews S R. (2011) Bismark: a flexible aligner and methylation caller for Bisulfite-Seq applications. Bioinformatics 27:1571-1572.

Non-Patent Document 13: Thorvaldsdo'ttir H, Robinson J T, Mesirov J P (2013) Integrative Genomics Viewer (IGV): high-performance genomics data visualization and exploration. Brief Bioinform. 14:178-192.

Non-Patent Document 14: Robledo-Paz A, Vazquez-Sanchez M N, Adame-Alvarez R M, Jofre-Garfias A E. Callus and suspension culture induction, maintenance, and characterization. Methods Mol Biol. 2006; 318:59-70.

Non-Patent Document 15: Yang Y W, Chen H C, Jen W F, Liu L Y, Chang M C. Comparative Transcriptome Analysis of Shoots and Roots of TNG67 and TCN1 Rice Seedlings under Cold Stress and Following Subsequent Recovery: Insights into Metabolic Pathways, Phytohormones, and Transcription Factors. PLoS One. 2015 Jul. 2; 10(7): e0131391.

Non-Patent Document 16: Magome H, Yamaguchi S, Hanada A, Kamiya Y, Oda K. (2008) The DDF1 transcriptional activator upregulates expression of a gibberellin-deactivating gene, GA2ox7, under high-salinity stress in *Arabidopsis*. Plant J. 56:613-26.

Non-Patent Document 17: Krishnamurthy P, Mohanty B, Wijaya E, Lee D Y, Lim T M, Lin Q, Xu J, Loh C S, Kumar P P. (2017) Transcriptomics analysis of salt stress tolerance in the roots of the mangrove *Avicennia officinalis*. Sci Rep. 7:10031.

Non-Patent Document 18: Zhou Y, Yang, Cui F, Zhang F, Luo X, Xie J. (2016) Transcriptome Analysis of Salt Stress Responsiveness in the Seedlings of Dongxiang Wild Rice (*Oryza rufipogon* Griff.) PLoS One. 11:e0146242.

Non-Patent Document 19: Baldoni E, Bagnaresi P, Locatelli F, Mattana M, Genga A. (2016) Comparative Leaf and Root Transcriptomic Analysis of two Rice *Japonica* Cultivars Reveals Major Differences in the Root Early Response to Osmotic Stress. Rice (NY). 9:25.

Non-Patent Document 20: Iwai T, Seo S, Mitsuhara I, Ohashi Y. Probenazole-induced accumulation of salicylic acid confers resistance to *Magnaporthe grisea* in adult rice plants. Plant Cell Physiol. 2007 July; 48(7):915-24.

Non-Patent Document 21: Bektas Y, Eulgem T. Synthetic plant defense elicitors. Front Plant Sci. 2015 Jan. 26; 5:804. doi: 10.3389/fpls.2014.00804. eCollection 2014. Review.

Non-Patent Document 22: Shimono M, Sugano S, Nakayama A, Jiang C J, Ono K, Toki S, Takatsuji H. Rice WRKY45 plays a crucial role in benzothiadiazole-inducible blast resistance. Plant Cell. 2007 June; 19(6):2064-76.

Non-Patent Document 23: Yasuda M. Regulation mechanisms of systemic acquired resistance induced by plant activators, J. Pestic. Sci. 2007 Volume 32, Issue 3, Pages 281-282, Released Aug. 27, 2007, Online ISSN 1349-0923, Print ISSN 1348-589X, https://doi.org/10.1584/jpestics.32.281

SUMMARY OF INVENTION

Technical Problem

A problem to be solved by the present invention is to provide a non-natural plant in which expression of a gene of interest is induced and a method for producing the same. Particularly, the present invention relates to a non-natural plant in which the expression of the gene is stably induced even in the absence of a stimulus inducing the expression of the gene, and a method for producing the same. When the induction of the expression of the gene enhances a trait of interest of a plant of interest, the present invention provides a non-natural plant in which the trait is enhanced and a method for producing the same.

Another problem to be solved by the present invention is to provide a non-natural plant in which a change in methylation state such as demethylation is artificially induced in a promoter of a gene of interest. By inducing a change in methylation state in the promoter of the gene of interest, the expression of the gene is induced and the trait of interest of the plant of interest is enhanced.

Solution to Problem

The present invention has the following configurations.
[Aspect 1]
A method for producing a non-natural plant in which expression of a gene is induced, comprising the steps of:
(1) providing a portion of a plant;
(2) culturing the portion of the plant under dedifferentiation-inducing conditions to form a callus;
(3) culturing the callus under redifferentiation-inducing conditions to form a shoot;
(A) providing a stimulus to the callus, wherein the stimulus is a stimulus not reducing the survival rate of the callus to 90% or less, 91% or less, 92% or less, 93% or less, 94% or less, preferably 95% or less, 96% or less, 97% or less, 98% or less, 99% or less, most preferably 100% or less, as compared to a control to which the stimulus is not provided; and
(4) culturing the shoot to obtain a non-natural plant in which the expression of the gene is induced in the absence of the stimulus, wherein
steps (1), (2), (3), and (4) are performed in the order of (1), (2), (3), and (4), and step (A) is performed in either or both of steps (2) and (3), and wherein
in step (2) or (3), the callus is not selected by using a resistance to the stimulus as an index.
[Aspect 2]
The method according to aspect 1, wherein the stimulus is a stimulus inducing the expression of the gene in the callus, and wherein
the induction of the expression of the gene in the non-natural plant enhances a trait of interest of the plant.
[Aspect 3]
The method according to aspect 1, wherein the following step is performed after the step (3) and before the step (4), or in the step (4):
(B) a step of confirming that the expression of the gene is induced in the absence of the stimulus, or the trait is enhanced, in the plant obtained by culturing the shoot.
[Aspect 4]
A method for producing a seed of a non-natural plant in which expression of a gene is induced, comprising:
steps (1), (2), (3), (A), and (4) of the method according to aspect 1; and
(5) a step of obtaining a seed from a non-natural plant obtained by culturing the shoot, wherein
steps (1), (2), (3), (4), and (5) are performed in the order of (1), (2), (3), (4), and (5), and step (A) is performed in either or both of steps (2) and (3), and wherein
a plant obtained by germinating the seed is a non-natural plant in which the expression of the gene is induced in the absence of the stimulus.

[Aspect 5]
The method according to aspect 4, wherein the following step is performed after the step (5):
(C) a step of confirming that the expression of the gene is induced, or a trait of interest is enhanced, in the absence of the stimulus in the plant obtained by germinating the seed.

[Aspect 6]
A method of producing a non-natural plant in which expression of a gene is induced, comprising:
steps (1), (2), (3), (A), and (4) of the method according to aspect 1; and
(6) a step of vegetatively propagating the non-natural plant obtained in step (4) to obtain a non-natural plant in which the expression of the gene is induced in the absence of the stimulus, wherein
steps (1), (2), (3), (4), and (6) are performed in the order of (1), (2), (3), (4), and (6), and step (A) is performed in either or both of steps (2) and (3), and wherein in step (2) or (3), the callus is not selected by using a resistance to the stimulus as an index.

[Aspect 7]
A method of producing a non-natural plant in which expression of a gene is induced, comprising:
a step of vegetatively propagating the non-natural plant obtained by the method of aspect 1 or a non-natural plant obtained by germinating the seed obtained by the method of aspect 4 to obtain a non-natural plant in which the expression of the gene is induced in the absence of the stimulus.

[Aspect 8]
The method according to any one of aspects 1 to 6, wherein the gene is not expressed in the absence of the stimulus in the callus formed from a portion of the plant.

[Aspect 9]
The method according to any one of aspects 1 to 8, wherein the culture under the dedifferentiation-inducing conditions is performed on or in a medium containing 2,4-Dichlorophenoxyacetic acid (2,4-D), indole-3-acetic acid (IAA), 6-benzylaminopurine (6-BA), or trans-zeatin (t-zeatin).

[Aspect 10]
The method according to any one of aspects 1 to 9, wherein the culture under the redifferentiation-inducing conditions is performed on or in a medium containing kinetin, IAA, 6-BA, t-zeatin, or 1-Naphthaleneacetic acid (NAA).

[Aspect 11]
The method according to any one of aspects 1 to 10, wherein the trait is a resistance to the stimulus.

[Aspect 12]
The method according to aspect 11, wherein the stimulus is a low-temperature treatment, and wherein the trait is a low-temperature resistance.

[Aspect 13]
The method according to any one of aspects 1 to 10, wherein the trait is not a resistance to the stimulus.

[Aspect 14]
The method according to aspect 13, wherein the stimulus is a treatment with a resistance inducer activating a salicylic acid pathway, and wherein the trait is a resistance to a pathogen.

[Aspect 15]
The method according to aspect 14, wherein the resistance inducer activating a salicylic acid pathway is probenazole (3-prop-2-enoxy-1,2-benzothiazole 1,1-dioxide).

[Aspect 16]
The method according to aspect 11, wherein the stimulus is treatment with salt, and wherein the trait is a salt resistance.

[Aspect 17]
The method according to any one of aspects 1 to 16, wherein the plant is rice (*Oryza sativa*) of the Poaceae family.

[Aspect 18]
The method according to any one of aspects 1 to 16, wherein the plant is tobacco of the Solanaceae family.

[Aspect 19]
The method according to any one of aspects 1 to 16, wherein the plant is rice (*Oryza sativa*) of the Poaceae family, and wherein the pathogen is *Magnaporthe oryzae* or *Xanthomonas oryzae* pv. *oryzae*.

[Aspect 20]
The method according to any one of aspects 1 to 16, wherein the plant is tobacco of the Solanaceae family and the pathogen is *Botrytis cinerea* or *Pseudomonas syringae* pv. *tabaci*.

[Aspect 21]
The method according to any one of aspects 1 to 20, wherein a step of gene recombination or a step of expressing a gene from a foreign vector is not included.

[Aspect 22]
Non-natural rice (*Oryza sativa*) of the Poaceae family with a demethylated promoter region up to 1 kb upstream from the transcription start site of at least one gene selected from the following table:

TABLE 1A

| Locus | Description | Family | Function | Log2 (Fold Change) | False Discovery Rate (FDR) |
|---|---|---|---|---|---|
| LOC_Os03g03700 | MLO domain containing protein, putative, expressed | MLO | disease resistance | 0.91806555 | 1.069E-09 |
| LOC_Os05g34550 | MLO domain containing protein, putative, expressed | MLO | disease resistance | 1.804133277 | 4.53E-09 |
| LOC_Os05g40770 | leucine-rich repeat family protein, putative, expressed | NBS-LRR | disease resistance | 2.0474062 | 0 |
| LOC_Os12g17430 | NBS-LRR disease resistance protein, putative, expressed | NBS-LRR | disease resistance | 2.559228902 | 0 |
| LOC_Os11g11940 | MLA10, putative, expressed | NBS-LRR | disease resistance | 8.156455381 | 2.01595E-62 |
| LOC_Os11g11920 | resistance protein, putative, expressed | NBS-LRR | disease resistance | 5.694929093 | 3.29408E-55 |
| LOC_Os11g45790 | NB-ARC domain containing protein, expressed | NBS-LRR | disease resistance | 1.212996498 | 8.497E-11 |
| LOC_Os11g11810 | NBS-LRR disease resistance protein, putative, expressed | NBS-LRR | disease resistance | 1.979314963 | 4.75774E-10 |
| LOC_Os09g34150 | NBS-LRR disease resistance protein, putative, expressed | NBS-LRR | disease resistance | 1.818440145 | 4.932E-10 |
| LOC_Os11g12000 | NBS-LRR disease resistance protein, putative, expressed | NBS-LRR | disease resistance | 1.661519425 | 6.90262E-08 |
| LOC_Os01g70080 | NB-ARC domain containing protein, expressed | NBS-LRR | disease resistance | 1.19000778 | 8.616E-08 |
| LOC_Os04g53050 | disease resistance protein RPP13-like protein 1, putative, expressed | NBS-LRR | disease resistance | 2.296507315 | 1.401E-07 |
| LOC_Os07g17220 | disease resistance protein, putative, expressed | NBS-LRR | disease resistance | 1.36843796 | 0.000000178 |
| LOC_Os11g11960 | disease resistance protein RPM1, putative, expressed | NBS-LRR | disease resistance | 1.497811361 | 7.17623E-07 |
| LOC_Os12g39620 | disease resistance protein, putative, expressed | NBS-LRR | disease resistance | 0.431971299 | 0.003476 |
| LOC_Os07g17250 | disease resistance protein RPP13-like protein 1, putative, expressed | NBS-LRR | disease resistance | 0.798196081 | 0.008649897 |
| LOC_Os09g09490 | disease resistance protein RPM1, putative, expressed | NBS-LRR | disease resistance | 1.062401718 | 0.014666544 |
| LOC_Os01g06790 | disease resistance protein, putative, expressed | NBS-LRR | disease resistance | 1.315004853 | 0.025875773 |
| LOC_Os12g36730 | stripe rust resistance protein Yr10, putative, expressed | NBS-LRR | disease resistance | 0.648391253 | 0.045823429 |
| LOC_Os05g35290 | phenylalanine ammonia-lyase, putative, expressed | PAL | disease resistance | 1.696280537 | 0 |
| LOC_Os02g41680 | phenylalanine ammonia-lyase, putative, expressed | PAL | disease resistance | 1.716487221 | 0 |
| LOC_Os06g11240 | 12-oxophytodienoate reductase, putative, expressed | jasmonate | jasmonate pathway | 9.109643384 | 2.59039E-23 |
| LOC_Os08g35740 | 12-oxophytodienoate reductase, putative, expressed | jasmonate | jasmonate pathway | 0.694770685 | 0.00002108 |
| LOC_Os01g08320 | ZIM domain containing protein, putative, expressed | JAZ | jasmonate pathway | 1.521730939 | 0 |
| LOC_Os03g28940 | ZIM domain containing protein, putative, expressed | JAZ | jasmonate pathway | 1.565185717 | 0 |
| LOC_Os10g25290 | ZIM domain containing protein, putative, expressed | JAZ | jasmonate pathway | 0.424742104 | 7.54E-03 |
| LOC_Os03g05470 | tyrosine protein kinase domain containing protein, putative, expressed | kinase | kinase | 1.078999917 | 4.808E-09 |
| LOC_Os07g08860 | S-domain receptor-like protein kinase, putative, expressed | kinase | kinase | 2.828607931 | 1.14752E-07 |
| LOC_Os11g17380 | protein kinase domain containing protein, expressed | kinase | kinase | 3.938534192 | 1.31571E-07 |
| LOC_Os11g35274 | protein kinase domain containing protein, expressed | kinase | kinase | 6.789323412 | 1.89022E-05 |
| LOC_Os05g47770 | serine/threonine-protein kinase At1g18390 precursor, putative, expressed | kinase | kinase | 1.318834104 | 0.016859398 |
| LOC_Os11g48000 | S-locus-like receptor protein kinase, putative, expressed | kinase | kinase | 1.277486828 | 0.019250943 |
| LOC_Os10g04720 | TKL_IRAK_DUF26-la.5-DUF26 kinases have homology to DUF26 containing loci, expressed | kinase | kinase | 0.900236238 | 0.032972631 |
| LOC_Os10g33040 | receptor-like protein kinase precursor, putative, expressed | receptor-kinase | receptor | 1.52808439 | 0 |
| LOC_Os10g01100 | receptor-like protein kinase, putative, expressed | receptor-kinase | receptor | 1.791670605 | 0 |
| LOC_Os01g53920 | receptor-like protein kinase 5 precursor, putative, expressed | receptor-kinase | receptor | 2.070360813 | 0 |
| LOC_Os03g62180 | lectin protein kinase family protein, putative, expressed | receptor-kinase | receptor | 2.289855738 | 0 |
| LOC_Os04g52600 | SHR5-receptor-like kinase, putative, expressed | receptor-kinase | receptor | 1.15290639 | 2.88E-15 |
| LOC_Os08g28710 | receptor protein kinase CRINKLY4 precursor, putative, expressed | receptor-kinase | receptor | 2.090310741 | 7.39E-11 |
| LOC_Os04g42480 | receptor-like protein kinase At3g46290 precursor, putative, expressed | receptor-kinase | receptor | 0.603080231 | 1.30E-03 |
| LOC_Os05g34270 | inactive receptor kinase At1g27190 precursor, putative, expressed | receptor-kinase | receptor | 0.459827691 | 0.002056 |
| LOC_Os08g24310 | receptor-like protein kinase precursor, putative, expressed | receptor-kinase | receptor | 1.339326888 | 0.010213701 |
| LOC_Os11g07200 | receptor protein kinase CLAVATA1 precursor, putative, expressed | receptor-kinase | receptor | 2.63641767 | 0 |
| LOC_Os11g47240 | leucine-rich repeat receptor protein kinase EXS precursor, putative, expressed | receptor-kinase | receptor | 2.843523488 | 0 |
| LOC_Os11g40810 | receptor kinase, putative, expressed | receptor-kinase | receptor | 1.515113847 | 9.75161E-06 |
| LOC_Os01g66820 | inactive receptor kinase At1g27190 precursor, putative, expressed | receptor-kinase | receptor | 0.971088909 | 0.011384797 |
| LOC_Os11g46900 | wall-associated receptor kinase 3 precursor, putative, expressed | receptor-kinase | receptor | 2.309778271 | 0.012274052 |
| LOC_Os11g47000 | receptor-like protein kinase precursor, putative, expressed | receptor-kinase | receptor | 2.007254099 | 0.022437256 |

TABLE 1A-continued

| Locus | Description | Family | Function | Log2 (Fold Change) | False Discovery Rate (FDR) |
|---|---|---|---|---|---|
| LOC_Os08g34640 | receptor-like protein kinase precursor, putative, expressed | receptor-kinase | receptor | 1.07919888 | 0.043983106 |
| LOC_Os08g36920 | AP2 domain containing protein, expressed | AP2/ERF | transcription | 1.933152337 | 0 |
| LOC_Os02g52670 | AP2 domain containing protein, expressed | AP2/ERF | transcription | 2.412168528 | 6.296E-09 |
| LOC_Os01g01870 | helix-loop-helix DNA-binding domain containing protein, expressed | HLH | transcription | 1.286268255 | 0 |
| LOC_Os04g23550 | basic helix-loop-helix family protein, putative, expressed | HLH | transcription | 0.816309834 | 3.66E-09 |
| LOC_Os06g09370 | PTF1, putative, expressed | HLH | transcription | 0.715693416 | 0.000005127 |
| LOC_Os05g48010 | MYB family transcription factor, putative, expressed | MYB | transcription | 1.095365036 | 3.33E-04 |
| LOC_Os07g25150 | myb-related protein 306, putative, expressed | MYB | transcription | 1.307161348 | 0.004363 |
| LOC_Os10g41200 | MYB family transcription factor, putative, expressed | MYB | transcription | 0.412382181 | 0.037287571 |
| LOC_Os09g16510 | WRKY74, expressed | WRKY | transcription | 3.891524015 | 0 |
| LOC_Os05g39720 | WRKY70, expressed | WRKY | transcription | 5.493377384 | 0 |
| LOC_Os01g51690 | WRKY26, expressed | WRKY | transcription | 4.340255694 | 6.13E-05 |
| LOC_Os02g08440 | WRKY71, expressed | WRKY | transcription | 0.441953185 | 0.002117 |
| LOC_Os05g27730 | WRKY53, expressed | WRKY | transcription | 0.319641543 | 0.041084028 |

[Aspect 23]

Non-natural rice (*Oryza sativa*) of the Poaceae family with a demethylated promoter region up to 1 kb upstream from the transcription start site of at least one gene selected from the following table:

TABLE 2A

| Locus | Description | Family | Log2 (Fold Change) | False Discovery Rate (FDR) |
|---|---|---|---|---|
| LOC_Os10g41330 | AP2 domain containing protein, expressed | AP2/ERF | 2.495462871 | 8.08682E−06 |
| LOC_Os09g35020 | AP2 domain containing protein, expressed | AP2/ERF | 2.523131008 | 0.000686133 |
| LOC_Os02g54050 | ethylene-responsive transcription factor, putative, expressed | AP2/ERF | 3.060245005 | 0.023048092 |
| LOC_Os03g09170 | ethylene-responsive transcription factor, putative, expressed | AP2/ERF | 1.665544551 | 0.038830523 |
| LOC_Os09g35010 | dehydration-responsive element-binding protein, putative, expressed | DREB | 2.211648865 | 0.000686133 |
| LOC_Os04g43680 | MYB family transcription factor, putative, expressed | MYB | 1.901424957 | 0.0164998 |
| LOC_Os01g61080 | WRKY24, expressed | WRKY | 1.768823852 | 0.006293567 |
| LOC_Os01g60640 | WRKY21, expressed | WRKY | 1.628985483 | 0.006809766 |
| LOC_Os01g60600 | WRKY108, expressed | WRKY | 1.836701646 | 0.048385624 |
| LOC_Os02g52210 | zinc finger, C3HC4 type domain containing protein, expressed | zinc finger | 1.600996568 | 0.007817755 |
| LOC_Os03g32230 | ZOS3-12-C2H2 zinc finger protein, expressed | zinc finger | 3.536782648 | 0.027821004 |

[Aspect 24]

Non-natural rice (*Oryza sativa*) of the Poaceae family with a demethylated promoter region up to 1 kb upstream from the transcription start site of at least one gene selected from the following table:

TABLE 3A

| Locus | Description | Family | Function | Log2(Fold Change) | False Discovery Rate (FDR) |
|---|---|---|---|---|---|
| LOC_Os03g05290 | aquaporin protein, putative, expressed | aquaporin | channel | 2.024753679 | 1.31796E-10 |
| LOC_Os02g41860 | aquaporin protein, putative, expressed | aquaporin | channel | 1.074418295 | 0.014634199 |
| LOC_Os01g55240 | gibberellin 2-beta-dioxygenase, putative, expressed | GA | GA catalysis | 1.994052883 | 1.23487E-09 |
| LOC_Os05g43880 | gibberellin 2-beta-dioxygenase, putative, expressed | GA | GA catalysis | 2.876048642 | 1.28408E-07 |
| LOC_Os05g48700 | gibberellin 2-beta-dioxygenase, putative, expressed | GA | GA catalysis | 4.31372693 | 0.034823033 |
| LOC_Os03g63970 | gibberellin 20 oxidase 1, putative, expressed | GA | GA synthesis | 1.139386421 | 0.001443469 |
| LOC_Os05g34854 | gibberellin 20 oxidase 2, putative, expressed | GA | GA synthesis | 3.228952838 | 0.01092428 |
| LOC_Os08g39140 | heat shock protein, putative, expressed | HSP | HSP | 2.5341 7903 | 9.58777E-18 |
| LOC_Os03g16860 | DnaK family protein, putative, expressed | HSP | HSP | 2.443523257 | 2.65268E-10 |
| LOC_Os05g38530 | DnaK family protein, putative, expressed | HSP | HSP | 2.909434916 | 8.5631 7E-07 |
| LOC_Os02g02410 | DnaK family protein, putative, expressed | HSP | HSP | 1.300649611 | 7.26631E-05 |
| LOC_Os06g50300 | heat shock protein, putative, expressed | HSP | HSP | 1.339868092 | 9.75751E-05 |
| LOC_Os09g29840 | heat shock protein, putative, expressed | HSP | HSP | 1.122315862 | 0.000291108 |
| LOC_Os07g33350 | hsp20/alpha crystallin family protein, putative, expressed | HSP | HSP | 1.094013967 | 0.001950869 |
| LOC_Os01g62290 | DnaK family protein, putative, expressed | HSP | HSP | 2.129927883 | 0.003813366 |
| LOC_Os05g09480 | OsIAA16-Auxin-responsive Aux/IAA gene family member, expressed | IAA | IAA | 1.215688111 | 0.000709516 |
| LOC_Os12g40900 | OsIAA31-Auxin-responsive Aux/IAA gene family member, expressed | IAA | IAA | 1.169698347 | 0.015037338 |
| LOC_Os02g08420 | cinnamoyl CoA reductase, putative, expressed | CCR | lignin | 1.800642605 | 7.06719E-07 |
| LOC_Os08g34280 | cinnamoyl-CoA reductase, putative, expressed | CCR | lignin | 1.289392472 | 0.001027591 |
| LOC_Os08g17500 | cinnamoyl-CoA reductase, putative, expressed | CCR | lignin | 3.602806974 | 0.016992347 |
| LOC_Os03g17700 | CGMC_MAPKCGMC_2_ERK 2-CGMC includes CDA, MAPK, GSK3, and CLKC kinases, expressed | MAPK | MAPK | 1.375236023 | 0.023803542 |
| LOC_Os03g12390 | STE_MEK_ste7_MAP2K.6-STE kinases include homologs to sterile 7, sterile 11 and sterile 20 from yeast, expressed | MAPKK | MAPK | 1.207916647 | 0.000590415 |
| LOC_Os10g38780 | glutathione S-transferase, putative, expressed | GST | redox | 2.075340048 | 1.18698E-11 |
| LOC_Os10g38700 | glutathione S-transferase, putative, expressed | GST | redox | 1.228195201 | 0.000201768 |
| LOC_Os09g36080 | cytochrome P450, putative, expressed | P450 | redox | 2.405290454 | 8.6067E-08 |
| LOC_Os02g17760 | cytochrome P450, putative, expressed | P450 | redox | 1.252006314 | 0.000174468 |
| LOC_Os12g16720 | cytochrome P450 71A1, putative, expressed | P450 | redox | 1.592637583 | 0.017923544 |
| LOC_Os02g30080 | cytochrome P450, putative, expressed | P450 | redox | 4.518083384 | 0.018840286 |
| LOC_Os02g29960 | cytochrome P450, putative, expressed | P450 | redox | 1.040847196 | 0.041346184 |
| LOC_Os03g29150 | cytochrome P450 72A1, putative, expressed | P450 | redox | 1 205214229 | 0.043337557 |
| LOC_Os09g11480 | AP2 domain containing protein, expressed | AP2/ERF | transcription | 5.407322362 | 4.88552E-51 |
| LOC_Os09g11460 | AP2 domain containing protein, expressed | AP2/ERF | transcription | 2.860608254 | 2.27517E-17 |
| LOC_Os05g25260 | AP2 domain containing protein, expressed | AP2/ERF | transcription | 1.968076755 | 1.13995E-09 |
| LOC_Os06g10780 | AP2 domain containing protein, expressed | AP2/ERF | transcription | 5.120436599 | 3.9151E-06 |
| LOC_Os09g35020 | AP2 domain containing protein, expressed | AP2/ERF | transcription | 3.411924479 | 1.09183E-05 |
| LOC_Os04g52090 | AP2 domain containing protein, expressed | AP2/ERF | transcription | 1.545850931 | 6.9816E-05 |
| LOC_Os03g08500 | AP2 domain containing protein, expressed | AP2/ERF | transcription | 1.514169473 | 7.44042E-05 |
| LOC_Os05g41780 | AP2 domain containing protein, expressed | AP2/ERF | transcription | 1.490120325 | 0.00010539 |
| LOC_Os02g52670 | AP2 domain containing protein, expressed | AP2/ERF | transcription | 2.2736376 | 0.002530082 |
| LOC_Os10g41130 | AP2 domain containing protein, expressed | AP2/ERF | transcription | 1.460696529 | 0.022874248 |
| LOC_Os06g03670 | dehydration-responsive element-binding protein, putative, expressed | DREB | transcription | 2.733016984 | 0.000156813 |
| LOC_Os10g35010 | dehydration-responsive element-binding protein, putative, expressed | DREB | transcription | 2.167447548 | 0.001345484 |
| LOC_Os10g41230 | homeobox associated leucine zipper, putative, expressed | HAL | transcription | 1.977733758 | 3.03411E-10 |
| LOC_Os03g12860 | homeobox associated leucine zipper, putative, expressed | HAL | transcription | 1.573082771 | 1.03157E-05 |
| LOC_Os01g50940 | helix-loop-helix DNA-binding domain containing protein, expressed | HLH | transcription | 2.648188445 | 7.03259E-06 |
| LOC_Os01g67480 | helix-loop-helix DNA-binding domain containing protein, expressed | HLH | transcription | 1.343322415 | 1.84407E-05 |
| LOC_Os01g01870 | helix-loop-helix DNA-binding domain containing protein, expressed | HLH | transcription | 1.322130056 | 0.000173637 |

TABLE 3A-continued

| Locus | Description | Family | Function | Log2(Fold Change) | False Discovery Rate (FDR) |
|---|---|---|---|---|---|
| LOC_Os03g59670 | basic helix-loop-helix, putative, expressed | HLH | transcription | 1.325023349 | 0.004846951 |
| LOC_Os02g09480 | myb-like DNA-binding domain containing protein, putative, expressed | MYB | transcription | 2.30949919 | 3.2867E-11 |
| LOC_Os05g35500 | MYB family transcription factor, putative, expressed | MYB | transcription | 1.943296495 | 9.3337E-06 |
| LOC_Os01g65370 | MYB family transcription factor, putative, expressed | MYB | transcription | 1.687881277 | 1.91322E-05 |
| LOC_Os03g20090 | MYB family transcription factor, putative, expressed | MYB | transcription | 1.829099819 | 2.07872E-05 |
| LOC_Os10g33810 | myb-related protein Myb4, putative, expressed | MYB | transcription | 2.686870662 | 0.000243873 |
| LOC_Os01g44390 | MYB family transcription factor, putative, expressed | MYB | transcription | 1.360259228 | 0.002792814 |
| LOC_Os01g64360 | MYB family transcription factor, putative, expressed | MYB | transcription | 1.914872011 | 0.011252502 |
| LOC_Os07g43580 | MYB family transcription factor, putative, expressed | MYB | transcription | 1.008748219 | 0.018664073 |
| LOC_Os07g31470 | MYB family transcription factor, putative, expressed | MYB | transcription | 2.159246428 | 0.049581406 |
| LOC_Os07g12340 | NAC domain-containing protein 67, putative, expressed | NAC | transcription | 2.470385865 | 7.14208E-13 |
| LOC_Os03g60080 | NAC domain-containing protein 67, putative, expressed | NAC | transcription | 1.546832043 | 0.001540376 |
| LOC_Os12g29330 | no apical meristem protein, putative, expressed | NAM | transcription | 1.29240949 | 0.000597935 |
| LOC_Os11g05614 | no apical meristem protein, putative, expressed | NAM | transcription | 3.0554299 | 0.00493077 |
| LOC_Os01g48446 | no apical meristem protein, putative, expressed | NAM | transcription | 1.145052228 | 0.026238701 |
| LOC_Os11g07460 | TCP family transcription factor, putative, expressed | TCP | transcription | 1.933214117 | 2.88689E-05 |
| LOC_Os08g43160 | TCP family transcription factor, putative, expressed | TCP | transcription | 1.074354162 | 0.002767846 |
| LOC_Os05g43760 | TCP family transcription factor, putative, expressed | TCP | transcription | 1.316439867 | 0.021691727 |
| LOC_Os08g29660 | WRKY69, expressed | WRKY | transcription | 1.827439568 | 1.67662E-07 |
| LOC_Os01g09100 | WRKY10, expressed | WRKY | transcription | 2.590376344 | 1.64311E-06 |
| LOC_Os05g27730 | WRKY53, expressed | WRKY | transcription | 1.552273087 | 6.70903E-05 |
| LOC_Os09g16510 | WRKY74, expressed | WRKY | transcription | 1.226349227 | 0.000866222 |
| LOC_Os01g60600 | WRKY108 expressed | WRKY | transcription | 2.189361405 | 0.002772143 |
| LOC_Os11g29870 | WRKY72, expressed | WRKY | transcription | 1.792565625 | 0.004455751 |
| LOC_Os02g08440 | WRKY71, expressed | WRKY | transcription | 1.603427407 | 0.004873931 |
| LOC_Os12g02450 | WRKY64, expressed | WRKY | transcription | 5.146975764 | 0.013568804 |
| LOC_Os05g49620 | WRKY19, expressed | WRKY | transcription | 2.947833584 | 0.030730528 |
| LOC_Os12g40920 | bZIP transcription factor domain containing protein, expressed | zinc fingaer | transcription | 2.146413285 | 4.21891E-14 |
| LOC_Os01g10580 | B-box zinc finger family protein, putative, expressed | zinc fingaer | transcription | 1.783133224 | 1.57284E-09 |
| LOC_Os03g50310 | CCT/B-box zinc finger protein, putative, expressed | zinc fingaer | transcription | 1.663700555 | 1.80291E-07 |
| LOC_Os06g44450 | CCT/B-box zinc finger protein, putative, expressed | zinc fingaer | transcription | 1.520106914 | 0.002600143 |
| LOC_Os05g44400 | GATA zinc finger domain containing protein, expressed | zinc fingaer | transcription | 1.32832076 | 0.005593385 |
| LOC_Os08g38460 | zinc finger, C3HC4 type domain containing protein, expressed | zinc fingaer | transcription | 1.081627606 | 0.006320241 |
| LOC_Os02g52780 | bZIP transcription factor, putative, expressed | zinc fingaer | transcription | 1.070874167 | 0.007886618 |
| LOC_Os09g26200 | ZOS9-11-C2H2 zinc finger protein, expressed | zinc fingaer | transcription | 1.257870833 | 0.014688104 |
| LOC_Os09g26210 | ZOS9-12-C2H2 zinc finger protein, expressed | zinc fingaer | transcription | 1.450112514 | 0.015358041 |
| LOC_Os03g53080 | zinc finger, C3HC4 type domain containing protein, expressed | zinc fingaer | transcription | 1.130985089 | 0.043235539 |
| LOC_Os08g20580 | ZOS8-04-C2H2 zinc finger protein, expressed | zinc fingaer | transcription | 2.478510887 | 0.044419051 |

[Aspect 25]
Non-natural tomato or tobacco of the Solanaceae family with a demethylated promoter region up to 1 kb upstream from the transcription start site of at least one gene selected from the following table:

TABLE 1B

| Tomato homolog | N.benthamiana homolog | Rice locus | Description | Family | Function |
|---|---|---|---|---|---|
| Solyc01g086810 | Niben101Scf05566g02008.1 | LOC_Os03g03700 | MLO domain containing protein, putative, expressed | MLO | disease resistance |
| Solyc11g032130 | Niben101Scf00779g08010.1 | LOC_Os05g34550 | MLO domain containing protein, putative, expressed | MLO | disease resistance |
| Solyc12g049400 | Niben101Scf34602g00003.1 | LOC_Os05g40770 | leucine-rich repeat family protein, putative, expressed | NBS-LRR | disease resistance |
| Solyc06g066370 | Niben101Scf01297g04006.1 | LOC_Os12g17430 | NBS-LRR disease resistance protein, putative, expressed | NBS-LRR | disease resistance |
| Solyc01g108240 | Niben101Scf07172g00019.1 | LOC_Os11g11940 | MLA 10, putative, expressed | NBS-LRR | disease resistance |
| Solyc06g082920 | Niben101Scf05961g02036.1 | LOC_Os11g11920 | resistance protein, putative, expressed | NBS-LRR | disease resistance |
| Solyc08g078340 | Niben101Scf01500g06009.1 | LOC_Os11g45790 | NB-ARC domain containing protein, expressed | NBS-LRR | disease resistance |
| Solyc11g072140 | Niben101Scf03202g03004.1 | LOC_Os11g11810 | NBS-LRR disease resistance protein, putative, expressed | NBS-LRR | disease resistance |
| Solyc04g009040 | Niben101Scf07463g01008.1 | LOC_Os09g34150 | NBS-LRR disease resistance protein, putative, expressed | NBS-LRR | disease resistance |
| Solyc12g010170 | Niben101Scf00073g00013.1 | LOC_Os11g12000 | NBS-LRR disease resistance protein, putative, expressed | NBS-LRR | disease resistance |
| Solyc10g085670 | Niben101Scf05011g01026.1 | LOC_Os01g70080 | NB-ARC domain containing protein, expressed | NBS-LRR | disease resistance |
| Solyc08g007630 | Niben101Scf17398g00012.1 | LOC_Os04g53050 | disease resistance protein RPP13-like protein 1, putative, expressed | NBS-LRR | disease resistance |
| Solyc12g036330 | Niben101Scf06394g08019.1 | LOC_Os07g17220 | disease resistance protein, putative, expressed | NBS-LRR | disease resistance |
| Solyc10g050970 | Niben101Scf05140g01007.1 | LOC_Os11g11960 | disease resistance protein RPM1, putative, expressed | NBS-LRR | disease resistance |
| Solyc03g007380 | Niben101Scf01977g00001.1 | LOC_Os12g39620 | disease resistance protein, putative, expressed | NBS-LRR | disease resistance |
| Solyc09g011330 | Niben101Scf05137g01028.1 | LOC_Os07g17250 | disease resistance protein RPP13-like protein 1, putative, expressed | NBS-LRR | disease resistance |
| Solyc08g066210 | Niben101Scf02217g05010.1 | LOC_Os09g09490 | disease resistance protein RPM1, putative, expressed | NBS-LRR | disease resistance |
| Solyc08g015870 | Niben101Scf01513g00012.1 | LOC_Os01g06790 | disease resistance protein, putative, expressed | NBS-LRR | disease resistance |
| Solyc04g051690 | Niben101Scf01036g00003.1 | LOC_Os12g36730 | stripe rust resistance protein Yr10, putative, expressed | NBS-LRR | disease resistance |
| Solyc07g007870 | Niben101Scf05804g03006.1 | LOC_Os05g335290 | phenylalanine ammonia-lyase, putative, expressed | PAL | disease resistance |
| Solyc04g009260 | Niben101Scf05177g03021.1 | LOC_Os02g41680 | phenylalanine ammonia-lyase, putative, expressed | PAL | disease resistance |
| Solyc02g080040 | Niben101Scf02440g01013.1 | LOC_Os06g11240 | 12-oxophytodienoate reductase, putative, expressed | jasmonate | jasmonate pathway |
| Solyc03g005130 | Niben101Scf01696g06043.1 | LOC_Os08g35740 | 12-oxophytodienoate reductase, putative, expressed | jasmonate | jasmonate pathway |
| Solyc04g009290 | Niben101Scf07728g02001.1 | LOC_Os03g08320 | ZIM domain containing protein, putative, expressed | JAZ | jasmonate pathway |
| Solyc04g009240 | Niben101Scf02248g01001.1 | LOC_Os03g28940 | ZIM domain containing protein, putative, expressed | JAZ | jasmonate pathway |
| Solyc08g075590 | Niben101Scf03374g08019.1 | LOC_Os10g25290 | ZIM domain containing protein, putative, expressed | JAZ | jasmonate pathway |
| Solyc04g009150 | Niben101Scf06382g01004.1 | LOC_Os03g05470 | tyrosine protein kinase domain containing protein, putative, expressed | kinase | kinase |
| Solyc09g014730 | Niben101Scf04445g01002.1 | LOC_Os07g08860 | S-domain receptor-like protein kinase, putative, expressed | kinase | kinase |
| Solyc03g114230 | Niben101Scf05713g03006.1 | LOC_Os11g17380 | protein kinase domain containing protein, expressed | kinase | kinase |
| Solyc07g018010 | Niben101Scf02757g03009.1 | LOC_Os11g35274 | protein kinase domain containing protein, expressed | kinase | kinase |
| Solyc12g009220 | Niben101Scf00299g08001.1 | LOC_Os05g47770 | serine/threonine-protein kinase At1g18390 precursor, putative, expressed | kinase | kinase |
| Solyc01g073985 | Niben101Scf02553g02001.1 | LOC_Os01g48000 | S-locus-like receptor protein kinase, putative, expressed | kinase | kinase |
| Solyc03g123860 | Niben101Scf07741g01003.1 | LOC_Os10g04720 | TKL_IRAK_DUF26-la.5-DUF26 kinases have homology to DUF26 containing loci, expressed | kinase | kinase |
| Solyc07g006770 | Niben101Scf02156g14003.1 | LOC_Os10g33040 | receptor-like protein kinase precursor, putative, expressed | receptor-kinase | receptor |
| Solyc07g007780 | Niben101Scf06678g03002.1 | LOC_Os10g01100 | receptor-like protein kinase, putative, expressed | receptor-kinase | receptor |
| Solyc08g005440 | Niben101Scf05566g02009.1 | LOC_Os01g53920 | receptor-like protein kinase 5 precursor, putative, expressed | receptor-kinase | receptor |
| Solyc12g099040 | Niben101Scf00851g00021.1 | LOC_Os03g62180 | lectin protein kinase family protein, putative, expressed | receptor-kinase | receptor |
| Solyc09g0055090 | Niben101Scf03202g08006.1 | LOC_Os04g52600 | SHR5-receptor-like kinase, putative, expressed | receptor-kinase | receptor |
| Solyc11g013880 | Niben101Scf01735g03002.1 | LOC_Os08g28710 | receptor protein kinase CRINKLY4 precursor, putative, expressed | receptor-kinase | receptor |
| Solyc01g106410 | Niben101Scf04388g02007.1 | LOC_Os04g42480 | receptor-like protein kinase At3g46290 precursor, putative, expressed | receptor-kinase | receptor |
| Solyc10g086180 | Niben101Scf05617g00005.1 | LOC_Os05g34270 | inactive receptor kinase At1g27190 precursor, putative, expressed | receptor-kinase | receptor |
| Solyc06g082920 | Niben101Scf01148g00007.1 | LOC_Os08g24310 | receptor-like protein kinase precursor, putative, expressed | receptor-kinase | receptor |
| Solyc03g019980 | Niben101Scf00887g03011.1 | LOC_Os11g07200 | receptor protein kinase CLAVATA1, precursor, putative, expressed | receptor-kinase | receptor |
| Solyc06g068460 | Niben101Scf04944g05002.1 | LOC_Os11g47240 | leucine-rich repeat receptor protein kinase EXS precursor, putative, expressed | receptor-kinase | receptor |
| Solyc03g116100 | Niben101Scf07231g08006.1 | LOC_Os11g40810 | receptor kinase, putative, expressed | receptor-kinase | receptor |
| Solyc04g079420 | Niben101Scf02422g02015.1 | LOC_Os01g66820 | inactive receptor kinase At1g27190 precursor, putative, expressed | receptor-kinase | receptor |
| Solyc09g008250 | Niben101Scf01927g08005.1 | LOC_Os11g46900 | wall-associated receptor kinase 3 precursor, putative, expressed | receptor-kinase | receptor |
| Solyc06g066370 | Niben101Scf02362g02014.1 | LOC_Os11g47000 | receptor-like protein kinase precursor, putative, expressed | receptor-kinase | receptor |

TABLE 1B-continued

| Tomato homolog | N.benthamiana homolog | Rice locus | Description | Family | Function |
|---|---|---|---|---|---|
| Solyc07g066550 | Niben101Scf08564g00001.1 | LOC_Os08g34640 | receptor-like protein kinase precursor, putative, expressed | receptor-kinase | receptor |
| Solyc09g072810 | Niben101Scf03365g05027.1 | LOC_Os08g36920 | AP2 domain containing protein, expressed | AP2/ERF | transcription |
| Solyc04g015210 | Niben101Scf02553g02001.1 | LOC_Os02g52670 | AP2 domain containing protein, expressed | AP2/ERF | transcription |
| Solyc11g069220 | Niben101Scf03292g03005.1 | LOC_Os01g01870 | helix-loop-helix DNA-binding domain containing protein, expressed | HLH | transcription |
| Solyc04g009690 | Niben101Scf02688g01006.1 | LOC_Os04g23550 | basic helix-loop-helix family protein, putative, expressed | HLH | transcription |
| Solyc03g111540 | Niben101Scf04555g02006.1 | LOC_Os06g09370 | PTF1, putative, expressed | HLH | transcription |
| Solyc10g012170 | Niben101Scf05118g10007.1 | LOC_Os05g48010 | MYB family transcription factor, putative, expressed | MYB | transcription |
| Solyc07g053220 | Niben101Scf04183g00005.1 | LOC_Os07g25150 | myb-related protein 306, putative, expressed | MYB | transcription |
| Solyc03g096190 | Niben101Scf02827g07005.1 | LOC_Os10g41200 | MYB family transcription factor, putative, expressed | MYB | transcription |
| Solyc05g052590 | Niben101Scf00318g03014.1 | LOC_Os09g16510 | WRKY74, expressed | WRKY | transcription |
| Solyc07g042170 | Niben101Scf16657g00010.1 | LOC_Os05g39720 | WRKY70, expressed | WRKY | transcription |
| Solyc01g086810 | Niben101Scf02688g01006.1 | LOC_Os01g51690 | WRKY26, expressed | WRKY | transcription |
| Solyc11g010160 | Niben101Scf05566g02009.1 | LOC_Os02g08440 | WRKY71, expressed | WRKY | transcription |
| Solyc09g007920 | Niben101Scf03712g01008.1 | LOC_Os05g27730 | WRKY53, expressed | WRKY | transcription |

[Aspect 26]
Non-natural tomato or tobacco of the Solanaceae family with a demethylated promoter region up to 1 kb upstream from the transcription start site of at least one gene selected from the following table:

TABLE 2B

| Tomato homolog | N. benthamiana homolog | Rice locus | Description | Family |
|---|---|---|---|---|
| Solyc04g077980 | Niben101Scf06467g01006.1 | LOC_Os10g41330 | AP2 domain containing protein, expressed | AP2/ERF |
| Solyc04g074820 | Niben101Scf14778g00021.1 | LOC_Os09g35020 | AP2 domain containing protein, expressed | AP2/ERF |
| Solyc03g124110 | Niben101Ctg16385g00003.1 | LOC_Os02g54050 | ethylene-responsive transcription factor, putative, expressed | AP2/ERF |
| Solyc09g090130 | Niben101Scf00501g00004.1 | LOC_Os03g09170 | ethylene-responsive transcription factor, putative, expressed | AP2/ERF |
| Solyc08g008280 | Niben101Scf02511g04008.1 | LOC_Os09g35010 | dehydration-responsive element-binding protein, putative, expressed | DREB |
| Solyc08g082110 | Niben101Scf07063g00001.1 | LOC_Os04g43680 | MYB family transcription factor, putative, expressed | MYB |
| Solyc05g052040 | Niben101Scf08546g05002.1 | LOC_Os01g61080 | WRKY24, expressed | WRKY |
| Solyc12g009240 | Niben101Scf00298g00001.1 | LOC_Os01g60640 | WRKY21, expressed | WRKY |
| Solyc04g054910 | Niben101Scf03510g06011.1 | LOC_Os01g60600 | WRKY108, expressed | WRKY |
| Solyc03g026270 | Niben101Scf16007g00011.1 | LOC_Os02g52210 | zinc finger, C3HC4 type domain containing protein, expressed | zinc finger |
| Solyc06g066370 | Niben101Scf01297g04006.1 | LOC_Os03g32230 | ZOS3-12-C2H2 zinc finger protein, expressed | zinc finger |

[Aspect 27]
Non-natural tomato or tobacco of the Solanaceae family with a demethylated promoter region up to 1 kb upstream from the transcription start site of at least one gene selected from the following table:

TABLE 3B

| Tomato homolog | N.benthamiana homolog | Rice locus | Description | Family | Function |
|---|---|---|---|---|---|
| Solyc05g006730 | Niben101Scf06958g02005.1 | LOC_Os03g05290 | aquaporin protein, putative, expressed | aquaporin | channel |
| Solyc06g005170 | Niben101Scf36191g00003.1 | LOC_Os02g41860 | aquaporin protein, putative, expressed | aquaporin | channel |
| Solyc07g047790 | Niben101Scf02824g03017.1 | LOC_Os01g55240 | gibberellin 2-beta-dioxygenase, putative expressed | GA | GA catalysis |
| Solyc09g098110 | Niben101Scf00447g03012.1 | LOC_Os05g43880 | gibberellin 2-beta-dioxygenase, putative, expressed | GA | GA catalysis |
| Solyc03g114230 | Niben101Scf05713g03006.1 | LOC_Os05g48700 | gibberellin 2-beta-dioxygenase, putative, expressed | GA | GA catalysis |
| Solyc11g012980 | Niben101Scf65996g03021.1 | LOC_Os03g63970 | gibberellin 20 oxidase 1, putative, expressed | GA | GA synthesis |
| Solyc01g065980 | Niben101Scf19733g00001.1 | LOC_Os08g34854 | gibberellin 20 oxidase 2, putative, expressed | GA | GA synthesis |
| Solyc01g068620 | Nfcen101Scf03160g01004.1 | LOC_Os08g39140 | heat shock protein, putative, expressed | HSP | HSP |
| Solyc10g017510 | Niben101Scf00072g05003.1 | LOC_Os03g16860 | DnaK family protein, putative, expressed | HSP | HSP |
| Solyc03g124110 | Niben101Ctg16385g00003.1 | LOC_Os05g38530 | DnaK family protein, putative, expressed | HSP | HSP |
| Solyc09g100630 | Niben101Scf21544g01009.1 | LOC_Os02g02410 | DnaK family protein, putative, expressed | HSP | HSP |
| Solyc06g065100 | Niben101Scf04117g07003.1 | LOC_Os06g50300 | heat shock protein, putative, expressed | HSP | HSP |
| Solyc05g015850 | Niben101Ctg14444g00003.1 | LOC_Os09g29840 | heat shock protein, putative, expressed | HSP | HSP |
| Solyc03g116100 | Niben101Scf12143g00001.1 | LOC_Os07g33350 | hsp20/alpha crystallin family protein, putative, expressed | HSP | HSP |
| Solyc07g065840 | Niben101Scf03114g03011.1 | LOC_Os01g62290 | DnaK family protein, putative, expressed | HSP | HSP |
| Solyc05g052040 | Niben101Scf06436g05001.1 | LOC_Os05g09480 | OsIAA16-Auxin-responsive Aux/IAA gene family member, expressed | IAA | IAA |
| Solyc12g096500 | Niben101Scf28688g02003.1 | LOC_Os12g40900 | OsIAA31-Auxin-responsive Aux/IAA gene family member, expressed | IAA | IAA |
| Solyc06g076020 | Niben101Scf04886g05003.1 | LOC_Os02g08420 | cinnamoyl CoA reductase, putative, expressed | CCR | lignin |
| Solyc05g055480 | Niben101Scf19016g00005.1 | LOC_Os08g34280 | cinnamoyl-CoA reductase, putative, expressed | CCR | lignin |
| Solyc04g078420 | Niben101Scf03781g00004.1 | LOC_Os08g17500 | cinnamoyl-CoA reductase, putative, expressed | CCR | lignin |
| Solyc09g014900 | Niben101Scf01813g00013/1 | LOC_Os03g17700 | CGMC_MAPKCGMC_2_ERK.2-CGMC includes CDA, MAPK, GSK3, and CLKC kinases, expressed | MAPK | MAPK |
| Solyc03g122360 | Niben101Scf02749g01008.1 | LOC_Os03g12390 | STE_MEK_ste7_MAP2K.6-STE kinases include homologs to sterile 7, sterile 11 and sterile 20 from yeast, expressed | MAPKK | MAPK |
| Solyc01g108080 | Niben101Scf13926g00004.1 | LOC_Os10g38780 | glutathione S-transferase, putative, expressed | GST | redox |
| Solyc08g082110 | Niben101Scf07063g00001.1 | LOC_Os10g38700 | glutathione S-transferase, putative, expressed | GST | redox |
| Solyc10g009550 | Niben101Scf02511g04008.1 | LOC_Os09g36080 | cytochrome P450, putative, expressed | P450 | redox |
| Solyc03g116910 | Niben101Scf00715g04003.1 | LOC_Os02g17760 | cytochrome P450, putative, expressed | P450 | redox |
| Solyc01g097330 | Niben101Scf16966g06033.1 | LOC_Os12g16720 | cytochrome P450 71A1, putative, expressed | P450 | redox |
| Solyc06g068460 | Niben101Scf04944g05002.1 | LOC_Os09g35020 | cytochrome P450, putative, expressed | P450 | redox |
| Solyc03g026270 | Niben101Ctg15651g00003.1 | LOC_Os02g30080 | cytochrome P450, putative, expressed | P450 | redox |
| Solyc06g068440 | Niben101Scf16007g00011.1 | LOC_Os02g29960 | cytochrome P450 72A1, putative, expressed | P450 | redox |
| Solyc07g061730 | Niben101Scf06091g03006.1 | LOC_Os01g29150 | AP2 domain containing protein, expressed | AP2/ERF | transcription |
| Solyc03g006800 | Niben101Scf02725g06003.1 | LOC_Os09g11480 | AP2 domain containing protein, expressed | AP2/ERF | transcription |
| Solyc03g115010 | Niben101Ctg14882g00002.1 | LOC_Os09g11460 | AP2 domain containing protein, expressed | AP2/ERF | transcription |
| Solyc03g123500 | Niben101Scf01143g10001.1 | LOC_Os05g25260 | AP2 domain containing protein, expressed | AP2/ERF | transcription |
| Solyc05g053330 | Niben101Scf00870g05003.1 | LOC_Os06g10780 | AP2 domain containing protein, expressed | AP2/ERF | transcription |
| Solyc06g068460 | Niben101Scf03049g06001.1 | LOC_Os09g35020 | AP2 domain containing protein, expressed | AP2/ERF | transcription |
| Solyc03g026270 | Niben101Scf04944g05002.1 | LOC_Os04g52090 | AP2 domain containing protein, expressed | AP2/ERF | transcription |
| Solyc12g006860 | Niben101Scf13934g00014.1 | LOC_Os03g08500 | AP2 domain containing protein, expressed | AP2/ERF | transcription |
| Solyc08g078300 | Niben101Scf15009g01020.1 | LOC_Os05g41780 | AP2 domain containing protein, expressed | AP2/ERF | transcription |
| Solyc03g097920 | Niben101Scf01249g04006.1 | LOC_Os02g52670 | AP2 domain containing protein, expressed | AP2/ERF | transcription |
| Solyc12g006230 | Niben101Scf03506g03002.1 | LOC_Os10g41130 | AP2 domain containing protein, expressed | AP2/ERF | transcription |
| Solyc10g055410 | Niben101Scf02025g02002.1 | LOC_Os06g03670 | dehydration-responsive element-binding protein, putative, expressed | DREB | transcription |
| Solyc09g095630 | Niben101Scf10762g02011.1 | LOC_Os09g35010 | dehydration-responsive element-binding protein, putative, expressed | DREB | transcription |
| Solyc09g065990 | Niben101Scf05801g00003.1 | LOC_Os10g41230 | homeobox associated leucine zipper, putative, expressed | HAL | transcription |
| Solyc12g088460 | Niben101Scf07242g07006.1 | LOC_Os03g12860 | homeobox associated leucine zipper, putative, expressed | HAL | transcription |
| Solyc03g006880 | Niben101Scf10027g00002.1 | LOC_Os01g50940 | helix-loop-helix DNA-binding domain containing protein, expressed | HLH | transcription |
| Solyc02g080410 | Niben101Scf07790g03028.1 | LOC_Os01g67480 | helix-loop-helix DNA-binding domain containing protein, expressed | HLH | transcription |
| Solyc11g069430 | Niben101Scf00988g00002.1 | LOC_Os01g01870 | helix-loop-helix DNA-binding domain containing protein, expressed | HLH | transcription |

TABLE 3B-continued

| Tomato homolog | N.benthamiana homolog | Rice locus | Description | Family | Function |
|---|---|---|---|---|---|
| Solyc03g006320 | Niben101Scf09191g00005.1 | LOC_Os03g59670 | basic helix-loop-helix, putative, expressed | HLH | transcription |
| Solyc03g121060 | Niben101Scf10650g02001.1 | LOC_Os02g09480 | myb-like DNA-binding domain containing protein, putative, expressed | MYB | transcription |
| Solyc03g026270 | Niben101Scf03245g04004.1 | LOC_Os05g35500 | MYB family transcription factor, putative, expressed | MYB | transcription |
| Solyc11g066060 | Niben101Scf12868g00008.1 | LOC_Os01g65370 | MYB family transcription factor putative, expressed | MYB | transcription |
| Solyc03g112010 | Niben101Scf28705g00002.1 | LOC_Os03g20090 | MYB family transcription factor, putative, expressed | MYB | transcription |
| Solyc03g095770.3.1 | Niben101Scf06909g04006.1 | LOC_Os10g33810 | myb-related protein Myb4, putative, expressed | MYB | transcription |
| Solyc02g070430 | Niben101Scf04316g03004.1 | LOC_Os01g44390 | MYB family transcription factor, putative, expressed | MYB | transcription |
| Solyc04g081570 | Niben101Scf04331g09018.1 | LOC_Os01g64360 | MYB family transcription factor, putative, expressed | MYB | transcription |
| Solyc02g082040 | Niben101Scf02541g09006.1 | LOC_Os07g43580 | MYB family transcription factor, putative, expressed | MYB | transcription |
| Solyc05g055240 | Niben101Scf01834g04018.1 | LOC_Os07g31470 | MYB family transcription factor, putative, expressed | MYB | transcription |
| Solyc04g080500 | Niben101Scf05082g00002.1 | LOC_Os07g12340 | NAC domain-containing protein 67, putative, expressed | NAC | transcription |
| Solyc04g051840 | Niben101Scf08196g00012.1 | LOC_Os03g60080 | NAC domain-containing protein 67, putative, expressed | NAC | transcription |
| Solyc07g006880 | Niben101Scf39284g00001.1 | LOC_Os12g29330 | no apical meristem protein, putative, expressed | NAM | transcription |
| Solyc04g077980 | Niben101Scf06662g04008.1 | LOC_Os11g05614 | no apical meristem protein, putative, expressed | NAM | transcription |
| Solyc11g072310 | Niben101Scf02083g03005.1 | LOC_Os01g48446 | no apical meristem protein, putative, expressed | NAM | transcription |
| Solyc07g062160 | Niben101Scf01983g09009.1 | LOC_Os11g07460 | TCP family transcription factor, putative, expressed | TCP | transcription |
| Solyc06g065190 | Niben101Scf04117g10020.1 | LOC_Os08g43160 | TCP family transcription factor, putative, expressed | TCP | transcription |
| Solyc02g091930 | Niben101Scf09075g02003.1 | LOC_Os05g43760 | TCP family transcription factor, putative, expressed | TCP | transcription |
| Solyc04g009440 | Niben101Scf19016g00005.1 | LOC_Os08g29660 | WRKY69, expressed | WRKY | transcription |
| Solyc06g074820 | Niben101Scf04436g04003.1 | LOC_Os01g09100 | WRKY10, expressed | WRKY | transcription |
| Solyc12g049560 | Niben101Scf05827g07015.1 | LOC_Os05g27730 | WRKY53, expressed | WRKY | transcription |
| Solyc06g066370 | Niben101Scf01297g04006.1 | LOC_Os09g16510 | WRKY74, expressed | WRKY | transcription |
| Solyc03g082920 | Niben101Scf08590g00005.1 | LOC_Os01g60600 | WRKY108, expressed | WRKY | transcription |
| Solyc08g066510 | Niben101Scf03728g00001.1 | LOC_Os11g29870 | WRKY72, expressed | WRKY | transcription |
| Solyc09g083280 | Niben101Scf08351g06011.1 | LOC_Os02g08440 | WRKY71, expressed | WRKY | transcription |
| Solyc03g117070 | Niben101Scf02413g00007.1 | LOC_Os12g02450 | WRKY 64, expressed | WRKY | transcription |
| Solyc10g078380 | Niben101Scf10031g02004.1 | LOC_Os05g49620 | WRKY19, expressed | WRKY | transcription |
| Solyc05g009310 | Niben101Scf05777g12010.1 | LOC_Os12g40920 | bZIP transcription factor domain containing protein, expressed | zinc fingaer | transcription |
| Solyc07g061720 | Niben101Scf08698g00005.1 | LOC_Os01g10580 | B-box zinc finger family protein, putative, expressed | zinc fingaer | transcription |
| Solyc01g108240 | Niben101Scf07172g00019.1 | LOC_Os03g50310 | CCT/B-box zinc finger protein, putative, expressed | zinc fingaer | transcription |
| Solyc09g090130 | Niben101Scf00501g00004.1 | LOC_Os06g44450 | CCT/B-box zinc finger protein, putative, expressed | zinc fingaer | transcription |
| Solyc06g083980 | Niben101Scf06248g01003.1 | LOC_Os05g44400 | GATA zinc finger domain containing protein, expressed | zinc fingaer | transcription |
| Solyc01g009860 | Niben101Scf02210g01002.1 | LOC_Os08g38460 | zinc finger, C3HC4 type domain containing protein, expressed | zinc fingaer | transcription |
| Solyc05g006740 | Niben101Scf08898g00004.1 | LOC_Os02g52780 | bZIP transcription factor, putative, expressed | zinc fingaer | transcription |
| Solyc03g007380 | Niben101Scf01977g00001.1 | LOC_Os09g26200 | ZOS9-11-C2H2 zinc finger protein, expressed | zinc fingaer | transcription |
| Solyc04g051690 | Niben101Scf12084g00003.1 | LOC_Os09g26210 | ZOS9-12-G2H2 zinc finger protein, expressed | zinc fingaer | transcription |
| Solyc10g009110 | Niben101Scf01426g00001.1 | LOC_Os03g53080 | zinc finger, C3HC4 type domain containing protein, expressed | zinc fingaer | transcription |
| Solyc05g007770 | Niben101Scf11208g00002.1 | LOC_Os08g20580 | ZOS8-04-C2H2 zinc finger protein, expressed | zinc fingaer | transcription |

[Aspect 28]
The non-natural rice (*Oryza sativa*) of the Poaceae family according to aspect 22 or the non-natural tomato or tobacco of the Solanaceae family according to aspect 25 having resistance to a pathogen.
[Aspect 29]
The non-natural rice (*Oryza sativa*) of the Poaceae family according to aspect 23 or the non-natural tomato or tobacco of the Solanaceae family according to aspect 26 having low temperature resistance.
[Aspect 30]
The non-natural rice (*Oryza sativa*) of the Poaceae family according to aspect 24 or the non-natural tomato or tobacco of the Solanaceae family according to aspect 27 having salt resistance.
[Aspect 31]
The non-natural rice (*Oryza sativa*) of the Poaceae family or the non-natural tomato or tobacco of the Solanaceae family according to any one of aspects 22 to 30, wherein the expression of the at least one gene is induced.

BRIEF DESCRIPTION OF DRAWINGS

FIG. 3 is a diagram showing results of multiple alignment of genomic sequences of about 1 kb promoter regions of LOC_Os05g47770 related to disease resistance, LOC_Os02g52210 related to low temperature resistance, and LOC_Os05g38530 related to salt resistance, for Nipponbare (NB), Koshihikari (Koshi), RP Bio-226, and Shuhui 498.

FIG. 4 is a diagram showing that regenerated line plants obtained by probenazole-treatment of rice calluses in the process of dedifferentiation or redifferentiation exhibit resistance to blast. A: As compared to Nipponbare (NB) and individuals regenerated without a resistance inducer treatment (0-X), R-DR individuals regenerated with the resistance inducer treatment (R-DR-X) inhibited the hyphal elongation of Rice blast fungus in the leaf sheath and exhibited a significant blast resistance as compared to Nipponbare (P<0.05). The last number indicative of the lineage denotes the number of independently regenerated individuals. R-DR individuals regenerated with the resistance inducer treatment (R-DR-X) inhibited the hyphal elongation of rice blast fungus in the leaf sheath and exhibited a significant blast resistance as compared to Nipponbare (P<0.05). The last number indicative of the lineage denotes the number of independently regenerated individuals. B: Hyphal elongation of GFP-expressing rice blast fungus in the rice leaf sheath. The R-DR line inhibited hyphal elongation of blast fungus as compared to Nipponbare (NB) and 0-X and exhibited resistance to blast.

FIG. 8 is a diagram shoring that regenerated line plants of *Nicotiana benthamiana* callus treated with probenazole in the process of dedifferentiation or redifferentiation exhibit resistance to *Botrytis cinerea* and *Pseudomonas syringae* pv. *tabaci*. A: As compared to wild-type *Nicotiana benthamiana* (WT) and a current generation (R0) of a line regenerated without a resistance inducer treatment (0d), R0 of a line regenerated with a resistance inducer treatment (7d) inhibited lesion expansion of gray mold and exhibited significant resistance as compared to WT (*: P<0.05, **: P<0.01). B: as compared to wild-type *Nicotiana benthamiana* (WT), R1 of lines (7d and 14d) regenerated with resistance inducer treatment inhibited lesion expansion of gray mold and exhibited significant resistance as compared to WT (P<0.05), and the acquired resistance was maintained until the next generation. C: As compared to wild-type *Nicotiana benthamiana* (WT), R0 of lines (7d, 14d, and 21d) regenerated with resistance inducer treatment inhibited the growth of *Pseudomonas syringae* pv. *tabaci* and exhibited significant resistance as compared to WT (P<0.05). It was suggested that the disease resistance imparted by orientation of epigenetic mutations exhibits resistance to a wide range of pathogens.

FIG. 9 is a diagram showing that regenerated line plants obtained by low-temperature treatment of rice callus in the process of dedifferentiation process exhibit low-temperature resistance. A: As compared to Nipponbare (NB) and a second generation (R1) of the line (7d-28) regenerated under normal temperature treatment, the R1 of the line (7d-4) regenerated under low-temperature treatment suppressed whitening of leaf blades observed after lower temperature treatment, and many upright leaf blades were observed. B: SES after low-temperature treatment of Nipponbare (NB), the second generation (R1) of the line regenerated under normal temperature treatment (7d-28-X), and R1 of the line regenerated under low-temperature treatment (7d-4-X). In 7d-4-3 and 7d-4-5, an increase in SES was significantly suppressed as compared to NB (P<0.05), indicating low temperature resistance. The last number indicative of the lineage denotes the number of independently regenerated individuals. C: Survival rates after low-temperature treatment of Nipponbare (NB), the second generation (R1) of the line regenerated under normal temperature treatment (7d-28-X), and R1 of the line regenerated under low-temperature treatment (7d-4-X). In 7d-4-3 and 7d-4-5, the survival rate was significantly higher than NB (P<0.05), indicating low temperature resistance. The last number indicative of the lineage denotes the number of independently regenerated individuals.

FIG. 10 is a diagram showing results of measurement of root elongation amounts after seeds of Nipponbare (NB), line regenerated without treatment (Na-0), and a second generation (R1) of a line regenerated under 100 mM NaCl treatment (Na-100) were cultured for 7 days on 0.7% agar to which NaCl was added (n=5).

FIG. 12 is a diagram showing that a regenerated tomato line (PBZ_2W) treated with probenazole in the process of dedifferentiation/redifferentiation acquires *Botrytis cinerea* resistance. A, B, C: Inhibition of lesion expansion of *Botrytis cinerea* (broken line) in tomato leaves. A probenazole-treated line (PBZ_2W-2) inhibited the lesion expansion as compared to a parent line (WT) and a control line (C_2W-2) and exhibited resistance. D: As compared to a tomato parent line (WT) and control lines regenerated without resistance inducer treatment (C_2W-2 and C_2W-3), lines regenerated with resistance inducer treatment (PBZ_2W-3 and PBZ_2W-13) inhibited the lesion expansion of *Botrytis cinerea* and exhibited significant *Botrytis cinerea* resistance as compared to WT (*; P<0.05). The last number indicative of the lineage denotes the number of independently regenerated individuals.

DESCRIPTION OF EMBODIMENTS

[Definition]

Figure 1:
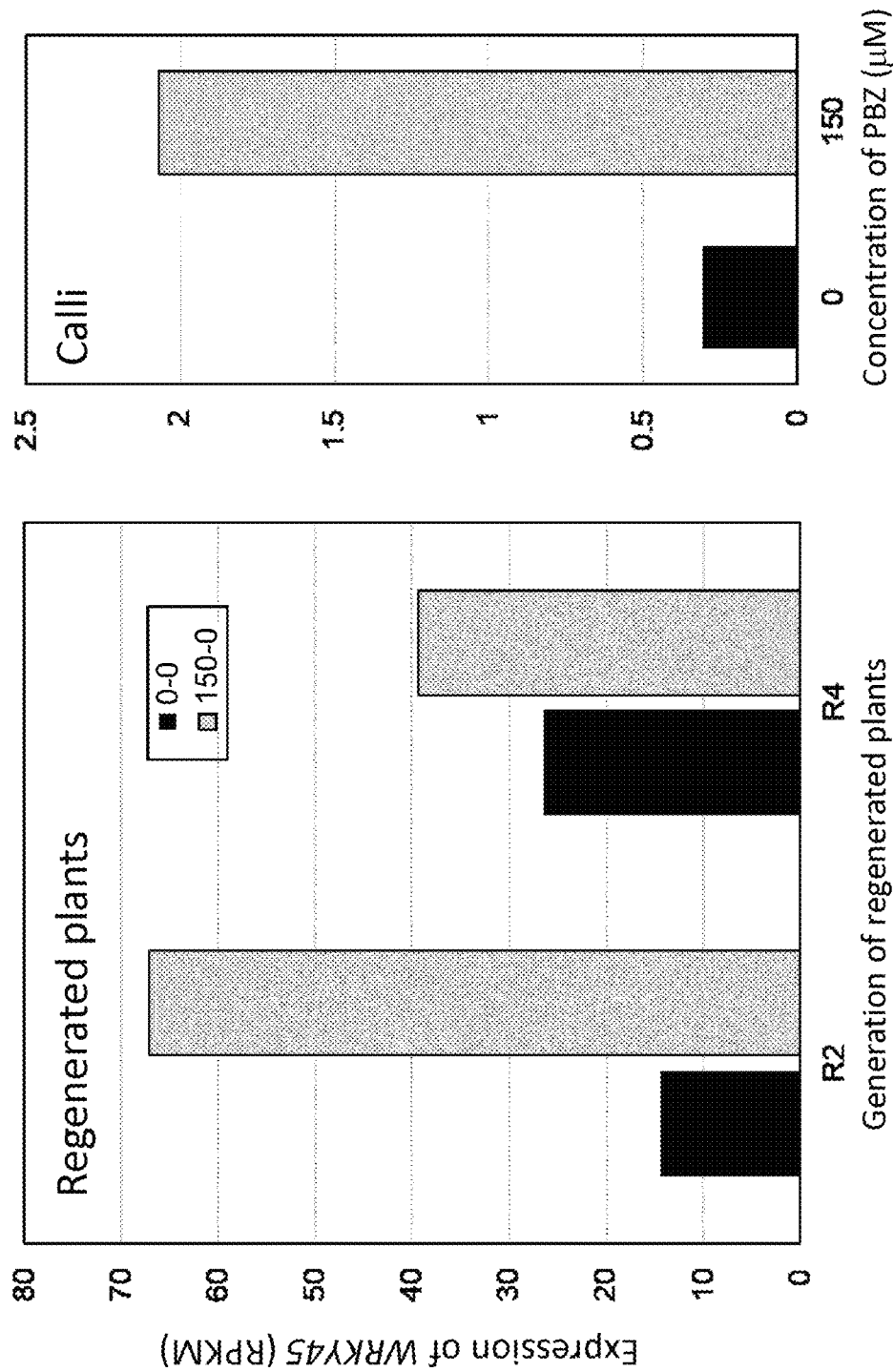
FIG. 1 is a diagram showing that expression of the WRKY45 gene is induced in probenazole (PBZ) treated calli and regenerated plants. Callus data show expression on callus-inducing medium on the 7th day after treatment.

Plant: As used herein, the term "plant" or "plant of interest" means a plant capable of deriving a dedifferentiated callus from a portion of a plant body, and particularly includes rice (*Oryza sativa*) of the family Poaceae and tobacco and tomato of the family Solanaceae. In an aspect of the present invention, the plant is a monocotyledon or a dicotyledon. In an aspect of the present invention, monocotyledon is Poales. In an aspect of the present invention, Poales is the Poaceae family. In an aspect of the present invention, the dicotyledon is Solanales. In an aspect of the present invention, Solanales is the Solanales family. In an aspect of the present invention, the Solanaceae is the genus *Solanaceae* or the genus *Nicotiana*. In an aspect of the present invention, the dicotyledon is Brassicaceae. In an aspect of the present invention, the Brassicaceae is the Brassicaceae family. As used herein, the term "portion" of a "plant" or "plant of interest" means at least one of roots, stems, leaves, flowers, fruits, hypocotyls, and shoots of a plant body. In an aspect of the present invention, the "portion" of a "plant" or "plant of interest" does not include seeds.

Vegetative propagation: As used herein, the term "vegetative propagation" refers to vegetative propagation that is reproduction by organs other than seeds. The vegetative propagation includes propagation through a propagating body such as tuberous roots, tubers, corms, and bulbs, and artificial propagation such as cutting, grafting, root cutting, and leaf cutting, and tissue culture (see Tsuyoshi Nishio et al., Plant Breeding, 4th Edition, 2013, Buneido Shuppan). Examples of combinations of vegetative propagation methods and plants are as follows: Tuberous root: sweet potato, dahlia. Tubers: potato, Jerusalem artichoke. Corms: taro, konjac. Bulbs: onion, tulip. Cutting: In addition to using branches, roots and leaves may be used. Stem cutting: figs, blueberries. Root cutting: mulberry tree, sansevieria. Leaf cutting: succulent plants such as aloe. Grafting: fruit trees such as tomatoes, watermelons, and apples.

Gene: As used herein, the term "gene" or "gene of interest" preferably refers to a gene capable of enhancing a specific trait of a plant when expression is induced, and particularly, a gene other than a constitutive expression gene. Examples of these genes are the WRKY45 gene, which has been reported to confer disease resistance to rice and tobacco, and the LOC_Os09g28440, LOC_Os09g35020, LOC_Os10g41330, LOC_Os02g54050, LOC_Os01g61080, LOC_Os03g53020, LOC_Os04g43680, and LOC_Os06g51260, which have been reported to confer low temperature resistance to rice, LOC_Os05g48700, LOC_Os05g38530, LOC_Os01g64360, LOC_Os02g52670, and LOC_Os02g52670, and LOC_Os08g29660, which have been reported to confer salt resistance to rice, and homologues in rice and tobacco corresponding thereto.

Other examples of the gene imparting disease resistance include genes listed in Table 1A having a significant expression increase actually confirmed (False Discovery Rate (FDR)>0.05) in the disease-resistant rice in Examples of this application, and homologues in tomato and tobacco corresponding thereto listed in Table 1B.

Other examples of the gene imparting low temperature resistance include genes listed in Table 2A having a significant expression increase actually confirmed (False Discovery Rate (FDR)>0.05) in the low temperature resistant rice in Examples of this application, and homologues in tomato and tobacco corresponding thereto listed in Table 2B.

Examples of genes imparting salt resistance include genes listed in Table 3A having a significant expression increase actually confirmed (False Discovery Rate (FDR)>0.05) in the salt-resistant rice in Examples of this application, and homologues in tomato and tobacco corresponding thereto listed in Table 3B.

Dedifferentiation-inducing conditions: As used herein, the phrase "culturing under dedifferentiation-inducing conditions" means culturing in the presence of a dedifferentiation inducer such as 2,4-Dichlorophenoxyacetic acid (2,4-D), indole-3-acetic acid (IAA), 6-benzylaminopurine (6-BA), and trans-zeatin (t-zeatin), and more specifically means culturing on or in a medium containing 2,4-D, IAA, 6-BA, trans-zeatin, etc. The concentration of the dedifferentiation inducer to be used can appropriately be determined by those skilled in the art, and typically, the final concentration is 0.01 mg/L to 2 mg/L, for example, 0.00125 to 10.24 mg/L, 0.0025 to 5.12 mg/L, 0.005 to 2.56 mg/L, 0.01 to 1.28 mg/L, 0.02 to 0.64 mg/L, 0.04 to 0.32 mg/L, or 0.08 to 0.16 mg/L. In an embodiment of the present invention, a period of "culturing under dedifferentiation-inducing conditions" is 1 to 60 days, 2 to 59 days, 3 to 58 days, 4 to 57 days, 5 to 56 days, 6 to 55 days, 7 to 54 days, 8 to 53 days, 9 to 52 days, 10 to 51 days, 11 to 50 days, 12 to 49 days, 13 to 48 days, 14 to 47 days, 15 to 46 days, 16 to 45 days, 17 to 44 days, 18 to 43 days, 19 to 42 days, 20 to 41 days, 21 to 40 days, 22 to 39 days, 23 to 38 days, 24 to 37 days, 25 to 36 days, 26 to 35 days, 27 to 34 days, 28 to 33 days, 29 to 32 days, 30 to 31 days, or 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Redifferentiation-inducing conditions: As used herein, the phrase "culturing under redifferentiation-inducing conditions" means culturing in the presence of a redifferentiation inducer such as kinetin, IAA, 6-BA, t-zeatin, and 1-Naphthalene acetic acid (NAA), and more specifically means culturing on or in a medium containing kinetin etc. The concentration of the redifferentiation inducer to be used can appropriately be determined by those skilled in the art, and typically, the final concentration is 0.01 mg/L to 2 mg/L, for example, 0.00125 to 10.24 mg/L, 0.0025 to 5.12 mg/L, 0.005 to 2.56 mg/L, 0.01 to 1.28 mg/L, 0.02 to 0.64 mg/L, 0.04 to 0.32 mg/L, or 0.08 to 0.16 mg/L. In an embodiment of the present invention, the period of "culturing under redifferentiation-inducing conditions" is 1 to 60 days, 2 to 59 days, 3 to 58 days, 4 to 57 days, 5 to 56 days, 6 to 55 days, 7 to 54 days, 8 to 53 days, 9 to 52 days, 10 to 51 days, 11 to 50 days, 12 to 49 days, 13 to 48 days, 14 to 47 days, 15 to 46 days, 16 to 45 days, 17 to 44 days, 18 to 43 days, 19 to 42 days, 20 to 41 days, 21 to 40 days, 22 to 39 days, 23 to 38 days, 24 to 37 days, 25 to 36 days, 26 to 35 days, 27 to 34 days, 28 to 33 days, 29 to 32 days, 30 to 31 days, or 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

Callus: As used herein, the term "callus" typically means a mass of undifferentiated plant cells cultured on a solid medium etc. Those skilled in the art will appreciate that as long as the callus is in a dedifferentiated state, the callus can be present not only on a dedifferentiation-inducing medium (callus-inducing medium) as well as on a redifferentiation medium (e.g., immediately after being placed on a redifferentiation medium).

Stimulation: The term "stimulation" as used herein refers to a physical stimulus such as low-temperature treatment and chemical stimulus such as treatment with a resistance inducer such as probenazole, acibenzolar S-methyl, tiadinil, isotianil, salicylic acid (as used herein, the term "resistance inducer (inducer of resistance)" is synonymously used with the term "plant immunity inducer"). However, those skilled in the art will appreciate that the distinction between physical and chemical stimuli is not strict and is not essential in the present invention. As long as expression of a gene of interest is induced, one physical or chemical stimulus is equivalent to another physical or chemical stimulus. In an aspect of the present invention, the final concentration of probenazole is 10 to 1000 µM, 10 to 500 µM, 20 to 400 µM, 20 to 300 µM, 30 to 100 µM, or 30 to 70 µM. In an embodiment of the present invention, the low-temperature treatment is performed at a temperature at least 5° C., at least 6° C., at least 7° C., at least 8° C., at least 9° C., at least 10° C., at least 11° C., at least 12° C., at least 13° C., at least 14° C., at least 15° C., at least 16° C., at least 17° C., at least 18° C., at least 19° C., or at least 20° C. higher than the lower limit of the growth limit temperature of the callus. In an aspect of the present invention, the salt is 10 to 1000 mM, 20 to 800 mM, 50 to 400 mM, or 100 to 200 mM sodium chloride.

Selection: As used herein, the term "selection" of callus means, for example, selecting low-temperature resistant callus by low-temperature treatment of callus, or selecting callus growing at room temperature after low-temperature treatment of callus for a certain period of time, culturing callus in a selection medium containing a drug to select callus exhibiting resistance to the drug.

Trait: As used herein, the term "enhancing the trait of interest" includes enhancement of resistance to a pathogen, enhancement of low temperature resistance, and enhancement of salt resistance. Examples of the pathogen include rice blast fungus, *Xanthomonas oryzae*, *Botrytis cinerea*, and *Pseudomonas syringae* pv. *tabaci*.

Demethylation: In an aspect of the present invention, when the promoter region of a gene of a non-natural plant is "demethylated", this means that when the region of the non-natural plant is compared with the region of a natural plant having the same genetical background, at least 70%, at least 80%, at least 90%, or at least 95% of the cytosine residues methylated in the natural plant is demethylated in the corresponding cytosine residues of the non-natural plant. In another aspect of the present invention, when the promoter region of 1 kb upstream from the transcription start site of a non-natural plant gene is "demethylated", this means that 30% or less, 20% or less, 10% or less, or 5% or less of the cytosine residues are methylated in the region. In an aspect of the present invention, the "promoter region" of a gene of a non-natural plant means a region 300 base upstream from the transcription start site of the gene, a region 500 base upstream from the transcription start site of the gene, a region of 1 kb upstream from the transcription start site, a region of 2 kb upstream from the transcription start site, a region of 3 kb upstream from the transcription start site, a region of 4 kb upstream from the transcription start site, a region of 5 kb upstream from the transcription start site, preferably a region of 1 kb upstream from the transcription start site.

At least one gene: In this description, "at least one gene" includes the meaning of at least 1, at least 2, at least 3, at least 4, at least 5, at least 6, at least 7, at least 8, at least 9, at least 10, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, At least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, or at least 100 genes. In this description, "at least one gene" includes the meaning of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 genes.

EXAMPLES

Example 1

Production of Disease-Resistant Rice Line (R-DR Line) by Probenazole Treatment of Rice Callus and Genetic Stability of Disease-Resistant Phenotype
Materials and Methods
Plant Rice (*Oryza sativa* cv. *Nipponbare*; Rice variety: Nipponbare) was used as the plant.

Rice seeds were sterilized, and the seeds were evenly spread on a glass petri dish (60 mm diameter) covered with filter paper (55 mm diameter) moistened with distilled water and were cultured in a 24-hour light-period artificial weather apparatus for 3 days to perform sprouting treatment. Culture soil vermiculite was placed in a cell tray, and the seeds subjected to the sprouting treatment were each seeded in a cell. The cell tray was placed on a water receiver and cultivated a a room temperature of 28° C., or in an artificial weather chamber at 28° C. with a 16-hour dark period and an 8-hour light period under a state of being constantly filled with ion-exchanged water.
Fungus Fungus to be inoculated into rice was rice blast fungus (*Magnaporthe grisea* strain K-06) transformed by using a plasmid acquired by inserting Yeast TEF promoter (Non-Patent Document 6) and green fluorescent protein (GFP) into the EcoRI and ClaI sites of the pBIG2RHPH2 plasmid (see Non-Patent Document 5) to quantify resistance.

The fungus was cultured by the following method. Blast fungus stored in a barley grain medium (about 4 ml of barley seeds and about 1.5 ml of 0.5% sucrose solution are placed in a 20 ml test tube, swollen overnight, and then sterilized by autoclave at 121° C. for 20 minutes. see Non-Patent Document 7) was inoculated into a PDA slope medium (Potato Dextrose Broth (Difco, USA) 2.4 g, Agar 1.5 g, distilled water 100 ml) on a slant and cultured at 25° C. for 7 days. Fungus bodies were cut out from the hyphae extending on the surface of the medium, inoculated into a PDA flat medium (composition is the same as the slope medium), and cultured at 25° C. for 7 days. The fungus bodies were cut out from the hyphae extending on the surface of the medium together with the PDA medium, inoculated on an oatmeal flat medium for sporulation (see Non-Patent Document 8), and cultured at 25° C. for 7 days. After pouring 10 ml of sterile water on the surface of the medium and scraping the aerial hyphae with a sterilized brush, a hyphal suspension was removed, and spores are formed by culturing at 25° C. for 7 days.

The spore suspension used for inoculation of rice blast fungus was prepared by the following method. Blast fungus stored in the barley grain medium was inoculated into the PDA slope medium and cultured at 25° C. for 7 days. Fungus bodies were cut out from the hyphae extending on the surface of the medium, inoculated into the PDA flat medium, and cultured at 25° C. for 7 days. The fungus bodies were cut out from the hyphae extending on the surface of the medium together with the PDA medium, inoculated on the oatmeal flat medium for sporulation, and cultured at 25° C. for 7 days. After pouring 10 ml of sterile water on the surface of the oatmeal medium and scraping the aerial hyphae, a hyphal suspension was removed. After covering with Saran Wrap® with vent holes, spores are formed by culturing at 25° C. for 7 days. After 5 ml of sterile water was poured onto the surface of the oatmeal medium on which the spores were formed, the spores were scraped off, and the suspension was transferred to a 15 ml conical tube. Sterilized water was added until 10 ml, and after centrifugation at 2000×g at room temperature for 2 minutes, an operation of removing a supernatant was repeated 5 times to remove contaminants. By adding 0.1% agar water after sterilization to achieve the spore concentration of $5.0 \times 10^5$ conidia/ml, a spore suspension for inoculation was prepared.

*Xanthomonas oryzae* pv. *oryzae* was used for a bacterial leaf blight inoculation experiment. A freeze stock of each bacterium was streaked on a PS medium [1% (v/v) peptone, 0.5% (v/v) sucrose, 1% (v/v) monosodium glutamate, 1.5% (v/v) agar]and cultured at 28° C. for 5 days.
Media, etc.

The composition of the rice dedifferentiation-inducing medium is as follows.

TABLE 4

| Rice Dedifferentiation-Inducing Medium | |
|---|---|
| Sucrose | 30 g/L |
| N6 Basal Salt Mixture | 3.98 g/L |
| Casamino acids | 300 mg/L |
| L Proline | 2878 mg/L |
| N6 Vitamine | 5 ml/L |
| 1 mg/ml 2,4-D | 2 ml/L |
| Gelrite | 4 g/L |

(Adjusted to pH 5.8) Autoclave: 121° C., 20 minutes

The composition of the rice redifferentiation-inducing medium is as follows.

TABLE 5

| Rice Redifferentiation-Inducing Medium | |
|---|---|
| Sucrose | 30 g/L |
| MS Basal MD | 4302.09 mg/L |
| Casamino acids | 2 g/L |
| Sorbitol | 30 g/L |

TABLE 5-continued

| Rice Redifferentiation-Inducing Medium | |
|---|---|
| NAA (1 mg/ml of Ethanol) | 0.2 ml/L |
| Kinetin (0.1 mg/ml) | 20 ml |
| Gelrite | 3.0 g/L |

(Adjusted to pH 5.8) Autoclave: 121° C., 20 minutes

The composition of the rice rooting medium is as follows.

TABLE 6-1

| Rice Rooting Medium | |
|---|---|
| Sucrose | 30 g/L |
| MS Basal MD | 4302.09 mg/L |
| Gelrite | 3.0 g/L |

Autoclave: 121° C., 20 minutes

Induction of Expression of Defense-Related Gene WRKY45 in Rice Callus

Rice (*Oryza sativa* cv. *Nipponbare*; Rice variety: Nipponbare) was used as a plant material to be evaluated. The seeds of Nipponbare with the husk removed were sterilized with 70% ethanol, and 25 seeds were inserted into the rice dedifferentiation-inducing medium with the embryos exposed from the medium surface and were cultured in a growth chamber until callus was formed (see Non-Patent Document 9).

The formed callus was transplanted to a new rice dedifferentiation-inducing medium or a rice dedifferentiation-inducing medium to which Oryzemate granules (containing 24% probenazole as an active ingredient; Meiji Seika Pharma Co., Ltd.; the Ministry of Agriculture, Forestry and Fisheries registration No. 19541) were added so that the final concentration of probenazole known to induce expression of the defense-related gene WRKY45 (Non-Patent Document 10) was 50, 100, or 150 μM, and was cultured in a growth chamber under the same conditions for 7 days. It is known that probenazole induces the expression of defense-related genes such as WRKY45 through activation of a salicylic acid pathway in rice and imparts resistance to blast fungus etc. to rice (Non-Patent Document 10). Comprehensive gene expression analysis using RNA-seq was performed on the callus on the 7th day after probenazole treatment on the rice dedifferentiation-inducing medium (callus-inducing medium) to confirm that the expression of the WRKY45 gene was actually induced. See FIG. 1.

To regenerate callus into a rice plant body, the callus grown on the medium was transplanted to the rice redifferentiation-inducing medium or the rice redifferentiation-inducing medium to which Oryzemate granules were added so that the final concentration of probenazole was 50, 100, or 150 μM, and was cultured in a growth chamber under the same conditions until shoots were formed.

The redifferentiated shoots were transferred to the rice rooting medium in a plant box and cultured in a growth chamber under the same conditions until rooted plants were formed. The regenerated rice plants were transplanted into cultivation soil and acclimated to the outside air in a plastic cup (diameter: 8 cm, depth: 12 cm). After the acclimatization treatment, the plants were transplanted to a cell tray, kept in a state of being constantly filled with ion-exchanged water on a water receiver, and grown at a room temperature of 28° C. Seeds obtained by self-propagation of the obtained regenerated rice individuals (R0) of the current generation were referred to as R1 seeds. The same passage or subculture was repeated to obtain seeds of R2, R3, and R4. A rice line obtained by treating rice callus with 50 to 150 μM probenazole in the dedifferentiated state and/or the regeneration process as described above for regeneration into a plant is referred to as an R-DR line. Regenerated individuals obtained from the callus treated with 50, 100, and 150 μM probenazole on the rice dedifferentiation-inducing medium are referred to as a 50-0 line, a 100-0 line, and a 150-0 line, respectively, and regenerated individuals obtained from the callus treated with 50, 100, and 150 μM probenazole on the rice redifferentiation-inducing medium are referred to as a 0-50 line, a 0-100 line and a 0-150 line, respectively. Regenerated individuals obtained from the callus untreated with probenazole are referred to as a 0-0 line.

Comprehensive Analysis of Rice Gene Expression

The rice gene expression was comprehensively analyzed by the RNA-seq method. Total RNA was extracted from untreated rice plants grown in an artificial weather chamber at 3 weeks of age in accordance with the following method. RNA Suisui P (product number RS-0002N, Reso, Tsukuba City) was used as an extraction buffer. Samples are each added to a sample tube containing 500 μL RNA Suisui P and 20 μL mercaptoethanol and thoroughly ground with Fast-Prep (FP120; Thermo Scientific Savant, US), and total RNA was extracted according to the protocol accompanying to the kit. The 2100 Bio-analyzer electrophoresis system (Agilent, US) was used to confirm the quality of the extracted total RNA. The Ribo-Zero rRNA Removal Kit (Plant leaf) (product number RZPL11016, illumina, US) was used to remove cytoplasmic, mitochondrial, and chloroplast ribosomal RNA from 2-3 mg of total RNA according to the kit's manual. A cDNA library was prepared from purified RNA by using the AB Library Builder™ System (Thermo Fisher Scientific, US) and the Ion RNA-Seq for AB Library Builder™ System (Product No. 4463794, Thermo Fisher Scientific, US) according to the kit's manual (hereinafter, all kits and devices used for next-generation sequencer analysis are manufactured by Thermo Fisher Scientific). The Ion Chef™ Instrument (Product No. 4484177) and the Ion PI™ Hi-Q™ Chef Kit (Product No. A27198) were used according to the manual to clone cDNA into microbeads by emulsion PCR. Furthermore, the microbeads prepared by using the Ion Chef™ Instrument were filled in the Ion PI™ Chip, and a DNA sequence was analyzed by using the next-generation sequencer Ion Proton™.

The obtained data was converted to the fastq file format by using dedicated software (Torrent Suite 5.4.0, Thermo Fisher Scientific, US) and aligned to the rice reference sequence (Os-Nipponbare-Reference-IRGSP-1.0 <https://rapdb.dna.affrc.go.jp/download/irgsp1.html>) by using RNA-Seq Analysis of the next-generation sequencer data analysis software CLC Genomics Workbench Ver10.1.1 (QIAGEN bioinformatics, US). Additionally, RNA-Seq Analysis and the gene definition information (MSU Rice Genome Annotation Project Release 7 <http://rice.plantbiology.msu.edu/>) were used to count reads mapped to each gene and perform normalization and statistical analysis of the data. The Reads Per Kilobase of gene per Million mapped sequence reads (RPKM) value (see Non-Patent Document 11) was obtained as the expression value of each gene, and a false discovery rate (FDR) was obtained for multiple comparison of gene expression between samples. When the FDR was 0.05 or less, a difference was regarded as being significant, and a group of genes having significant expression variation (Differentially Expressed Genes; DEG) between the samples was extracted. Gene Ontology Enrichment Analysis was performed by using AgriGO v2 (<http:// systemsbiology.cau.edu.cn/agriGOv2/index.php>) to clarify functional characteristics of DEG.

Whole Genome DNA Methylation Analysis of Rice

The next-generation sequencer (Ion Proton™ System, Thermo Fisher Scientific, US) was used for whole genome methylation analysis. NucleoSpin® Plant II (Product No. 740770, MACHEREY-NAGEL GmbH & Co. KG, Germany) was used to extract genomic DNA from rice plant bodies. To convert unmethylated cytosine of the extracted genomic DNA to uracil, a bisulfite reaction was performed for 16 hours by using the EZ DNA methylation Kit (product number D5001, ZYMO RESEARCH, US). Lambda DNA was used as a control for monitoring the efficiency of bisulfite conversion. To create a library, single-stranded DNA randomly cleaved by bisulfite treatment using the EpiNext Post-Bisulfite DNA Library Preparation Kit (product number P-1055-12, Epigentek US) is returned to double-stranded DNA. By using the AB Library Builder™ and the Ion Plus Fragment Library Kit for AB Library Builder™ System (Product No. 4477597, Thermo Fisher Scientific, US), a genomic library was prepared from the extracted DNA according to the kit's manual. The Ion Chef™ system and the Ion PI™ Hi-Q™ Chef Kit were used according to the manual to clone DNA fragments into microbeads by emulsion PCR. Furthermore, the prepared microbeads were filled in the Ion PI Chip by using the Ion Chef system, and the DNA sequence was analyzed by using the next-generation sequencer Ion Proton.

The obtained base sequence data was aligned to the rice reference sequence (Os-Nipponbare-Reference-IRGSP-1.0) by using the whole-genome bisulfite sequence analysis software Bismark 0.15.0 (Non-Patent Document 12) to create a file in the bam format. A methylation rate of each base was calculated for each CG, CHG, and CHH motif by using bismark_methylation_extractor (<https://www.bioinformatics.babraham.ac.uk/projects/bismark/>) from the read information aligned to the reference sequence and is converted to a bedgraph file by using bismark2bedGraph. Each bedgraph file was visualized on the Integrative Genomics Viewer (IGV; Non-Patent Document 13), and the methylation state of the promoter region of the gene was analyzed.

Evaluation of Disease Resistance of Rice

Inoculation of blast fungus and evaluation of resistance were performed as follows. An upper portion of the second leaf sheath was cut to a length of 5 cm from a 3-week-old young rice seedling, and a blast fungus spore suspension was injected into the lumen of the leaf sheath. A filter paper (55 mm diameter) was spread on a glass petri dish (60 mm diameter), 4 ml of sterilized water was added, and the inoculated leaf sheath was placed and cultured at 22° C. for 48 hours. After removing 1 cm from both ends of the leaf sheath, the leaf sheath was divided into two in the vertical direction, and the lumen of the leaf sheath was observed with a fluorescence microscope (Axioskop 2 Plus; Zeiss, Germany). Three locations were randomly selected for each leaf sheath, photographs were taken with a digital camera (AxioCam HRc, Zeiss, Germany), and an elongation amount of infection hypha was measured by using image analysis software ImageJ on a computer screen. Each experiment was performed 3 times or more, and 5 or more individuals were used for each variety/line in one experiment, and the average value for each experiment was obtained.

Inoculation of *Xanthomonas oryzae* pv. *oryzae* and evaluation of resistance were performed as follows. *Xanthomonas oryzae* pv. *oryzae* grown on the PS medium were scraped from the surface of the medium and suspended in sterile water for adjustment to $OD_{600}=0.3$. Boil-sterilized scissors were dipped in a suspension of the bacteria, and the fourth leaf of rice was cut off at a site 2 cm from the tip. After culturing at 22° C. in a bright place for 2 weeks, a length of a bleached lesion showing a disease symptom was measured.

Results and Discussion

In the R-DR rice line, the expression of the defense-related gene WRKY45 is induced in the absence of probenazole.

Comparing the phenotypes between the R-DR line and Nipponbare, no difference was recognized in the visible phenotype or the yield in a field. No difference in callus survival rate was recognized between probenazole-treated callus and control callus (100% survival in both cases).

To confirm whether the expression of the WRKY45 induced in rice callus was maintained in the R-DR line, the gene expression was comprehensively examined by RNA-seq analysis, and transcriptome was compared between the 150-0 line and the 0-0 line.

As a result, in the 150-0 line, the expression of the 304 genes including the WRKY45 gene was significantly increased even without probenazole treatment. Gene ontology analysis of these gene sets revealed that the genes involved in biological or abiotic stress responses were significantly enriched. See Table 6-2.

TABLE 6-2

Gene Ontology Analysis of Gene Sets Having Expression Increased in the R-DR Line as Compared to the 0 Line

| GO_acc | term_type | Term query item | FDR |
|---|---|---|---|
| GO:0006950 | P | response to stress | 1.10E−12 |
| GO:0050896 | P | response to stimulus | 1.60E−12 |
| GO:0009607 | P | response to biotic stimulus | 1.70E−08 |
| GO:0009719 | P | response to endogenous stimulus | 4.00E−05 |
| GO:0009628 | P | response to abiotic stimulus | 0.0027 |
| GO:0008152 | P | metabolic process | 0.0083 |
| GO:0009987 | P | cellular process | 0.022 |

Figures 2, 7:
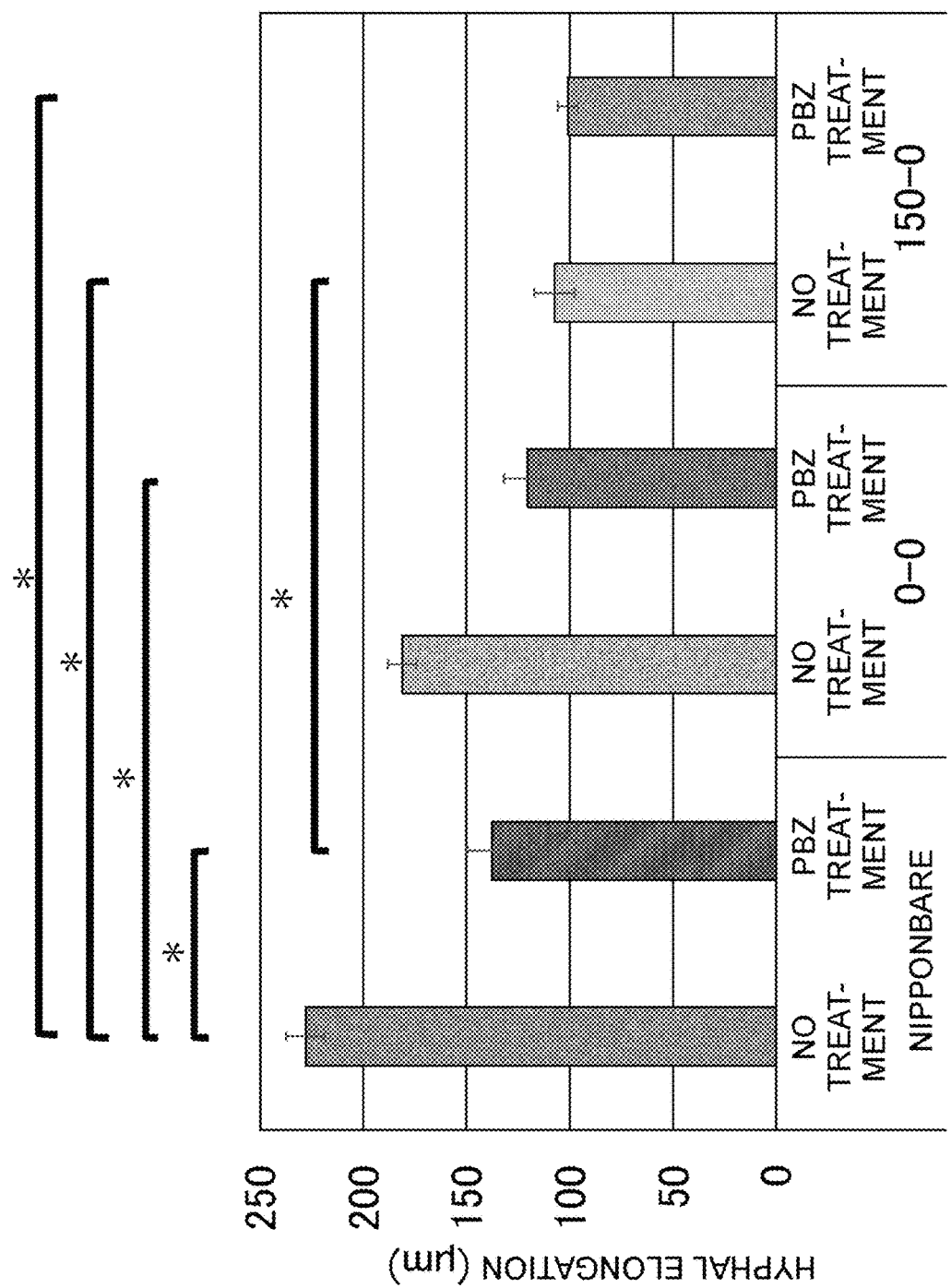
FIG. 2 is a diagram showing that demethylation occurs in a promoter region of a gene having expression increased in a 150-0 line. Only some genes are illustrated. A: Methylation changes in the promoter region of the 304 gene having expression increased in an R-DR line as compared to a 0 line. B, C: Methylation status of promoter regions of LOC_Os05g34270(B) and LOC_Os05g34830(C).
FIG. 7 is a diagram shoring that regenerated line plants (150-0 line) obtained by probenazole-treatment of rice callus in the process of dedifferentiation exhibit resistance to *Xanthomonas oryzae* pv. *oryzae* and exhibit the resistance equal to or higher than that when rice is probenazole-treated (*: P<0.05).

Expression of the defense-related gene WRKY45 in the absence of probenazole in the R-DR rice line is due to epigenetic mutations In the process of producing rice of the R-DR line, even if the probenazole treatment is performed in the process of dedifferentiation or redifferentiation, redifferentiation from callus is not inhibited, and the number of meristems formed in callus and the appearance rate of regenerated plants had no significant difference as compared to the control not treated with probenazole. The regenerated R0 individuals of the R-DR line exhibited significant induction of WRKY45 gene expression even though the individuals were subjected to the inoculation experiment without selection, and all the individuals exhibited significant blast resistance as described later. These results indicate that the gene expression induction and disease resistance observed in the R-DR line were obtained not as a result of selection. On the other hand, probenazole is not known to be mutagenic. Therefore, to investigate the possibility that epigenetic mutations were induced in the R-DR line, we examine whether a change in the DNA methylation state was recognized as compared to Nipponbare in the promoter region of 304 genes including the WRKY45 gene increased in expression in the 150-0 line. As a result, demethylation of the promoter region (particularly the region of 1 kb upstream from the transcription start site) occurred in 30 genes as compared to the original plant, and it was suggested that this demethylation was the cause of the high expression in the 150-0 line rice. See FIG. 2.

These 30 genes were significantly enriched with stress-responsive genes. When the sequences of the promoter regions of Nipponbare and Koshihikari belonging to the Japonica varieties and Bio-226 and Shuhui 498 belonging to the Indica varieties were multiple-aligned, the nucleotide sequences were matched 99 to 100% in the region of 1 kb upstream from the transcription start site, and no insertion sequence was recognized. Comparing the Japonica varieties with the relatively distant Indica varieties, the nucleotide sequences showed 92 to 95% identity, although 1 to 34 nucleotides were inserted or deleted at 1 or 2 locations, and the sequences were extremely strongly preserved (see FIG. 3). Therefore, demethylation of the promoter region confirmed in Nipponbare is expected to occur in the other Japonica varieties and Indica varieties as well.

These results strongly suggest that by inducing the expression of gene(s) of interest in the process of dedifferentiation or redifferentiation of rice callus, imprinting occurs in the gene(s) in the process of regeneration of plants and the epigenetic state was artificially oriented.

The R-DR rice line exhibits resistance to blast in the absence of probenazole.

To confirm whether the R-DR line acquired disease resistance, the strength of resistance was examined by inoculating the leaf sheath with GFP-expressing blast fungus in the absence of probenazole. The regenerated rice lines (0-0 line) not treated with probenazole in the process of dedifferentiation or redifferentiation exhibited hyphal elongation of blast fungus similar to that of Nipponbare in all the individuals. On the other hand, in the R-DR line, regardless of the timing and concentration of the probenazole treatment, the hyphal elongation of blast fungus was significantly suppressed in the leaf sheaths of all the lines as compared to the parental variety Nipponbare, and acquisition of blast resistance was exhibited. All the R-DR lines exhibited significant blast resistance, and particularly, all of the regenerated individuals (50-0 lines) obtained by 50 µM probenazole treatment on the rice dedifferentiation-inducing medium exhibited significant resistance. See FIG. 4. The same results were obtained from the 100-0 and 150-0 lines (data not shown).

Figure 5:
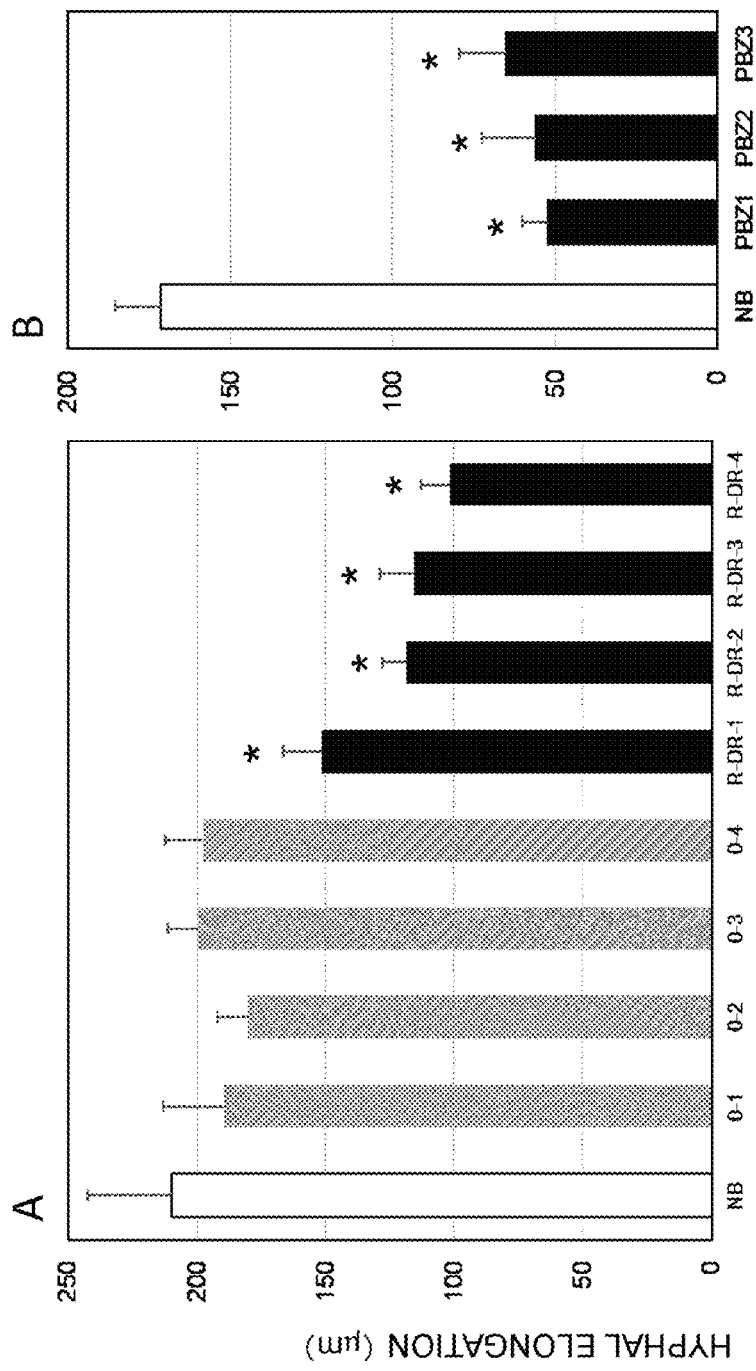
FIG. 5 is a diagram shoring that the blast resistance of the R-DR line is inherited up to a third generation (R2) through passage or subculture. A: As compared to Nipponbare (NB) and the progeny (third generation) of the line regenerated without a resistance inducer treatment (0-X), the progeny of the R-DR line regenerated with a resistance inducer treatment (R-DR-X) inhibited hyphal elongation of rice blast fungus in the leaf sheath, and exhibited a significant blast resistance as compared to Nipponbare (P<0.05), and the acquired resistance was maintained. The last number indicative of the lineage denotes the number of independently regenerated individuals. B: The hyphal elongation of rice blast fungus was inhibited in the rice leaf sheath treated with a resistance inducer, and a significant blast resistance was exhibited (P<0.05).

Furthermore, when the blast resistance of the third generation (R2) of these lines was confirmed, the hyphal elongation of blast fungus in the leaf sheath was suppressed in all the lines, and significant blast resistance was exhibited. The blast resistance exhibited by these R-DR lines was almost as strong as the resistance induced by the probenazole treatment of rice plants. As compared to Nipponbare and the 0-0 line, the 50-0 line suppressed the expansion of blast lesions on the leaf blades, and resistance was clearly confirmed. See FIG. 5. The same results were obtained from the 100-0 and 150-0 lines (data not shown).

Figure 6:
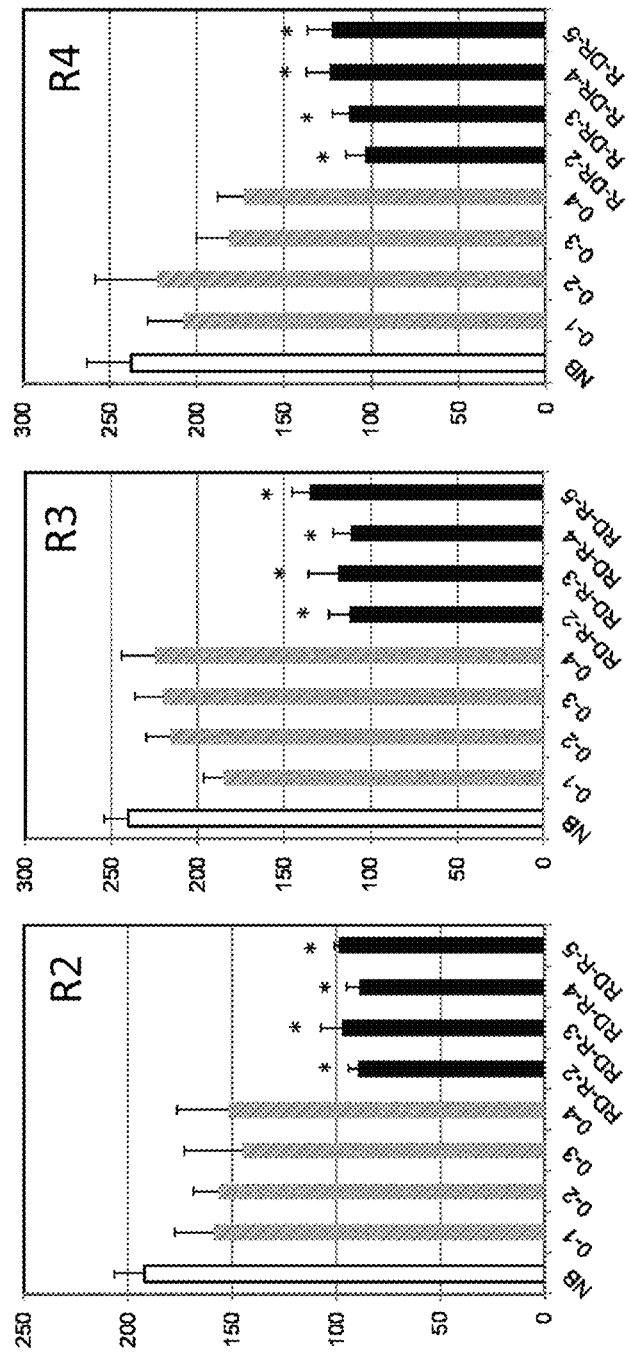
FIG. 6 is a diagram shoring that the blast resistance of the R-DR line is inherited even after the third generation (R2) through passage or subculture. As compared to Nipponbare (NB) and the progeny (R2 to R4) of the line (0-X) regenerated without the resistance inducer treatment, the progeny of the R-DR line (R-DR-X) inhibited the hyphal elongation of rice blast fungus in the leaf sheath, and exhibited a significant blast resistance as compared to Nipponbare (P<0.05), and the acquired resistance was stably inherited up to at least the fifth generation. The last number indicative of the lineage denotes the number of independently regenerated individuals.

Since the hyphal elongation of blast fungus in the leaf sheath was significantly suppressed in the same way also in the third to fifth generations (R2 to R4) of the 150-0 line, the blast-resistant rice line produced by inducing the WRKY45 gene expression by probenazole treatment of callus in the process of dedifferentiation or redifferentiation of rice probably acquired genetically stable resistance in which the resistance phenotype is maintained even after multiple sexual generations. See FIG. 6.

The R-DR rice line shows resistance to Xanthomonas oryzae in the absence of probenazole To confirm whether the R-DR line acquired resistance to bacteria other than blast fungus, the strength of resistance was examined by inoculating the leaf sheath with Xanthomonas oryzae in the absence of probenazole. The regenerated rice lines (0-0 line) not treated with probenazole in the process of dedifferentiation or redifferentiation exhibited hyphal elongation of Xanthomonas oryzae similar to that of Nipponbare in all the individuals. On the other hand, in the 150-0 line, the hyphal elongation of Xanthomonas oryzae was significantly suppressed as compared to the parental variety Nipponbare, and acquisition of rice white leaf blight resistance was exhibited. The resistance to Xanthomonas oryzae exhibited by the 150-0 line was equal to or higher than the resistance induced by probenazole treatment of rice plant bodies. See FIG. 7.

Example 2

Production of Disease-Resistant Nicotiana benthamiana Line by Probenazole Treatment of Nicotiana benthamiana Callus and Genetic Stability of Disease Resistance Phenotype Materials and Methods Plant Nicotiana benthamiana was used as the plant. Seeds of Nicotiana benthamiana were sown in nursery soil (TAKII & CO., LTD.) and cultivated in an artificial weather chamber at 25° C. with a 16-hour dark period and an 8-hour light period for 3 weeks.

Fungus and Bacterium

Botrytis cinerea was used as the pathogenic filamentous fungus of Nicotiana benthamiana, and Pseudomonas syringae pv. tabaci was used as the pathogenic bacterium.

For Botrytis cinerea, Botrytis cinerea stored on the PDA slope medium was inoculated on the PDA flat medium and cultured at 25° C. for 7 days. Fungus bodies were cut out along with the medium from the hyphae extending on the surface of the medium with a cork borer having an inner diameter of 4 mm and inoculated into a new PDA flat medium. The fungus bodies were cultured at 25° C. for 5 days, and then cultured at 25° C. for 3 days under BL lamp irradiation to form spores. Sterilized water was poured onto the surface of the PDA flat medium on which spores of Botrytis cinerea were formed, and the spores were scraped off with a bacteria spreader to prepare a spore suspension. The spore suspension was centrifuged at 2000×g for 2 minutes at room temperature to remove supernatant, and 1/2PDB (1.2 g of Potate Dextrose Broth, 100 ml of distill water) medium was added to achieve the spore suspension concentration of $1.0 \times 10^6$ spores/ml to adjust the spore suspension for use in the inoculation test.

Preserved P. syringae bacteria were inoculated with a platinum loop on a King's B medium [King 1954] and cultured at 37° C. for about 24 hours. Single colonies formed on the medium were transferred to 4 ml of King's B liquid medium in a 15 ml Nunc tube with a sterile toothpick. The bacteria were cultured in a rotary shaker under the conditions of 28° C. and 100 rpm for about 48 hours, and the bacteria cells collected by centrifugation (2000×g, 10 min) were suspended in a 10 mM $MgCl^2$ solution to $OD_{600}=1.0$ ($10^8$ cells/ml) and used for the inoculation experiment.

Media, etc.

The composition of the tobacco dedifferentiation-inducing medium is as follows.

TABLE 7

| Tobacco Dedifferentiation-Inducing Medium | |
|---|---|
| Sucrose | 30 g/L |
| MS Basal MD | 4.3 g/L |

TABLE 7-continued

| Tobacco Dedifferentiation-Inducing Medium | |
|---|---|
| inositol | 100 mg/L |
| nicotinic acid | 0.5 mg/L |
| Acetic acid pyridoxine | 0.5 mg/L |
| Thiamine hydrochloride | 0.1 mg/L |
| L glycine | 2.0 mg/ml |
| 1 mg/mg IAA | 2 ml/L |
| 1 mg/ml 6-BA | 1 ml |
| Gelrite | 3.5 g |

Autoclave: 121° C., 20 minutes

The composition of the tobacco shoot-inducing medium is as follows.

TABLE 8

| Tobacco Shoot-Inducing Medium | |
|---|---|
| Sucrose | 30 g/L |
| MS Basal MD | 4.3 g/L |
| Inositol | 100 mg/L |
| Nicotinic acid | 0.5 mg/L |
| Acetic acid pyridoxine | 0.5 mg/L |
| Thiamine hydrochloride | 0.1 mg/L |
| L glycine | 2.0 mg/ml |
| 1 mg/ml IAA | 1 ml |
| 1 mg/ml 6-BA | 2 ml |
| 1 mg/ml kinetin | 2 ml |

Autoclave: 121° C., 20 minutes

The composition of the tobacco rooting medium is as follows.

TABLE 9

| Tobacco Rooting Medium | |
|---|---|
| Sucrose | 30 g/L |
| MS Basal MD | 4302.09 mg/L |
| Gelrite | 3.0 g/L |

Autoclave: 121° C., 20 minutes

Induction of Expression of Defense-Related Gene WRKY45 in *Nicotiana benthamiana* Callus

*Nicotiana benthamiana* was used as a plant material to be evaluated. Leaves are cut from the plant, and a leaf piece having a size of about 5 mm×5 mm was placed on the tobacco dedifferentiation-inducing medium and cultured in a 16-hour light-period artificial weather apparatus at 25° C. and 40 μmol photon/m$^2$s until callus is formed (see Non-Patent Document 14).

The formed callus was transplanted to a new tabaco dedifferentiation-inducing medium or a tabaco dedifferentiation-inducing medium (Table 10) to which Oryzemate granules (containing 24% probenazole as an active ingredient; Meiji Seika Pharma Co., Ltd.; the Ministry of Agriculture, Forestry and Fisheries registration No. 19541) were added so that the final concentration of probenazole known to induce expression of the defense-related gene WRKY45 (Non-Patent Document 10) was 200 μM, and was cultured in a growth chamber under the same conditions for 7, 14, or 21 days. It is known that probenazole induces the expression of defense-related genes such as WRKY45 through activation of the salicylic acid pathway of *Nicotiana benthamiana* and imparts resistance to *Botrytis cinerea* and *Pseudomonas syringae* pv. *tabaci* to *Nicotiana benthamiana*. (Non-Patent Document 10).

TABLE 10

| PBZ-Added Tobacco Dedifferentiation-Inducing Medium | |
|---|---|
| Sucrose | 30 g/L |
| MS Basal MD | 4.3 g/L |
| Inositol | 100 mg/L |
| Nicotinic acid | 0.5 mg/L |
| Acetic acid pyridoxine | 0.5 mg/L |
| Thiamine hydrochloride | 0.1 mg/L |
| L glycine | 2.0 mg/ml |
| Probenazole | 0.2 mM |
| NAA (1 mg/ml of Ethanol) | 0.2 ml/L |
| Kinetinm(0.1 mg/ml) | 20 ml |
| Gelrite | 3.0 g/L |

Autoclave: 121° C., 20 minutes

The callus grown on the medium was transplanted to the tobacco shoot-inducing medium (tobacco redifferentiation-inducing medium) and cultured in a growth chamber under the same conditions until shoots were formed.

The redifferentiated shoots were transferred to the tobacco rooting medium in a plant box and cultivated in a growth chamber under the same conditions until 3 weeks elapsed after rooting, and the formed plants were transplanted to the nursery soil.

Evaluation of Disease Resistance of *Nicotiana benthamiana*

Inoculation of *Botrytis cinerea* to *Nicotiana benthamiana* and evaluation of resistance were performed by the following method. By using a perforator, a piece of filter paper (No. 1, Advantech Toyo, Tokyo) having a diameter of 6 mm was cut out and divided into 4 equal parts to make paper disks for inoculation. One of the inoculation paper disks was placed on a leaf surface of a 5-week-old *Nicotiana benthamiana* or a regenerated individual grown to the equivalent size (leaf diameter of about 5 cm), and 5 μl of the spore suspension was dropped on the disk with a micropipettor. After inoculation with *Botrytis cinerea*, the leave was cultured in a growth chamber at 22° C. for 24, 48, and 72 hours. The leaf with a lesion formed thereon was recorded as a digital image by an image scanner (GT-X970, Epson), and the lesion area was measured by using the image analysis software ImageJ.

Inoculation of *Nicotiana tabacum* leaves with *Pseudomonas syringae* pv. *tabaci* and evaluation of resistance were performed by the following method. The *P. syringae* suspension was transferred to a 1.5 ml tube and diluted with a 10 mM $MgCl_2$ solution to $10^4$ cells/ml. A leave of 5-week-old *Nicotiana benthamiana* or a regenerated individual grown to the equivalent size (leaf diameter of about 5 cm) was cut out and placed in a 15 cm square petri dish, inoculated by injection of the bacterial solution with a 1 ml needleless syringe, and cultured in a growth chamber for 5 days while maintaining the inside of the square petri dish as a moist chamber. After culturing, the inoculated site of the leave was cut with a cork borer having a diameter of 1 cm, placed in a 2 ml tube with quartz sand, glass beads, and 1 ml of a 10 mM $MgCl_2$ solution, and ground by using Fast-Frep (RP120; Thermo Fisher Scientific, US). A 10-fold dilution series was prepared from the grinding solution, 100 μl was inoculated into a King's B medium, cultured at 37° C. for 2 days, and colonies were then counted. The colony forming unit (CFU) per ml was calculated from the dilution rate and the number of colonies.

Results and Discussion

*Nicotiana benthamiana* line of callus treated with probenazole exhibits disease resistance in the absence of probenazole.

To investigate whether imparting of disease resistance by artificial orientation of the epigenetic state demonstrated in rice is applicable to other plants, experiments were conducted by using the dicotyledonous *Nicotiana benthamiana* widely used in the study of plant-pathogenic interactions. As with rice, *Nicotiana benthamiana* was treated with probenazole for 7 to 21 days in the process of dedifferentiation or redifferentiation, and the resistance of regenerated plants to *Botrytis cinerea* was examined. As a result, the expansion of lesions of *Botrytis cinerea* was significantly suppressed in the current generation (R0) of regenerated *Nicotiana benthamiana* of callus treated with probenazole, as compared to the wild type. Significant *Botrytis cinerea* resistance was also observed in R1, which is the self-fertilized progeny of R0, and it was clarified that the disease resistance phenotype was maintained in *Nicotiana benthamiana* even after sexual reproduction. Furthermore, in the R0 plant of *Nicotiana benthamiana* of callus treated with probenazole, the growth of *Pseudomonas syringae* pv. *tabaci* is markedly suppressed, and it was found that the plant exhibit resistance not only to filamentous fungal disease but also to bacterial disease. See FIG. 8.

These results strongly suggest that in the dicotyledonous *Nicotiana benthamiana* as well as the monocotyledonous rice, by inducing the expression of gene(s) of interest in the process of dedifferentiation or redifferentiation of rice callus, imprinting occurs in the gene(s) in the process of regeneration of plants, and the epigenetic state having disease-resistant priming imprinted therein was artificially oriented. Therefore, it was demonstrated that the method for producing a non-natural plant of the present invention can be applied to a wide range of plants.

Example 3

Production of Low Temperature Resistant Rice Line by Low-Temperature Treatment of Rice Callus and Genetic Stability of Low Temperature Resistant Phenotype
Materials and Methods
Plant
The same Nipponbare as in Example 1 was used.
Culture Media
The same media as in Example 1 were used.
Induction of Expression of Low Temperature Resistant Gene by Low-Temperature Treatment of Rice Callus
Rice (*Oryza sativa* cv. *Nipponbare*; Rice variety: Nipponbare) was used as the plant material to be evaluated. Rice callus induction (dedifferentiation induction) was performed in the same manner as in Example 1.

The callus grown on the rice dedifferentiation-inducing medium was placed on a new rice dedifferentiation-inducing medium and cultured in an artificial weather chamber at 28° C. or a low temperature chamber at 4° C. for 7 days in the 24-hour light period. It is known that a low-temperature treatment of rice induces expression of the genes encoding AP2 domain-containing proteins (LOC_Os09g28440, LOC_Os09g35020, LOC_Os10g41330), the gene encoding the ethylene response transcription factor (LOC_Os02g54050), the WRKY24 gene (LOC_Os01g61080), the gene encoding the helix-loop-helix DNA-binding domain-containing protein (LOC_Os03g53020), the genes encoding MYB family transcription factors (LOC_Os04g43680, LOC_Os06g51260), etc. (Non-Patent Document 15).

To regenerate the callus into a rice plant body, the callus grown on the medium was transplanted to the rice redifferentiation-inducing medium and cultured in a 24-hour light period artificial weather apparatus at 28° C. until shoots were formed. The redifferentiated shoots were transferred to the rice rooting medium in a plant box and cultured in a growth chamber under the same conditions for 2 to 3 weeks until rooted plants were formed. The regenerated rice plants were transferred to cultivation soil and acclimated to the outside air in a plastic cup (diameter: 8 cm, depth: 12 cm). After the acclimatization treatment, the plants were transplanted to a cell tray, kept in a state of being constantly filled with ion-exchanged water on a water receiver, and grown at a room temperature of 28° C. Seeds obtained by self-propagation of the obtained regenerated rice individuals (R0) of the current generation were referred to as R1 seeds. Rice lines obtained by culturing rice callus at 4° C. or 28° C. for 7 days in a dedifferentiated state as described above for regeneration into plants are respectively referred to as a 7d-4 line or a 7d-28 line.
Comprehensive Analysis of Rice Gene Expression
Comprehensive analysis of rice gene expression of the 7d-4 line and the 7d-28 line was performed by the same method as in Example 1.
Evaluation of Low Temperature Resistance of Rice After a sterilizing treatment, the rice seeds were spread to be evenly immersed in sterilized water and were subjected to a sprouting treatment in a growth chamber at 28° C. under bright conditions for 3 days. Subsequently, 1 grain was sown in each cell of a cell tray containing soil to which 1 g of ammonium sulfate, 1.5 g of superphosphate, and 0.2 g of potassium chloride per 7.5 kg of vermiculite was applied. The cell tray was placed on a water receiver and cultivated in an artificial weather chamber at a day temperature of 30° C. and a night temperature of 25° C. with a 14-hour light period.

After treating 1-week-old rice in the dark at 4° C. for 1 week, recovery treatment was performed for 2 weeks in an artificial weather chamber under the same conditions. After the recovery process, SES (Standard Evaluation System) and survival rate were measured. SES is an evaluation standard developed by the International Rice Research Institute IRRI, and a state of plants is visually confirmed, and the state is evaluated with a score of 1 to 9 (IRRI 2002). When the state of plants is worse, the value becomes higher, the plant growing well is defined as 1, and the dead condition is defined as 9 (Table 11).

The survival rate was calculated by the following equation, regarding individuals having SES after recovery treatment determined to be 9 as dead individuals.

Survival rate=(the total number of individuals−the number of dead individuals)/the total number of individuals (%)

TABLE 11

Standard Evaluation System for Rice (SES)

SCALE

1 Plants have a normal color; rate of growth and flowering normal
3 Plants slightly stunted; growth slightly retarded
5 Plants moderately stuned, leaves yellowish and development delayed
7 Plants severely stuned, leaves yellow and development delayed, and panicles poorly exserted
9 Plants severely stunted, with leaves brown, development much delayed and panicles not exserted Results and Discussion
In the 7d-4 rice line, a gene group induced to be expressed in callus by low-temperature treatment at 4° C. was induced to be expressed under the growth condition of 28° C.

Comparing the phenotypes between the 7d-4 line and Nipponbare, no difference was recognized in the visible phenotype or the yield in the field. Additionally, no difference was recognized in the survival rate of callus between the callus cultured at 4° C. and the control (28° C. cultured) callus (the survival rate was 100% in both cases).

To confirm whether the expression of the cold-induced gene induced to be expressed in rice callus is maintained in the 7d-4 line, the gene expression was comprehensively investigated by RNA-seq analysis, and transcriptome was compared between the 7d-4 line and the 7d-28 line.

As a result, in the 7d-4 line, even under the growth condition of 28° C., significant changes in expression occurred in 129 genes including the gene encoding the AP2 domain-containing protein, the gene encoding the ethylene response transcription factor, the WRKY24 gene, the gene encoding the helix-loop-helix DNA-binding domain-containing protein, and the gene encoding the MYB family transcription factor. Gene ontology analysis of these gene sets revealed that the genes involved in the stress response and the gene group having the functions of transcription factors were significantly enriched (Table 12).

when an overlapping relationship was investigated between 84 genes significantly increased in expression in plants to which low temperature resistance was imparted and genes increased in expression in the low-temperature-treated callus, 47 of the 84 genes were identical, and the genes increased in expression in the low-temperature-treated callus were significantly more included (P<2.2e−16).

The 7d-4 rice line exhibits low temperature resistance.

Since the expression of multiple known low-temperature responsive transcription factors was induced in the 7d-4 rice line, it was examined whether the 7d-4 rice line has low-temperature resistance. R1 plants were low-temperature-treated for Nipponbare, the 7d-28 line, and the 7d-4 line (all n=3), and SES and survival rates were measured. After low-temperature treatment, Nipponbare and 7d-28 lines had SES of about 9, and most of them died. In contrast, in the 7d-4 line, 2 out of 3 individuals showed significantly lower SES values than Nipponbare and the 7d-28 line. Similarly, regarding the survival rate, Nipponbare and 7d-28 lines had 5 to 15%, while the 7d-4 line had a high value of 40 to 60%. See FIG. 9. The above results suggest that the 7d-4 line

TABLE 12

| GO_acc | term_type | | queryitim | bgitem | FDR |
|---|---|---|---|---|---|
| GO: 0006950 | p | response to stress | 38 | 3615 | 1.7E−07 |
| GO: 0050896 | p | response to stimulus | 40 | 5265 | 0.012 |
| GO: 0030528 | F | transcription regulator activity | 18 | 1773 | 0.013 |
| GO: 0003676 | F | transcription factor activity | 18 | 1773 | 0.013 |

Among the genes encoding transcription factors, 14 genes having expression increased in the 7d-4 line as compared to the 7d-28 line are all included in the low temperature responsive transcription factors reported in Non-Patent Document 15 (Table 13).

acquired low temperature resistance by the low-temperature treatment of callus. As described above, since the survival rate of callus cultured at 4° C. for 7 days was 100%, this indicates that the low temperature resistance of the 7d-4 line was acquired not as a result of selection.

TABLE 13

| Locus Number | Annotation | Cold responsive gene* |
|---|---|---|
| LOC_Os01g60600 | WRKY108, expressed | yes |
| LOC_Os01g60640 | WRKY21, expressed | yes |
| LOC_Os01g61080 | WRKY24, expressed | yes |
| LOC_Os02g45450 | dehydration-responsive element-binding protein, putative, expressed | yes |
| LOC_Os02g54050 | ethylene-responsive transcription factor, putative, expressed | yes |
| LOC_Os03g09170 | ethylene-responsive transcription factor, putative, expressed | yes |
| LOC_Os03g32230 | ZOS3-12-C2H2 zinc finger protein, expressed | yes |
| LOC_Os03g53020 | helix-loop-helix DNA-binding domain containing protein, expressed | yes |
| LOC_Os04g43680 | MYB family transcription factor, putative, expressed | yes |
| LOC_Os06g51260 | MYB family transcription factor, putative, expressed | yes |
| LOC_Os09g28440 | AP2 domain containing protein, expressed | yes |
| LOC_Os09g35010 | dehydration-responsive element-binding protein, putative, expressed | yes |
| LOC_Os09g35020 | AP2 domain containing protein, expressed | yes |
| LOC_Os10g41330 | AP2 domain containing protein, expressed | yes |

*See, Yang et al. (2015), S2 TABLE.

Comparison of Gene Group Increased in Expression in Plants with Epigenetic Mutation Oriented by Low-Temperature Treatment and Gene Group Increased in Expression in Low-Temperature-Treated Callus The stress tolerance-related genes were significantly enriched among the 84 genes increased in expression in plants to which low temperature resistance was imparted due to the orientation of epigenetic mutations. Furthermore, In addition, the two 7d-4 lines exhibiting low temperature resistance clearly exhibited low temperature resistance in the produced next-generation R1 as compared to the 7d-28 line, and therefore, it was strongly indicated that the phenotype of low temperature resistance is maintained even through sexual reproduction. Therefore, it was demonstrated that the method for producing a non-natural plant of the present invention can be performed not only by using a chemical stimulus such as probenazole treatment but also by using a physical stimulus such as low temperature.

Example 4

Orientation of Epigenetic Mutation by Salt Treatment of Rice Callus
Materials and Methods
Plant
The same Nipponbare as in Example 1 was used.
Media
The same media as in Example 1 were used.
Rice seeds were cultured in the same manner as probenazole treatment to induce callus. The callus grown on the medium was transplanted onto a new N6D medium or onto an N6D medium to which sodium chloride was added to a final concentration of 100 and 200 mM, and was cultured in a 24-hour light-period artificial weather apparatus at 26° C. and 60 μmol photon/m$^2$s for 7 days. It is known that a salt treatment of rice induces expression of the gene LOC_Os05g48700 presumably encoding gibberellin 2β dioxygenase (Non-Patent Document 16), the gene LOC_Os05g38530 presumably encoding the DnaK family protein (Non-Patent Document 17), the gene LOC_Os01g64360 presumably encoding the MYB family transcription factor and the gene LOC_Os02g52670 encoding the AP2 domain-containing protein (Non-Patent Document 18), and the gene LOC_Os08g29660 encoding WRKY69 (Non-Patent Document 19). To regenerate the callus into a rice plant body, the callus grown on the medium was transplanted to a redifferentiation medium (Appendix Table 2) and cultured in a growth chamber under the same conditions until shoots were formed. The redifferentiated shoots were transferred to the rooting medium in a plant box and cultured in a growth chamber under the same conditions for 2 to 3 weeks until rooting is followed by formation of infant plants. The regenerated rice infant plants were transplanted into cultivation soil and acclimatized to the outside air in a plastic cup (diameter: 8 cm, depth: 12 cm). After the acclimatization treatment, the plants were transplanted to a cell tray, kept in a state of being constantly filled with ion-exchanged water on a water receiver, and grown at a room temperature of 28° C. Seeds obtained by self-propagation of the obtained regenerated rice individuals (R0) of the current generation were referred to as R1 seeds.
Results and Discussion
Imparting Salt Resistance to Rice by Orientation of Epigenetic Mutation
Seeds of Nipponbare (NB), the line regenerated without treatment (Na-0), and the second generation (R1) of the line (Na-100) regenerated under 100 mM NaCl treatment were cultured for 7 days on 0.7% agar to which 100 mM NaCl was added, and a root elongation amount was measured (n=5) (see FIG. 10). Roots were significantly elongated in Na-100 as compared to NB and Na-0. **: Significant difference from NB exists at 1% level according to Dunnett's test.
Gene Expression in Plants Having Acquired Salt Resistance by Orientation of Epigenetic Mutations
Callus was treated with 200 mM NaCl by the same method as the probenazole treatment and the low-temperature treatment, and the gene expression in the regenerated plants was examined by RNA-seq. As a result, the expression of 1,038 genes was significantly changed as compared to a control plant regenerated without low-temperature treatment, and 753 genes out of them were significantly increased in expression (FDR<0.05). As a result of Gene Ontology Enrichment analysis of these 753 genes, stimulus-responsive and abiotic stress-responsive genes were significantly enriched.

Furthermore, when an overlapping relationship was investigated for the gene groups increased in expression in the plants imparted with disease resistance, low temperature resistance, and salt resistance, the overlap between the respective groups was small. Since the overlap was small although stress-responsive genes were significantly enriched in all the gene groups according to Gene Ontology Enrichment analysis, it is strongly suggested that the epigenetic mutations were adaptively oriented to the applied stress by the epigenetic mutation orientation treatment.

Example 5

Figure 11:
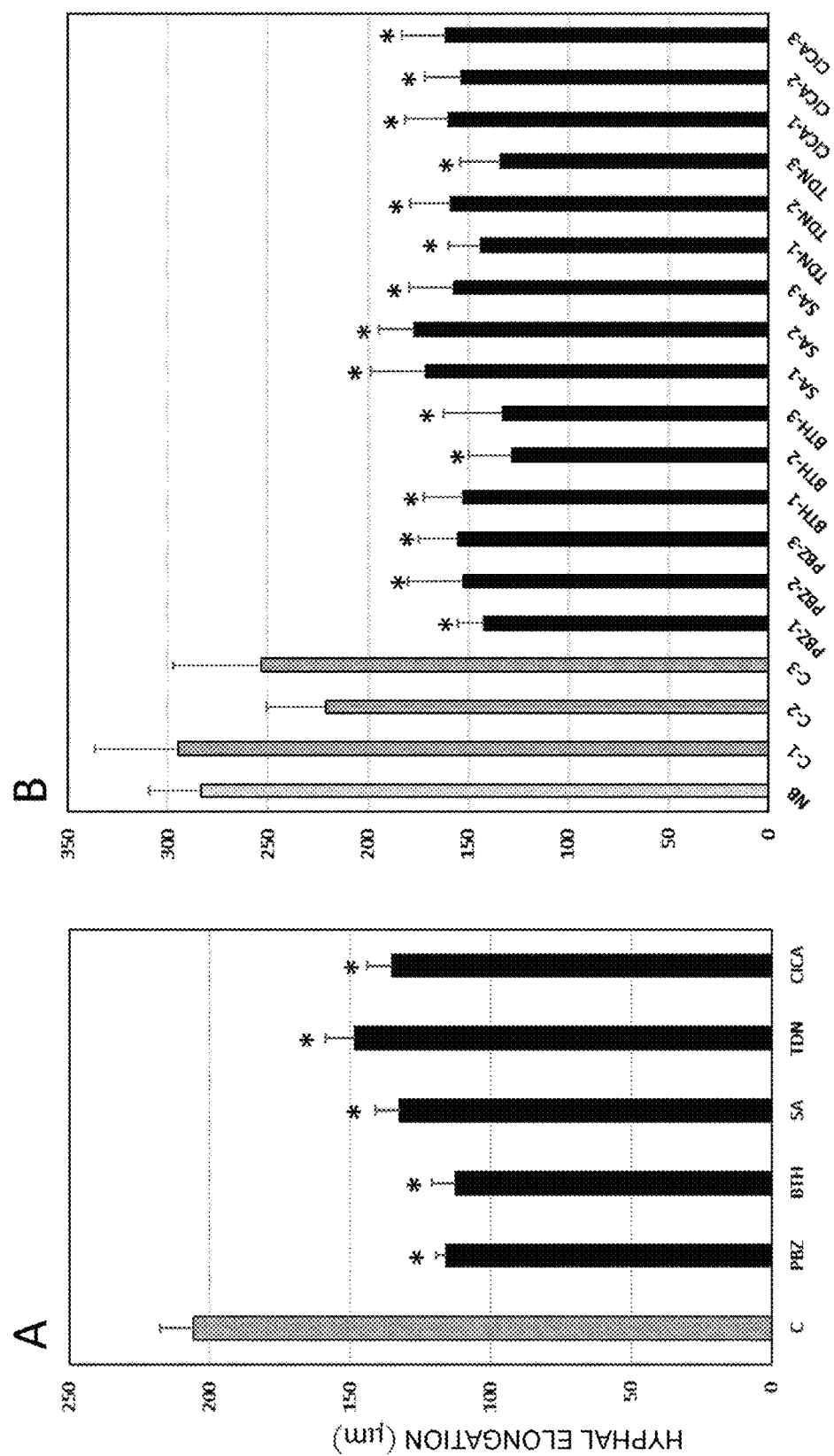
FIG. 11 is a diagram showing that regenerated line plants treated with a resistance inducer other than probenazole in the process of dedifferentiation/redifferentiation acquire blast resistance. A: As compared to a control individual (C) regenerated without treatment with the resistance inducer, the regenerated individuals regenerated with resistance inducers (PBZ: 150 μM probenazole-treated individual, BTH: 150 μM acibenzolar S methyl-treated individual, SA: 1 mM salicylic acid-treated individual, TDN: 150 μM tiadinil-treated individual, CICA: 150 μM isothianil-treated individual) inhibited hyphal elongation of rice blast fungus in the leaf sheath and exhibited a significant blast resistance (P<0.05). B: As compared to Nipponbare (NB) and the progeny (third generation; R2) of the line regenerated without resistance inducer treatment (C), the progenies (R2) of the lines treated with the resistance inducers (PBZ-X: 150 μM probenazole-treated line, BTH-X: 150 μM acibenzolar S methyl-treated line, SA-X: 1 mM salicylic acid-treated line, TDN-X: 150 μM tiadinil-treated line, CICA-X: 150 μM isothianil-treated line) inhibited hyphal elongation of rice blast fungus in the leaf sheath, and exhibited a significant blast resistance as compared to Nipponbare (P<0.05), and the acquired resistance was inherited to progeny. The last number indicative of the lineage denotes the number of independently regenerated individuals.

Orientation of Epigenetic Mutation by Resistance Inducers Other than Probenazole
Materials and Methods
Plant
The same Nipponbare as in Example 1 was used.
Media
The same media as in Example 1 were used.
We used acibenzolar S-methyl (BTH), tiadinil (TDN) and isotianil (CICA), which are resistance inducers considered to activate the salicylic acid pathway as with probenazole (PBZ), and salicylic acid (SA), which is a disease-responsive plant hormone.
The resistance inducers are considered to have different points of action in the salicylic acid pathway, and it is known that probenazole acts upstream of salicylic acid (Non-Patent Document 20), that acibenzolar S-methyl is a functional analog of salicylic acid (Non-Patent Document 21, Non-Patent Document 22), that tiadinil acts downstream of salicylic acid, and that isotianil acts upstream and downstream of salicylic acid (Non-Patent Document 23, Non-Patent Document 21).
Callus was transplanted onto a rice dedifferentiation-inducing medium to achieve 150 μM for acibenzolar S-methyl (Bion wettable powder; containing 50% acibenzolar S-methyl; Syngenta Japan; Ministry of Agriculture, Forestry and Fisheries registration expired), 150 μM for tiadinil (V-GET flowable; containing 30% tiadinil; Nihon Nohyaku Co., Ltd.; Ministry of Agriculture, Forestry and Fisheries Registration No. 21298), 150 μM for isotianil (routine FS; containing 18% isotianil; Bayer Crop Science; Ministry of Agriculture, Forestry and Fisheries Registration No. 23424), or 1 mM for Sodium Salicylate (FUJIFILM Wako Pure Chemical Corporation), and cultured in a growth chamber.
Results and Discussion
Regenerated lines treated with resistance inducers other than probenazole treatment in the process of dedifferentiation/redifferentiation acquire blast resistance.
The blast resistance was evaluated by the same method as the plants produced with probenazole. Regenerated individuals regenerated with probenazole (PBZ), acibenzolar S-methyl (BTH), salicylic acid (SA), tiadinil (TDN), or isotianil (CICA) prohibited the hyphal elongation of *Magnaporthe oryzae* in the leaf sheath and exhibited significant disease resistance (P<0.05) (FIG. 11A). The acquired blast resistance was inherited in the progeny (third generation; R2) (FIG. 11B).
These results suggest that the phenomenon observed in the plants produced by probenazole treatment is also observed in the regenerated line plants treated with other resistance inducers.

Example 6

Production of Disease-Resistant Tomato Line by Probenazole Treatment of Tomato Callus Materials and Methods Plant Tomato (*Solanum lycopersicum*; tomato variety: Micro-Tom) was used. Tomato seeds were sterilized and then sown in a tomato germination medium and cultivated in an artificial weather chamber at 25° C. with a 16-hour dark period and 8-hour light period for 7 to 10 days.

Fungus

*Botrytis cinerea* was used as the pathogenic filamentous fungus of tomatoes. The spore suspension used in the inoculation test was prepared in the same manner as in Example 2.

Production of Regenerated Tomato Plants

A tip of a cotyledon was cut and discarded, and the remaining cotyledon was cut perpendicular to the veins into two equal parts. The cotyledon sections were placed on a tomato dedifferentiation-inducing medium and cultured at 25° C., 40 μmol photon/m$^2$s, in a 16-hour light-period artificial weather apparatus for 1 week to induce callus. The formed callus was transplanted to a new tomato dedifferentiation-inducing medium or a tomato dedifferentiation-inducing medium (Table PBZ-added tomato dedifferentiation-inducing medium) to which Oryzemate granules (containing 24% probenazole as an active ingredient; Meiji Seika Pharma Co., Ltd.; the Ministry of Agriculture, Forestry and Fisheries registration No. 19541) were added so that the final concentration of probenazole known to induce expression of the defense-related gene WRKY45 (Non-Patent Document 10) was 200 μM, and was cultured in a growth chamber for 1 to 2 weeks. After the treatment, the callus was transferred to a tomato shoot-inducing medium, and the regenerated plants were transferred to a tomato rooting medium. Rooted tomatoes were sown in nursery soil (TAKII & CO., LTD.) and cultivated in an artificial weather chamber at 25° C. with a 16-hour dark period and an 8-hour light period. Ripe fruits were harvested, and seeds were collected.

Media, etc.

The composition of the tomato germination medium is as follows.

TABLE 14

| Tomato Germination Medium | |
|---|---|
| Sucrose | 15 g/L |
| MS Basal MD | 4.3 g/L |
| Myo-inositol | 100 mg/L |
| nicotinic acid | 0.5 mg/L |
| Acetic acid pyridoxine | 0.5 mg/L |
| Thiamine hydrochloride | 0.1 mg/L |
| L glycine | 2.0 mg/ml |
| Gelrite | 3 g |

Autoclave: 121° C., 20 minutes

The composition of the tomato dedifferentiation-inducing medium is as follows.

TABLE 15

| Tomato Dedifferentiation-Inducing Medium | |
|---|---|
| Sucrose | 30 g/L |
| MS Basal MD | 4.3 g/L |
| Inositol | 100 mg/L |
| nicotinic acid | 0.5 mg/L |

TABLE 15-continued

| Tomato Dedifferentiation-Inducing Medium | |
|---|---|
| Acetic acid pyridoxine | 0.5 mg/L |
| Thiamine hydrochloride | 0.1 mg/L |
| L glycine | 2.0 mg/ml |
| Trans-Zeatin | 1.5 mg/L |
| Gelrite | 3 g |

Autoclave: 121° C., 20 minutes

The composition of the tomato shoot-inducing medium is as follows.

TABLE 16

| Tomato Shoot-Inducing Medium | |
|---|---|
| Sucrose | 30 g/L |
| MS Basal MD | 4.3 g/L |
| Inositol | 100 mg/L |
| nicotinic acid | 0.5 mg/L |
| Acetic acid pyridoxine | 0.5 mg/L |
| Thiamine hydrochloride | 0.1 mg/L |
| L glycine | 2.0 mg/ml |
| Trans-Zeatin | 1 mg/L |
| Gelrite | 3 g |

Autoclave: 121° C., 20 minutes

The composition of the tomato rooting medium is as follows.

TABLE 17

| Tomato Rooting Medium | |
|---|---|
| Sucrose | 30 g/L |
| MS Basal MD | 4.3 g/L |
| Inositol | 100 mg/L |
| nicotinic acid | 0.5 mg/L |
| Acetic acid pyridoxine | 0.5 mg/L |
| Thiamine hydrochloride | 0.1 mg/L |
| L glycine | 2.0 mg/ml |
| Gelrite | 3 g |

Autoclave: 121° C., 20 minutes

The composition of the PBZ-added tomato dedifferentiation-inducing medium is as follows.

TABLE 18

| PBZ-Added Tomato Dedifferentiation-Inducing Medium | |
|---|---|
| Sucrose | 30 g/L |
| MS Basal MD | 4.3 g/L |
| Inositol | 100 mg/L |
| Nicotinic acid | 0.5 mg/L |
| Acetic acid pyridoxine | 0.5 mg/L |
| Thiamine hydrochloride | 0.1 mg/L |
| L glycine | 2.0 mg/ml |
| Probenazole | 0.2 mM |
| trans-Zeatin | 1.5 mg/L |
| Gelrite | 3.0 g/L |

Autoclave: 121° C., 20 minutes

Evaluation of Disease Resistance of Tomato

Inoculation of *Botrytis cinerea* to tomatoes and evaluation of resistance were performed by the following methods. By using a perforator, a piece of filter paper (No. 1, Advantech Toyo, Tokyo) having a diameter of 6 mm was cut out and divided into 4 equal parts to make paper disks for inoculation. One of the inoculation paper disks was placed on a surface of a 4-week-old tomato true leaf and 5 μl of the spore suspension was dropped on the disk with a micropipettor. After inoculation with *Botrytis cinerea*, the leave was cultured in a growth chamber at 22° C. for 48 hours. The leaf with a lesion formed thereon was recorded as a digital image by an image scanner (GT-X970, Epson), and the lesion area was measured by using the image analysis software ImageJ.

Results and Discussion

Regenerated tomato lines treated with probenazole in the process of dedifferentiation/redifferentiation exhibit resistance to *Botrytis cinerea*.

As with rice and tobacco, the regenerated tomato lines of callus treated with probenazole significantly suppressed the expansion of lesions of *Botrytis cinerea* as compared to the wild type. See FIG. 12.

These results strongly suggest that in tomato belonging to the genus *Solanacea* as well as *Nicotiana benthamiana* belonging to the genus *Tobacco* among dicotyledonous plants, by inducing the expression of gene(s) of interest in the process of dedifferentiation or redifferentiation of callus, imprinting occurs in the gene(s) in the process of regeneration of plants, and the epigenetic state having disease-resistant priming imprinted therein was artificially oriented. Therefore, it was demonstrated that the method for producing a non-natural plant of the present invention can be applied to a wide range of plants.

INDUSTRIAL APPLICABILITY

The method of the present invention can be used for imparting disease resistance and stress resistance to agriculturally and horticulturally useful plants. Particularly, the method of the present invention can be used by research institutes or nursery companies other than farmers or horticulturists for providing agriculturally and horticulturally useful plants with improved disease resistance and stress resistance or seeds thereof.

The invention claimed is:

1. A method for producing a plant in which expression of a gene is induced, comprising the steps of:
   (1) providing a portion of a plant;
   (2) culturing the portion of the plant under dedifferentiation-inducing conditions to form a callus;
   (3) culturing the callus under redifferentiation-inducing conditions to form a shoot;
   (A) providing a stimulus to the callus, wherein the stimulus is a stimulus not reducing the survival rate of the callus to 90% or less, as compared to a control to which the stimulus is not provided; and
   (4) culturing the shoot to obtain the plant in which the expression of the gene is induced in the absence of the stimulus, wherein
   steps (1), (2), (3), and (4) are performed in the order of (1), (2), (3), and (4), and step (A) is performed in either or both of steps (2) and (3), wherein
   in step (2) or (3), the callus is not selected by using a resistance to the stimulus as an index, and wherein
   the stimulus is a stimulus inducing the expression of the gene in the callus.

2. The method according to claim 1, wherein the induction of the expression of the gene in the plant enhances a trait of interest of the plant, or the following step is performed after the step (3) and before the step (4), or in the step (4):
   (B) a step of confirming that the trait of interest of the plant is enhanced in the plant obtained by culturing the shoot.

3. The method according to claim 1, wherein the following step is performed after the step (3) and before the step (4), or in the step (4):
   (C) a step of confirming that the expression of the gene is induced in the absence of the stimulus in the plant obtained by culturing the shoot.

4. A method for producing a seed of a plant in which expression of a gene is induced, comprising:
   steps (1), (2), (3), (A), and (4) of the method according to claim 1; and
   (5) a step of obtaining a seed from the plant obtained by culturing the shoot, wherein
   steps (1), (2), (3), (4), and (5) are performed in the order of (1), (2), (3), (4), and (5), and step (A) is performed in either or both of steps (2) and (3), and wherein a plant obtained by germinating the seed is the plant in which the expression of the gene is induced in the absence of the stimulus.

5. The method according to claim 4, wherein the following step is performed after the step (5):
   (C) a step of confirming that the expression of the gene is induced, or a trait of interest is enhanced, in the absence of the stimulus in the plant obtained by germinating the seed.

6. A method of producing a plant in which expression of a gene is induced, comprising:
   steps (1), (2), (3), (A), and (4) of the method according to claim 1; and
   (6) a step of vegetatively propagating the plant obtained in step (4) to obtain the plant in which the expression of the gene is induced in the absence of the stimulus, wherein
   steps (1), (2), (3), (4), and (6) are performed in the order of (1), (2), (3), (4), and (6), and step (A) is performed in either or both of steps (2) and (3), and wherein in step (2) or (3), the callus is not selected by using a resistance to the stimulus as an index.

7. A method of producing a plant in which expression of a gene is induced, comprising:
   a step of vegetatively propagating the plant obtained by the method of claim 1 or the plant obtained by germinating the seed obtained by the method of claim 4 to obtain the plant in which the expression of the gene is induced in the absence of the stimulus.

8. The method according to any one of claims 1 to 6, wherein the gene is not expressed in the absence of the stimulus in the callus formed from a portion of the plant.

9. The method according to any one of claims 1 to 6, wherein the culture under the dedifferentiation-inducing conditions is performed on or in a medium containing 2,4-Dichlorophenoxyacetic acid (2,4-D), indole-3-acetic acid (IAA), 6-benzylaminopurine (6-BA), or trans-zeatin (t-zeatin).

10. The method according to any one of claims 1 to 6, wherein the culture under the redifferentiation-inducing conditions is performed on or in a medium containing kinetin, IAA, 6-BA, t-zeatin, or 1-Naphthaleneacetic acid (NAA).

11. The method according to any one of claim 2 or 5, wherein the trait is a resistance to the stimulus.

12. The method according to claim 11, wherein the stimulus is a low-temperature treatment, and wherein the trait is a low-temperature resistance.

13. The method according to any one of claim 2 or 5, wherein the trait is not a resistance to the stimulus.

14. The method according to claim 13, wherein the stimulus is a treatment with a resistance inducer activating a salicylic acid pathway, and wherein the trait is a resistance to a pathogen.

15. The method according to claim 14, wherein the resistance inducer activating a salicylic acid pathway is probenazole (3-prop-2-enoxy-1,2-benzothiazole 1,1-dioxide).

16. The method according to claim 11, wherein the stimulus is treatment with salt, and wherein the trait is a salt resistance.

17. The method according to any one of claims 1 to 6, wherein the plant is rice (*Oryza sativa*) of the Poaceae family.

18. The method according to any one of claims 1 to 6, wherein the plant is tobacco of the Solanaceae family.

19. The method according to any one of claim 2 or 5, wherein the plant is rice (*Oryza sativa*) of the Poaceae family, wherein the trait is a resistance to a pathogen, and wherein the pathogen is *Magnaporthe oryzae* or *Xanthomonas oryzae* pv. *oryzae*.

20. The method according to any one of claim 2 or 5, wherein the plant is tobacco of the Solanaceae family wherein the trait is a resistance to a pathogen, and wherein the pathogen is *Botrytis cinerea* or *Pseudomonas syringae* pv. *tabaci*.

21. The method according to any one of claims 1 to 6, wherein a step of gene recombination or a step of expressing a gene from a foreign vector is not included.

22. A method for producing a plant in which expression of a gene is induced, comprising the steps of:
(1) providing a portion of a plant;
(2) culturing the portion of the plant under dedifferentiation-inducing conditions to form a callus;
(3) culturing the callus under redifferentiation-inducing conditions to form a shoot;
(A) providing a stimulus to the callus, wherein the stimulus is a stimulus not reducing the survival rate of the callus to 90% or less, as compared to a control to which the stimulus is not provided; and
(4) culturing the shoot to obtain the plant in which the expression of the gene is induced in the absence of the stimulus, wherein
steps (1), (2), (3), and (4) are performed in the order of (1), (2), (3), and (4), and step (A) is performed in either or both of steps (2) and (3), wherein
in step (2) or (3), the callus is not selected by using a resistance to the stimulus as an index, wherein
the induction of the expression of the gene in the plant enhances a trait of interest of the plant, wherein
the stimulus is a low-temperature treatment, and wherein the trait is a low-temperature resistance.

23. A method for producing a plant in which expression of a gene is induced, comprising the steps of:
(1) providing a portion of a plant;
(2) culturing the portion of the plant under dedifferentiation-inducing conditions to form a callus;
(3) culturing the callus under redifferentiation-inducing conditions to form a shoot;
(A) providing a stimulus to the callus, wherein the stimulus is a stimulus not reducing the survival rate of the callus to 90% or less, as compared to a control to which the stimulus is not provided; and
(4) culturing the shoot to obtain the plant in which the expression of the gene is induced in the absence of the stimulus, wherein
steps (1), (2), (3), and (4) are performed in the order of (1), (2), (3), and (4), and step (A) is performed in either or both of steps (2) and (3), wherein
in step (2) or (3), the callus is not selected by using a resistance to the stimulus as an index, wherein
the induction of the expression of the gene in the plant enhances a trait of interest of the plant, wherein
the stimulus is treatment with salt, and wherein the trait is a salt resistance.

24. A method for producing a plant with an enhanced low-temperature resistance, comprising the steps of:
(1) providing a portion of a plant;
(2) culturing the portion of the plant under dedifferentiation-inducing conditions to form a callus;
(3) culturing the callus under redifferentiation-inducing conditions to form a shoot;
(A) performing a low-temperature treatment for the callus, wherein the low-temperature treatment is a low-temperature treatment not reducing the survival rate of the callus to 90% or less, as compared to a control to which the low-temperature treatment is not provided; and
(4) culturing the shoot to obtain the plant with an enhanced low-temperature resistance, wherein
steps (1), (2), (3), and (4) are performed in the order of (1), (2), (3), and (4), and step (A) is performed in either or both of steps (2) and (3), and wherein
in step (2) or (3), the callus is not selected by using a resistance to the stimulus as an index.

25. A method for producing a plant with an enhanced salt resistance, comprising the steps of:
(1) providing a portion of a plant;
(2) culturing the portion of the plant under dedifferentiation-inducing conditions to form a callus;
(3) culturing the callus under redifferentiation-inducing conditions to form a shoot;
(A) performing a treatment with salt for the callus, wherein the salt treatment is a salt treatment not reducing the survival rate of the callus to 90% or less, as compared to a control to which the salt treatment is not provided; and
(4) culturing the shoot to obtain the plant with an enhanced salt resistance, wherein
steps (1), (2), (3), and (4) are performed in the order of (1), (2), (3), and (4), and step (A) is performed in either or both of steps (2) and (3), and wherein in step (2) or (3), the callus is not selected by using a resistance to the stimulus as an index.

* * * * *